United States Patent
Tonkovich et al.

(10) Patent No.: US 7,847,138 B2
(45) Date of Patent: Dec. 7, 2010

(54) PROCESS FOR MAKING STYRENE USING MIRCOCHANNEL PROCESS TECHNOLOGY

(75) Inventors: Anna Lee Tonkovich, Dublin, OH (US); Kai Tod Paul Jarosch, Bexley, OH (US); Bin Yang, Columbus, OH (US); Francis P. Daly, Delaware, OH (US); Thomas P. Hickey, Dublin, OH (US); Jeffrey Marco, South Charleston, OH (US); Timothy J. LaPlante, Columbus, OH (US); Richard Q. Long, New Albany, OH (US)

(73) Assignee: Velocys, Inc., Plain City, OH (US)

( * ) Notice: Subject to any disclaimer, the term of this patent is extended or adjusted under 35 U.S.C. 154(b) by 873 days.

(21) Appl. No.: 11/690,319

(22) Filed: Mar. 23, 2007

(65) Prior Publication Data
US 2007/0225532 A1 Sep. 27, 2007

Related U.S. Application Data

(60) Provisional application No. 60/785,131, filed on Mar. 23, 2006.

(51) Int. Cl.
*C07C 2/66* (2006.01)
*C07C 5/333* (2006.01)

(52) U.S. Cl. ............... 585/323; 585/440; 585/444; 585/446; 585/921

(58) Field of Classification Search ............... 585/323, 585/446, 440, 444, 921
See application file for complete search history.

(56) References Cited

U.S. PATENT DOCUMENTS

| | | | |
|---|---|---|---|
| 3,882,049 A | 5/1975 | Bertolacini et al. | |
| 3,972,837 A | 8/1976 | Acres et al. | |
| 4,089,810 A | 5/1978 | Diwell et al. | |
| 4,096,095 A | 6/1978 | Cairns | |
| 4,289,652 A | 9/1981 | Hunter et al. | |
| 5,248,251 A | 9/1993 | Dalla Betta et al. | |
| 5,811,062 A | 9/1998 | Wegeng et al. | 422/129 |

(Continued)

FOREIGN PATENT DOCUMENTS

DE 246257 6/1987

(Continued)

OTHER PUBLICATIONS

Chen et al.; "Performance analysis of a folding flow micromixer"; Microfluid Nanofluid (2009) 6:763-774.

(Continued)

*Primary Examiner*—Thuan Dinh Dang
(74) *Attorney, Agent, or Firm*—Renner, Otto, Boisselle & Sklar, LLP

(57) ABSTRACT

The disclosed invention relates to a process for converting ethylbenzene to styrene, comprising: flowing a feed composition comprising ethylbenzene in at least one process microchannel in contact with at least one catalyst to dehydrogenate the ethylbenzene and form a product comprising styrene; exchanging heat between the process microchannel and at least one heat exchange channel in thermal contact with the process microchannel; and removing product from the process microchannel. Also disclosed is an apparatus comprising a process microchannel, a heat exchange channel, and a heat transfer wall positioned between the process microchannel and heat exchange channel wherein the heat transfer wall comprises a thermal resistance layer.

133 Claims, 42 Drawing Sheets

U.S. PATENT DOCUMENTS

| | | | |
|---|---|---|---|
| 6,040,266 A | 3/2000 | Fay, III et al. | |
| 6,100,436 A | 8/2000 | Wiede, Jr. et al. | 585/440 |
| 6,126,723 A | 10/2000 | Drost et al. | 96/4 |
| 6,192,596 B1 | 2/2001 | Bennett et al. | 34/76 |
| 6,200,536 B1 | 3/2001 | Tonkovich et al. | 422/177 |
| 6,284,217 B1 | 9/2001 | Wang et al. | 423/651 |
| 6,440,895 B1 | 8/2002 | Tonkovich et al. | |
| 6,451,864 B1 | 9/2002 | Wang et al. | 518/715 |
| 6,479,428 B1 | 11/2002 | Tonkovich et al. | 502/302 |
| 6,488,838 B1 | 12/2002 | Tonkovich et al. | 208/108 |
| 6,490,812 B1 | 12/2002 | Bennett et al. | 34/433 |
| 6,491,880 B1 | 12/2002 | Wang et al. | 422/211 |
| 6,503,298 B1 | 1/2003 | Monzyk et al. | 95/96 |
| 6,508,862 B1 | 1/2003 | Tonkovich et al. | 95/106 |
| 6,533,840 B2 | 3/2003 | Martin et al. | 95/45 |
| 6,540,975 B2 | 4/2003 | Tonkovich et al. | 423/659 |
| 6,558,634 B1 | 5/2003 | Wang et al. | 422/173 |
| 6,607,678 B2 | 8/2003 | Wang et al. | 252/373 |
| 6,616,909 B1 | 9/2003 | Tonkovich et al. | 423/848.1 |
| 6,622,519 B1 | 9/2003 | Mathias et al. | 62/611 |
| 6,652,627 B1 | 11/2003 | Tonkovich et al. | 95/104 |
| 6,660,237 B2 | 12/2003 | Wang et al. | 422/222 |
| 6,666,909 B1 | 12/2003 | TeGrotenhuis et al. | 95/273 |
| 6,680,044 B1 | 1/2004 | Tonkovich et al. | 423/652 |
| 6,734,137 B2 | 5/2004 | Wang et al. | 502/328 |
| 6,762,149 B2 | 7/2004 | Tonkovich et al. | 502/439 |
| 6,814,781 B2 | 11/2004 | Tonkovich et al. | 95/90 |
| 6,851,171 B2 | 2/2005 | Schmitt | 29/469 |
| 6,875,247 B2 | 4/2005 | TeGrotenhuis et al. | 55/319 |
| 6,969,505 B2 | 11/2005 | Tonkovich et al. | 423/648.1 |
| 6,969,506 B2 | 11/2005 | Tonkovich et al. | 423/652 |
| 6,984,363 B2 | 1/2006 | Tonkovich et al. | 422/173 |
| 6,989,134 B2 | 1/2006 | Tonkovich et al. | 422/189 |
| 7,000,427 B2 | 2/2006 | Mathias et al. | 62/612 |
| 7,008,969 B2 | 3/2006 | Wang et al. | 518/715 |
| 7,014,835 B2 | 3/2006 | Mathias et al. | 423/652 |
| 7,029,647 B2 | 4/2006 | Tonkovich et al. | 423/584 |
| 7,045,114 B2 | 5/2006 | Tonkovich et al. | 423/659 |
| 7,077,643 B2 | 7/2006 | Holladay et al. | 431/215 |
| 7,084,180 B2 | 8/2006 | Wang et al. | 518/712 |
| 7,220,390 B2 | 5/2007 | Tonkovich et al. | 422/172 |
| 7,234,514 B2 | 6/2007 | Vogel | 165/170 |
| 7,250,074 B2 | 7/2007 | Tonkovich et al. | 95/130 |
| 7,255,845 B2 | 8/2007 | Tonkovich et al. | 423/437.2 |
| 2003/0116503 A1 | 6/2003 | Wang et al. | 210/660 |
| 2003/0219903 A1 | 11/2003 | Wang et al. | 436/37 |
| 2004/0034266 A1 | 2/2004 | Brophy et al. | 585/658 |
| 2004/0220434 A1 | 11/2004 | Brophy et al. | 568/959 |
| 2004/0228882 A1 | 11/2004 | Qiu et al. | 424/400 |
| 2004/0229752 A1 | 11/2004 | Long et al. | 502/303 |
| 2004/0234566 A1 | 11/2004 | Qiu et al. | 424/401 |
| 2005/0087767 A1 | 4/2005 | Fitzgerald et al. | 257/200 |
| 2005/0176832 A1 | 8/2005 | Tonkovich et al. | 518/726 |
| 2005/0272965 A1 | 12/2005 | Watson et al. | 585/658 |
| 2006/0016215 A1 | 1/2006 | Tonkovich et al. | 62/617 |
| 2006/0016216 A1 | 1/2006 | Tonkovich et al. | 62/617 |
| 2006/0036106 A1 | 2/2006 | Mazanec et al. | 549/533 |
| 2006/0073080 A1 | 4/2006 | Tonkovich et al. | 422/100 |
| 2006/0102519 A1 | 5/2006 | Tonkovich et al. | 208/107 |
| 2006/0120213 A1 | 6/2006 | Tonkovich et al. | 366/144 |
| 2006/0129015 A1 | 6/2006 | Tonkovich et al. | 585/709 |
| 2006/0249020 A1 | 11/2006 | Tonkovich et al. | 95/115 |
| 2007/0004810 A1 | 1/2007 | Wang et al. | 518/718 |
| 2007/0085227 A1 | 4/2007 | Tonkovich et al. | 261/127 |

FOREIGN PATENT DOCUMENTS

| | | |
|---|---|---|
| DE | 3926466 | 2/1991 |
| EP | 0 397 637 A1 | 11/1990 |
| EP | 0 841 317 A1 | 5/1998 |
| EP | 1 142 631 A1 | 10/2001 |
| EP | 1102628 | 11/2006 |
| GB | 1531134 | 11/1978 |
| GB | 2077136 | 12/1981 |
| WO | 9421372 | 9/1994 |
| WO | 9700442 | 1/1997 |
| WO | 9828073 | 7/1998 |
| WO | 9838147 | 9/1998 |
| WO | 9916542 | 4/1999 |
| WO | 0006301 | 2/2000 |
| WO | 03006149 | 1/2003 |
| WO | 03/078052 A1 | 9/2003 |
| WO | 03/106386 A2 | 12/2003 |
| WO | 2004/091772 A1 | 10/2004 |
| WO | 2004/103549 A2 | 12/2004 |
| WO | 2006/127889 A2 | 11/2006 |
| ZA | 855317 | 7/1985 |

OTHER PUBLICATIONS

MacInnes et al.; "Investigation of alternating-flow mixing in microchannels"; Chemical Engineering Science 60; 2005; pp. 3453-3467.

MacInnes et al.; "Numerial characterization of floding flow microchannel mixers"; Chemical Engineering Science 62; 2007; pp. 2718-2727.

MacInnes et al.; "Mixing Strategies for Flow in Microchannel Devices"; Chemical and Process Engineering, University of Sheffield, Nov. 24, 2004.

Cybulski et al.; "Monoliths in Heterogeneous Catalysis"; Catal. Rev.—Sci. Eng., 36(2), 179-270 (1994).

Bennett et al.; "Microchannel cooled heatsinks for high average power laser diode arrays"; SPIE, vol. 1865; 1993; pp. 144-153.

International Application PCT/US2007/007240, International Search Report and Written Opinion mailed Nov. 19, 2007.

International Application PCT/US2007/007240, Response to Written Opinion filed Feb. 19, 2008.

International Application PCT/US2007/007240, International Preliminary Report on Patentability mailed Jul. 1, 2008.

Kandlikar; "Exploring Roughness Effect on Laminar Internal Flow—Are We Ready for Change?"; Nanoscale and Microscale Thermophysical Engineering; 2008; pp. 61-82; vol. 12; Taylor & Francis Group, LLC.

"Lummus/UOP Class SM™ Process"; UOP, Process Technology and Equipment, UOP 4217-32; 1103 PTEOCI; 2004.

International Application PCT/US2007/007240, Partial International Search Report, mailed Sep. 25, 2007.

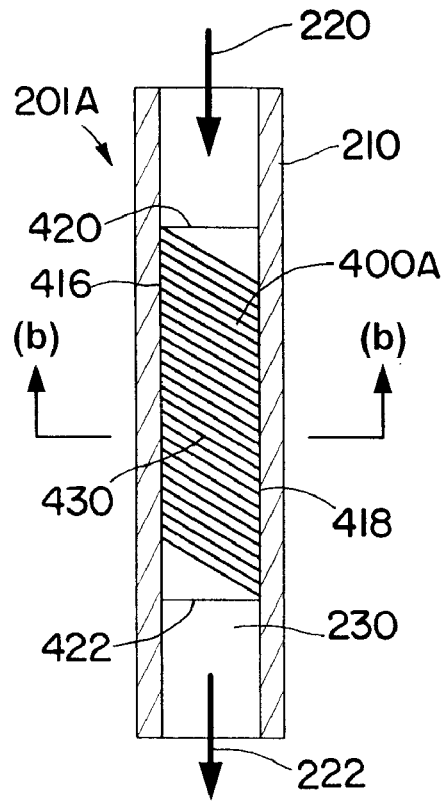
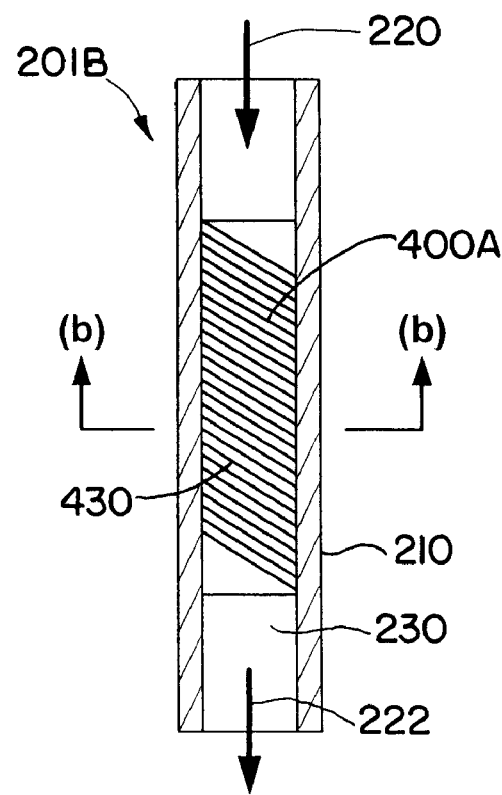
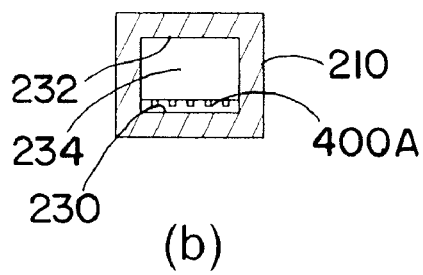
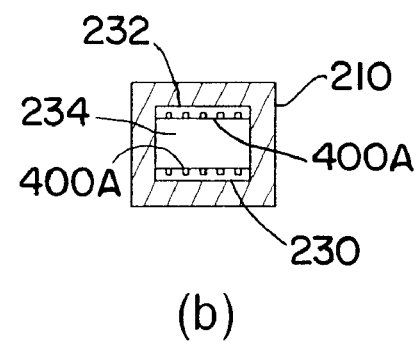
FIG. 32      FIG. 33

$$Q = \frac{k}{H} \Delta T$$

PROCESS FOR MAKING STYRENE USING MIRCOCHANNEL PROCESS TECHNOLOGY

This application claims priority under 35 U.S.C. §119(e) to U.S. Provisional Application Ser. No. 60/785,131 filed Mar. 23, 2006. The disclosure in this provisional application is incorporated herein by reference.

TECHNICAL FIELD

This invention relates to a process for making styrene using microchannel process technology.

BACKGROUND

Styrene is typically produced commercially by dehydrogenating ethylbenzene in the presence of an iron-based catalyst. This reaction is endothermic and equilibrium limited. The process is usually operated at temperatures between about 600-850° C. and at atmospheric or sub-atmospheric pressure. Steam is often co-fed to the reactor with the ethylbenzene. A problem with the process is that it consumes a high level of energy. The conversion of ethylbenzene is typically below 65% to maintain selectivity to styrene in excess of 95%. As a result, reactant recycles are often needed. However, the separation of unreacted ethylbenzene from styrene is costly due to the close boiling points of ethylbenzene (136° C.) and styrene (145° C.).

The use of oxidative dehydrogenation of ethylbenzene has been suggested as a substitute for the dehydrogenation of ethylbenzene. Thus far this process has not been commercialized. This reaction is exothermic. Although high styrene selectivities may be achieved, ethylbenzene conversions less than 60% are typically obtained in order to provide for such high selectivities. An increase in the reaction temperature may increase the ethylbenzene conversion, but styrene selectivity tends to decrease significantly due to combustion of styrene and ethylbenzene. The presence of hot spots in the catalyst bed tends to sinter the catalyst resulting in catalyst deactivation.

This invention, in at least one embodiment, provides a solution to these problems.

SUMMARY

This invention relates to a process for converting ethylbenzene to styrene, comprising: flowing a feed composition comprising ethylbenzene in at least one process microchannel in contact with at least one catalyst to dehydrogenate the ethylbenzene and form a product comprising styrene; exchanging heat between the process microchannel and at least one heat exchange channel in thermal contact with the process microchannel; and removing product from the process microchannel.

In one embodiment, the gas hourly space velocity for the flow of the feed composition in the process microchannel may be at least about 1000 normal liters of feed per hour per liter of volume. The conversion of ethylbenzene may be at least about 50% per cycle or per pass through the process microchannel. The selectivity to styrene may be at least about 70%.

In one embodiment, the catalyst may comprise at least one dehydrogenation catalyst.

In one embodiment, the feed composition may be combined with oxygen and the catalyst may comprise at least one oxidative dehydrogenation catalyst.

In one embodiment, a staged addition feed stream comprising the oxygen may flow in a staged addition channel, the staged addition channel being adjacent to the process microchannel, the process microchannel having an entrance for the feed composition, the feed composition entering the process microchannel through the entrance for the feed composition, the staged addition feed stream flowing from the staged addition channel into the process microchannel, the staged addition feed stream entering the process microchannel downstream of the entrance for the feed composition and contacting the feed composition in the process microchannel.

In one embodiment, the process may be conducted in a microchannel reactor comprising a plurality of the process microchannels and a plurality of the heat exchange channels.

In one embodiment, the invention relates to a process for converting ethylbenzene to styrene, comprising: flowing a feed composition comprising ethylbenzene in at least one process microchannel in contact with at least one catalyst to dehydrogenate the ethylbenzene and form a product comprising styrene; exchanging heat between the process microchannel and at least one heat exchange channel in thermal contact with the process microchannel; and removing product from the process microchannel; wherein the catalyst comprises at least one dehydrogenation catalyst; the catalyst being supported on a support, the support comprising a microgrooved support strip with a support strip having a length with a center axis extending along the length, a first surface, a first side edge, a second side edge, a front edge extending from the first side edge to the second side edge, a back edge extending from the first side edge to the second side edge, a plurality of parallel microgrooves in the first surface extending between the first side edge and the second side edge at an angle relative to the center axis sufficient to permit fluid flowing in the microgrooves to flow in a direction from the front edge to the back edge of the microgrooved strip. In one embodiment, the microgrooves project part way through the support strip from the first surface to the second surface. In one embodiment, the microgrooves project all the way through the support strip thereby providing open microgrooves that may be suitable for permitting fluid to flow through the support strip. In one embodiment, process fluids may flow over or by the microgrooves in a flow-by manner. In one embodiment, the microgrooves may extend across the entire width of the process microchannel, and in one embodiment they may extend over only part of the width of the process microchannel.

In one embodiment, the invention relates to a process for converting ethylbenzene to styrene, comprising: flowing a feed composition comprising ethylbenzene in at least one process microchannel in contact with at least one catalyst to dehydrogenate the ethylbenzene and form a product comprising styrene; exchanging heat between the process microchannel and at least one heat exchange channel in thermal contact with the process microchannel; and removing product from the process microchannel; wherein the catalyst comprises at least one dehydrogenation catalyst; the catalyst being supported by a composite support structure, the composite support structure being a flow through structure, the feed composition contacting the catalyst in the composite support structure and reacting to form the product, the composite support structure comprising: at least one first support strip comprising a first surface, a second surface, a length with a center axis extending along the length, a front edge, a back edge, a first side edge, a second side edge, the front edge and the back edge extending from the first side edge and to the second side edge, a plurality of parallel microgrooves in the first surface extending from the front edge to the second side edge, and a plurality of parallel microgrooves in the first surface extending from first side edge to the back edge; at least one second support strip comprising a first surface, a second surface, a length with a center axis extending along the length, a front edge, a back edge, a first side edge, a second side edge, the front edge and the back edge extending from the first side edge to the second side edge, a plurality of parallel microgrooves in the first surface extending from the front edge to the first side edge, and a plurality of parallel microgrooves in the first surface extending from second side edge to the back edge; the first support strip being adjacent to the second support strip with the second surface of the first support strip contacting the first surface of the second support strip; the front and back edges of each of the support strips being open to permit fluid to flow through the front and back edges; the side edges of each of the support strips being closed to prevent fluid from flowing through the side edges; each of the microgrooves penetrating through the support strips sufficiently to permit fluid to flow through the support strips from one support strip to another; the microgrooves in the first surface of the first support strip being oriented toward the front edge and the first side edge of the first support strip and forming an angle with the center axis of more than about 0° and less than 90°; and the microgrooves in the first surface of the second support strip being oriented toward the front edge and the first side edge of the second support strip and forming an angle with the center axis of more than 90° and less than about 180°.

In one embodiment, the invention relates to a process for converting ethylbenzene to styrene, comprising: flowing a feed composition comprising ethylbenzene in at least one process microchannel in contact with at least one catalyst to dehydrogenate the ethylbenzene and form a product comprising styrene; exchanging heat between the process microchannel and at least one heat exchange channel in thermal contact with the process microchannel; and removing product from the process microchannel; wherein the feed composition is combined with oxygen and the catalyst comprises at least one oxidative dehydrogenation catalyst; wherein the catalyst is supported on a support, the support comprising a microgrooved support strip with a support strip having a length with a center axis extending along the length, a first surface, a first side edge, a second side edge, a front edge extending from the first side edge to the second side edge, a back edge extending from the first side edge to the second side edge, a plurality of parallel microgrooves in the first surface extending between the first side edge and the second side edge at an angle relative to the center axis sufficient to permit fluid flowing in the microgrooves to flow in a direction from the front edge to the back edge of the microgrooved support strip.

In one embodiment, the invention relates to a process for converting ethylbenzene to styrene, comprising: flowing a feed composition comprising ethylbenzene in at least one process microchannel in contact with at least one catalyst to dehydrogenate the ethylbenzene and form a product comprising styrene; exchanging heat between the process microchannel and at least one heat exchange channel in thermal contact with the process microchannel; and removing product from the process microchannel; wherein the feed composition is combined with oxygen and the catalyst comprises at least one oxidative dehydrogenation catalyst; and wherein the catalyst is supported by a composite support structure, the composite support structure being a flow through structure, the feed composition and oxygen contacting the catalyst in the composite support structure and reacting to form the product, the composite support structure comprising: at least one first support strip comprising a first surface, a second surface, a length with a center axis extending along the length, a front edge, a back edge, a first side edge, a second side edge, the front edge and the back edge extending from the first side edge and to the second side edge, a plurality of parallel microgrooves in the first surface extending from the front edge to the second side edge, and a plurality of parallel microgrooves in the first surface extending from first side edge to the back edge; at least one second support strip comprising a first surface, a second surface, a length with a center axis extending along the length, a front edge, a back edge, a first side edge, a second side edge, the front edge and the back edge extending from the first side edge to the second side edge, a plurality of parallel microgrooves in the first surface extending from the front edge to the first side edge, and a plurality of parallel microgrooves in the first surface extending from second side edge to the back edge; the first support strip being adjacent to the second support strip with the second surface of the first support strip contacting the first surface of the second support strip; the front and back edges of each of the support strips being open to permit fluid to flow through the front and back edges; the side edges of each of the support strips being closed to prevent fluid from flowing through the side edges; each of the microgrooves penetrating through the support strips sufficiently to permit fluid to flow through the support strips from one support strip to another; the microgrooves in the first surface of the first support strip being oriented toward the front edge and the first side edge of the first support strip and forming an angle with the center axis of more than about 0° and less than 90°; and the microgrooves in the first surface of the second support strip being oriented toward the front edge and the first side edge of the second support strip and forming an angle with the center axis of more than 90° and less than about 180°.

In one embodiment, the invention relates to a process for converting ethylbenzene to styrene, comprising: flowing a feed composition comprising ethylbenzene in at least one process microchannel in contact with at least one catalyst to dehydrogenate the ethylbenzene and form a product comprising styrene; exchanging heat between the process microchannel and at least one heat exchange channel in thermal contact with the process microchannel; and removing product from the process microchannel; wherein the feed composition is combined with oxygen and the catalyst comprises at least one oxidative dehydrogenation catalyst; wherein a staged addition feed stream comprising the oxygen flows in a staged addition channel, the staged addition channel being adjacent to the process microchannel, the process microchannel having an entrance for the feed composition, the feed composition entering the process microchannel through the entrance for the feed composition, the staged addition feed stream flowing from the staged addition channel into the process microchannel, the staged addition feed stream entering the process microchannel downstream of the entrance for the feed composition and contacting the feed composition in the process microchannel.

In one embodiment, the invention relates to an apparatus, comprising: a process microchannel; a heat exchange channel; and a heat transfer wall positioned between the process microchannel and the heat exchange channel, the heat transfer wall comprising at least one thermal resistance layer. This apparatus may be used as a repeating unit in a microchannel reactor.

In one embodiment, the invention relates to a microchannel reactor comprising the foregoing apparatus.

In one embodiment, the invention relates to an apparatus, comprising: a plurality of the foregoing microchannel reactors positioned in a vessel, each microchannel reactor comprises a plurality of process microchannels, a plurality of heat exchange channels, and optionally a plurality of staged addition channels; the vessel being equipped with a manifold for flowing a feed to the process microchannels, a manifold for flowing product from the process microchannels, a manifold for flowing heat exchange fluid to the heat exchange channels, optionally a manifold for flowing oxygen or a source of oxygen to the staged addition channels, and a manifold for flowing heat exchange fluid from the heat exchange channels. In one embodiment, each microchannel reactor may comprise from about 1 to about 50,000 process microchannels, and the vessel may comprise from 1 to about 1000 microchannel reactors.

This invention, in at least one embodiment, provides the advantage of increasing product yield and energy efficiency by improving heat and mass transfer performance. With this invention it is possible to reduce capital costs by reducing the size of processing equipment and the number of downstream separation units. Catalyst productivity may be enhanced by allowing the catalyst to operate in its peak performance window and by avoiding hot spots. With this invention it is possible to provide cost-effective plant expansion by adding incremental capacity with favorable economics.

BRIEF DESCRIPTION OF THE DRAWINGS

In the annexed drawings, like parts and features have like designations. A number of the annexed drawings are schematic illustrations which are not necessarily proportioned accurately or drawn to scale.

FIG. 32(a) is a schematic illustration of a repeating unit comprising a process microchannel that may be used in the microchannel reactor illustrated in FIG. 6. The process microchannel contains a microgrooved support strip as illustrated in FIG. 28, the microgrooved support strip supporting a catalyst. FIG. 32(b) is a cross-sectional view of the process microchannel illustrated in FIG. 32(a) taken along line (b)-(b) in FIG. 32(a).

FIG. 33 is a schematic illustration of a repeating unit comprising a process microchannel that may be used in the microchannel reactor illustrated in FIG. 6. The process microchannel is similar to the process microchannel illustrated in FIG. 32(a) with the exception that the process microchannel illustrated in FIG. 33(a) contains opposite interior walls and a catalyst supporting microgrooved support strip positioned on each of the opposite interior walls. FIG. 33(b) is a cross-sectional view of the process microchannel illustrated in FIG. 33(a) taken along line (b)-(b) of FIG. 33(a).

DETAILED DESCRIPTION

All ranges and ratio limits disclosed in the specification may be combined. It is to be understood that unless specifically stated otherwise, references to "a," "an," and/or "the" may include one or more than one and that reference to an item in the singular may also include the item in the plural.

Figure 1:
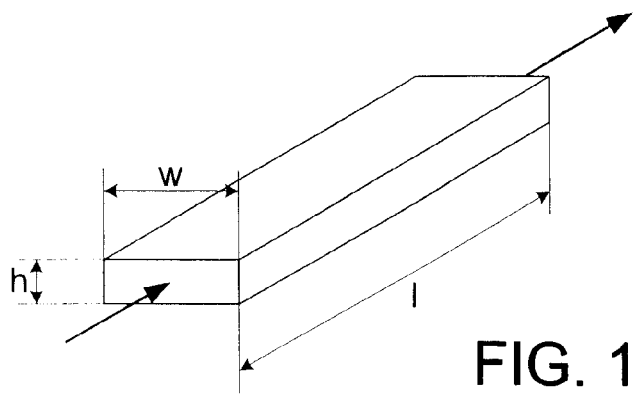
FIG. 1 is a schematic illustration of a microchannel which may be used in accordance with the invention.

The term "microchannel" may refer to a channel having at least one internal dimension of height or width of up to about 10 millimeters (mm), and in one embodiment up to about 5 mm, and in one embodiment up to about 2 mm, and in one embodiment up to about 1 mm. The microchannel may comprise at least one inlet and at least one outlet wherein the at least one inlet is distinct from the at least one outlet. The microchannel may not be merely an orifice. The microchannel may not be merely a channel through a zeolite or a mesoporous material. An example of a microchannel that may be used with the inventive process as a process microchannel and/or a heat exchange microchannel is illustrated in FIG. 1. Referring to FIG. 1, the illustrated microchannel has a height (h), width (w) and length (l). Fluid may flow through the microchannel in the direction indicated by the arrows. Both the height (h) and width (w) are perpendicular to the flow of fluid through the microchannel. The height (h) or width (w) of the microchannel may be in the range of about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other dimension of height (h) or width (w) may be of any dimension, for example, up to about 3 meters, and in one embodiment about 0.01 to about 3 meters, and in one embodiment about 0.1 to about 3 meters. The length (l) of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. Although the microchannel illustrated in FIG. 1 has a cross section that is rectangular, it is to be understood that the microchannel may have a cross section having any shape, for example, a square, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "process microchannel" may refer to a microchannel wherein a process is conducted. The process may relate to converting ethylbenzene (EB) to styrene. The process microchannel may contain one or more catalysts.

The term "microchannel reactor" may refer to an apparatus comprising at least one process microchannel for conducting a reaction. The reactor may be used for converting ethylbenzene to styrene. The microchannel reactor may comprise a plurality of the process microchannels that may be operated in parallel, a header or manifold assembly for providing for the flow of fluid into the process microchannels, and a footer or manifold assembly providing for the flow of fluid out of the process microchannels. The microchannel reactor may comprise one or more heat exchange channels, for example heat exchange microchannels, adjacent to and/or in thermal contact with the process microchannels for cooling and/or heating the contents of the process microchannels.

The term "structured wall" or "SW" may refer to an interior channel wall, for example, a microchannel wall, with one or more strips or shims positioned or mounted on its surface. The strips or shims may contain one or more void spaces, openings or through holes. Two or more layers of the strips or shims may be stacked one above another or positioned side by side to provide a porous structure positioned or mounted on the channel wall. A catalyst may be supported by the structured wall. An open bulk flow region or gap may be positioned in the process microchannel adjacent the structured wall.

The term "structured wall reactor" may refer to a microchannel reactor comprising at least one process microchannel wherein the process microchannel contains one or more structured walls. A catalyst may be supported by the one or more structured walls. An open bulk flow region or gap may be positioned in the process microchannel adjacent the structured wall.

The term "volume" with respect to volume within a process microchannel may include all volume in the process microchannel a process fluid may flow through or flow by. This volume may include the volume within the void spaces, openings or holes in a structured wall within the process microchannel. This volume may include volume within surface features that may be positioned in the process microchannel and adapted for the flow of fluid in a flow-through manner or in a flow-by manner.

The term "shim" may refer to a planar or substantially planar sheet or plate. The thickness of the shim may be the smallest dimension of the shim and may be up to about 2 mm, and in one embodiment in the range from about 0.05 to about 2 mm, and in one embodiment in the range of about 0.05 to about 1 mm, and in one embodiment in the range from about 0.05 to about 0.5 mm. The shim may have any length and width.

The term "surface feature" may refer to a depression in a microchannel wall and/or a projection from a microchannel wall that modifies flow and/or mixing within the microchannel. The surface features may be in the form of circles, spheres, frustrums, oblongs, squares, rectangles, angled rectangles, checks, chevrons, vanes, air foils, wavy shapes, and the like. The surface features may contain subfeatures where the major walls of the surface features further contain smaller surface features that may take the form of notches, waves, indents, holes, burrs, checks, scallops, and the like. The surface features may have a depth, a width, and for non-circular surface features a length. Examples are illustrated in FIGS. 39-45. The surface features may be formed on or in one or more of the interior walls of the process microchannels. The surface features may be positioned in or on one or more strips or shims used to form one or more structured walls within a microchannel. The surface features may be formed on or in one or more of the apertured sections that may be used with the process microchannels. The surface features may be formed on or in one or more of the interior walls of the heat exchange channels employed herein. The surface features may be referred to as passive surface features or passive mixing features. The surface features may be used to disrupt laminar flow streamlines and create advective flow at an angle to the bulk flow direction. The surface features may be used to enhance contact between reactants and catalyst, or enhance heat transfer.

The term "microgroove" may refer to a groove in a substrate having a depth of up to about 1000 microns, and in one embodiment in the range from about 1 to about 1000 microns, and in one embodiment in the range from about 1 to about 500 microns, and in one embodiment from about 1 to about 100 microns. The substrate may be a strip or shim used as a support structure for a catalyst and/or to form a structured wall. The microgrooves may penetrate all the way through the substrate over part or all of the length of the microgrooves. The microgrooves may penetrate only partially through the substrate. The depth of the microgrooves may be measured at the deepest point of penetration into the substrate. The microgrooves may have a width up to about 1000 microns, and in one embodiment in the range from about 0.1 to about 1000 microns, and in one embodiment in the range from about 1 to about 500 microns. The width may be the width measured at the widest point of the microgroove. The microgroove may have any length, for example, up to about 100 cm, and in one embodiment from about 0.1 to about 100 cm, and in one embodiment from about 0.1 to about 10 cm. The microgroove may have a cross section of any shape. Examples include square, rectangle, vee, semi-circle, dovetail, trapezoid, and the like. The shape and/or size of the cross section of the microgroove may vary over the length of the microgroove.

The term "heat exchange channel" may refer to a channel having a heat exchange fluid in it that may give off heat and/or absorb heat. The heat exchange channel may be a microchannel.

The term "heat transfer wall" may refer to a common wall between a process microchannel and an adjacent heat exchange channel where heat transfers from one channel to the other through the common wall.

The term "thermal resistance layer" may refer to a layer on either or both sides of a heat transfer wall or embedded within a heat transfer wall that reduces the flow of heat through the heat transfer wall. In one embodiment, the thermal resistance layer is embedded within the heat transfer wall and may not directly contact the interior of the process microchannel and/or the interior of the heat exchange channel. The thermal resistance layer may comprise a vacuum, a gaseous material (e.g., air or an inert gas), a liquid material (e.g., a high boiling liquid) and/or a solid material. The solid material may contain void spaces, openings or through holes. The thermal resistance layer may be made of the same or substantially the same material as the heat transfer wall except that it may have a lower density than the heat transfer wall. The thermal resistance layer and/or heat transfer wall may comprise one or more sub-assemblies of a thermal resistant construction. Each sub-assembly may comprise two or more shims stacked one above another with one or more void spaces positioned between the shims. The void spaces may comprise a vacuum or a gas such as air or an inert gas. The thermal resistance layer may comprise any desired number of these sub-assemblies stacked one above another, for example, from 1 to about 100 sub-assemblies. The thermal resistance layer may comprise one or more strips or shims containing void spaces, openings and/or through holes. The strips or shims may contain grooves (e.g., microgrooves) in either or both sides of the strips or shims. The thermal resistance layer may comprise a plurality of strips or shims containing void spaces, openings and/or through holes, the strips or shims being stacked one above another resulting in the formation of a porous structure. The thermal resistance layer may be constructed of any suitable material that provides desired properties of thermal resistance (e.g., metal, metal alloy, ceramics, glass, quartz, silicon, polymer, or combinations of two or more thereof, etc.). The thermal resistance layer may have a void volume in the range from about 1% to about 99%, and in one embodiment from about 10% to about 90%. Alternatively, the thermal resistance layer may have a non-solid volume in the range from about 1% to about 99%, and in one embodiment from about 10% to about 90%. The thermal resistance layer may have a varying solid to void ratio or solid to non-solid ratio over the length and/or width of the heat transfer wall. The thermal resistance layer may have physical properties and/or a form that varies as a function of distance over the length of the heat transfer wall. For example, the thermal resistance layer may exhibit heat transfer characteristics that are relatively low at the entrance to a process microchannel and increase gradually or abruptly to a higher level near the exit of the process microchannel, or vice versa. The thermal resistance layer may change in composition gradually or abruptly as a function of distance from one location to another along the length of the heat transfer wall. The thickness of the thermal resistance layer may comprise from about 1 to about 99% of the thickness of the heat transfer wall, and in one embodiment from about 10 to about 90%.

The term "heat exchange fluid" may refer to a fluid that may give off heat and/or absorb heat.

The term "adjacent" when referring to the position of one channel relative to the position of another channel may mean directly adjacent such that a wall separates the two channels. This wall may vary in thickness. However, "adjacent" channels may not be separated by an intervening channel that would interfere with heat transfer between the channels.

The term "thermal contact" may refer to two bodies, for example channels, that are not necessarily in contact with each other or adjacent to each other but still may exchange heat with each other. Thus, for example, one body in thermal contact with another body may heat or cool the other body.

The term "fluid" may refer to a gas, a liquid, or a gas or a liquid containing dispersed solids, or a mixture thereof. The fluid may be in the form of a gas containing dispersed liquid droplets.

The term "bulk flow region" may refer to open areas within a process microchannel. A contiguous bulk flow region may allow rapid fluid flow through a process microchannel without significant pressure drops. In one embodiment there may be laminar flow in the bulk flow region. A bulk flow region may comprise at least about 5%, and in one embodiment from about 30 to about 80% of the internal volume of a process microchannel or the cross-sectional area of the process microchannel.

The term "residence time," which may also be referred to as the "average residence time," may be the internal volume of a channel occupied by a fluid flowing through the channel divided by the average volumetric flowrate for the fluid flowing through the channel at the temperature and pressure being used.

The terms "upstream" and "downstream" may refer to positions within a channel (e.g., a process microchannel) that is relative to the direction of flow of a fluid stream in the channel. For example, a position within the channel not yet reached by a portion of a fluid stream flowing toward that position would be downstream of that portion of the fluid stream. A position within the channel already passed by a portion of a fluid stream flowing away from that position would be upstream of that portion of the fluid stream. The terms "upstream" and "downstream" do not necessarily refer to a vertical position since the channels used herein may be oriented horizontally, vertically or at an inclined angle.

The terms "standard cubic feet" or "standard cubic meters" refer to volumes measured at a temperature of 20° C. and atmospheric pressure.

The term "normal liters" refers to volumes measured at a temperature of 20° C. and atmospheric pressure.

The term "gauge pressure" refers to absolute pressure, less atmospheric pressure. For example, a gauge pressure of zero atmospheres corresponds to atmospheric pressure. However, throughout the text and in the appended claims, unless otherwise indicated, all pressures are absolute pressures.

The term "graded catalyst" may refer to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel, or vice versa; or a lower concentration of catalytically active metal nearer the center (i.e., midpoint) of a process microchannel and a higher concentration nearer a process microchannel wall, or vice versa, etc. The thermal conductivity of a graded catalyst may vary from one location to another within a process microchannel. The surface area of a graded catalyst may be varied by varying size of catalytically active metal sites on a constant surface area support, or by varying the surface area of the support such as by varying support type or particle size. A graded catalyst may have a porous support where the surface area to volume ratio of the support is higher or lower in different parts of the process microchannel followed by the application of the same catalyst coating everywhere. A combination of two or more of the preceding embodiments may be used. The graded catalyst may have a single catalytic component or multiple catalytic components (for example, a bimetallic or trimetallic catalyst). The graded catalyst may change its properties and/or composition gradually as a function of distance from one location to another within a process microchannel. The graded catalyst may comprise rimmed particles that have "eggshell" distributions of catalytically active metal within each particle. The graded catalyst may be graded in the axial direction along the length of a process microchannel or in the lateral direction. The graded catalyst may have different catalyst compositions, different loadings and/or numbers of active catalytic sites that may vary from one position to another position within a process microchannel. The number of catalytically active sites may be changed by altering the porosity of the catalyst structure. This may be accomplished using a washcoating process that deposits varying amounts of catalytic material. An example may be the use of different porous catalyst thicknesses along the process microchannel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "conversion of oxygen" refers to the oxygen mole change between reactant (including all oxygen added using staged addition) and product divided by the moles of oxygen in the reactant.

The term "conversion of ethylbenzene" refers to the ethylbenzene mole change between reactant and product divided by the moles of ethylbenzene in the reactant.

The term "selectivity to styrene" refers to the moles of styrene produced divided by the moles of styrene produced plus moles of ethylbenzene in the product.

The term "cycle" refers to a single pass of the reactants through the process microchannels.

The term "ml (milliliter) per gram of catalyst per hour" refers to a volume (ml) of product produced per gram of catalyst per hour wherein the gram of catalyst refers to catalytic material in the catalyst but not any support that may be present.

The term "yield" refers to moles of reactant converted to a specific product (for example, styrene) divided by the number of moles of reactant converted. The yield may be calculated by The term "mm" may refer to millimeter. The term "nm" may refer to nanometer. The term "ms" may refer to millisecond. The term "μm" may refer to micron or micrometer. The terms "micron" and "micrometer" have the same meaning and may be used interchangeably.

The inventive process for converting ethylbenzene (EB) to styrene may be a dehydrogenation (DH) process or an oxidative dehydrogenation (ODH) process. The dehydrogenation reaction is an endothermic reaction, while the oxidative dehydrogenation reaction is an exothermic reaction. Although both processes may be conducted in a microchannel reactor in accordance with the invention, heat management with the oxidative dehydrogenation process may be easier and therefore advantageous. The inventive process for making styrene may be employed in a process where ethylene is formed in a microchannel reactor upstream of the styrene forming microchannel reactor. Also, the ethylbenzene may be formed upstream of the styrene forming microchannel reactor in an alkylation reactor. The alkylation reactor may be a microchannel reactor or a conventional alkylation reactor. When the process is an oxidative dehydrogenation process, oxygen or a source of oxygen may be used. The source of oxygen may be air or oxygen enriched air. The ethylbenzene may be mixed with air and/or steam. Flow sheets illustrating a number of these processes are provided in FIGS. 2-5.

Figure 2:
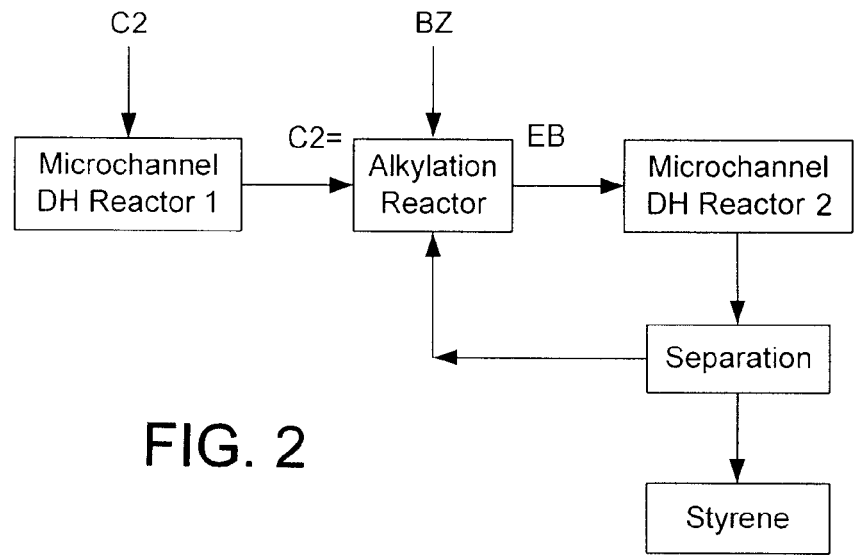
FIG. 2 is a flow sheet illustrating one embodiment of a process for making styrene in accordance with the invention.

Referring to FIG. 2, ethane (C2) is dehydrogenated (DH) in a first microchannel reactor to form ethylene (C2=). The ethylene is fed with benzene (BZ) to an alkylation reactor where ethylbenzene (EB) is formed. The ethylbenzene is then dehydrogenated to form styrene in a second microchannel reactor. Styrene and ethylbenzene are separated and the unreacted ethylbenzene may be recycled.

Figure 3:
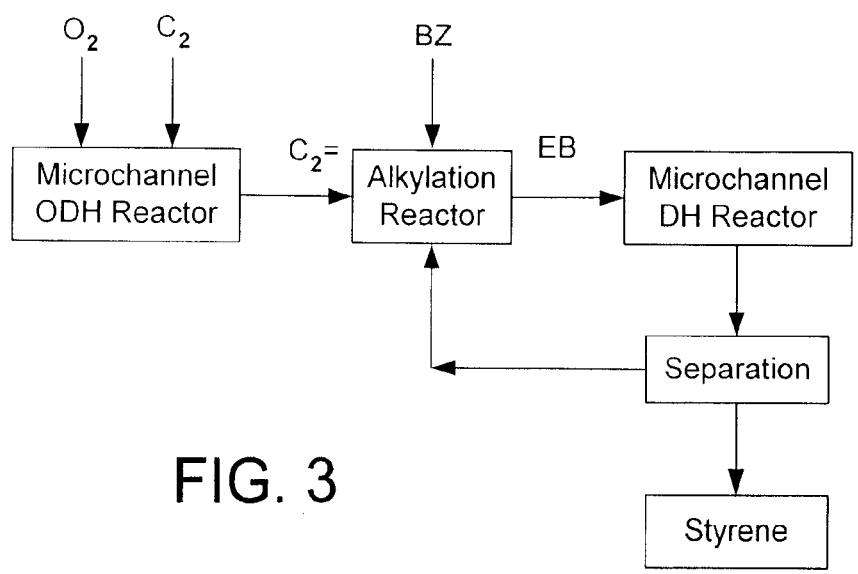
FIG. 3 is a flow sheet illustrating an alternate embodiment of a process for making styrene in accordance with the invention.

In the process illustrated in FIG. 3, ethane is oxidatively dehydrogenated (ODH) in a first microchannel reactor to form ethylene. The ethylene is fed together with benzene to an alkylation reactor to produce ethylbenzene. Ethylbenzene is then dehydrogenated to form styrene in a second microchannel reactor. Styrene and ethylbenzene are separated and the unreacted ethylbenzene may be recycled.

Figure 4:
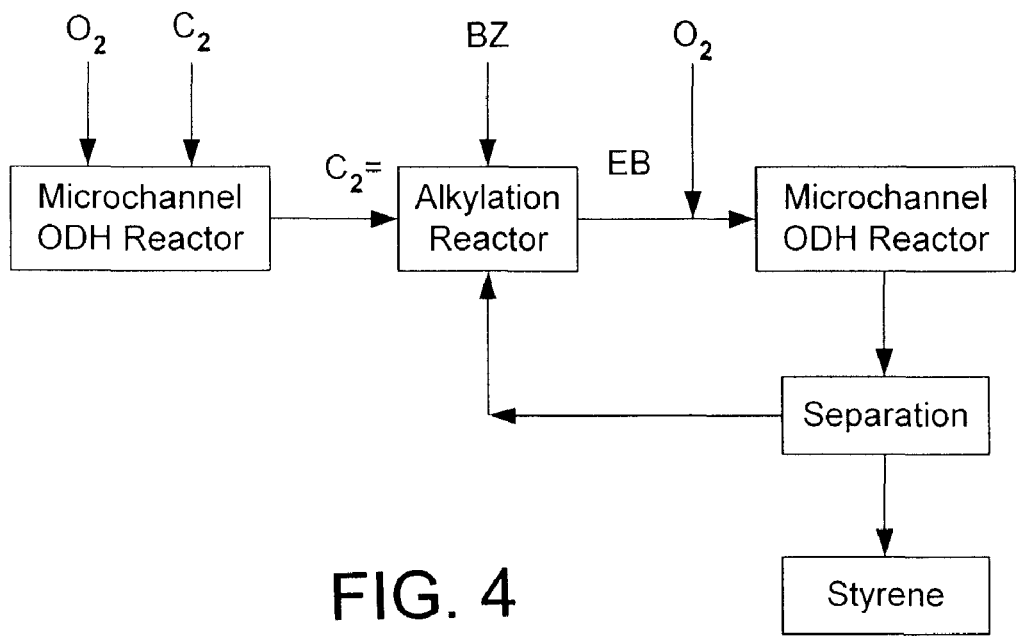
FIG. 4 is a flow sheet illustrating another alternate embodiment of a process for making styrene in accordance with the invention.

In the process illustrated in FIG. 4, ethane is oxidatively dehydrogenated in a first microchannel reactor to form ethylene. The ethylene is fed together with benzene to an alkylation reactor to form ethylbenzene. Ethylbenzene is then oxidatively dehydrogenated in a second microchannel reactor to form styrene. Styrene and ethylbenzene are separated and the unreacted ethylbenzene may be recycled.

Figure 5:
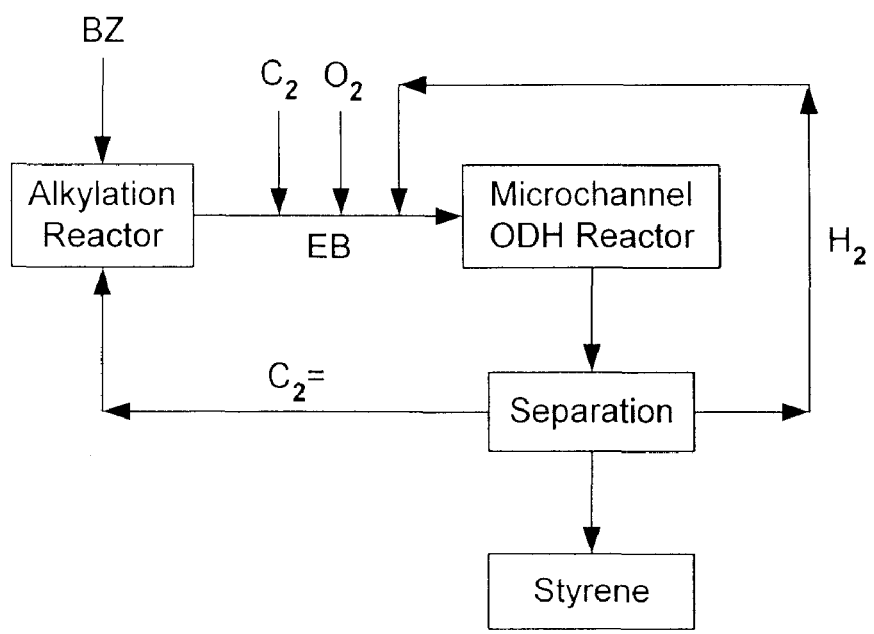
FIG. 5 is a flow sheet illustrating another alternate embodiment of a process for making styrene in accordance with the invention.

In the process illustrated in FIG. 5, benzene and recycled ethylene are fed to an alkylation reactor to produce ethylbenzene. Ethane, ethylbenzene, oxygen and recouped hydrogen are fed to a microchannel reactor to be simultaneously oxidatively dehydrogenated to for styrene. Styrene, unreacted ethylene and hydrogen are separated. The ethylene may be recycled to the alkylation unit. The recouped hydrogen may be totally or partially co-fed to the microchannel oxidative dehydrogenation reactor.

Figure 6:
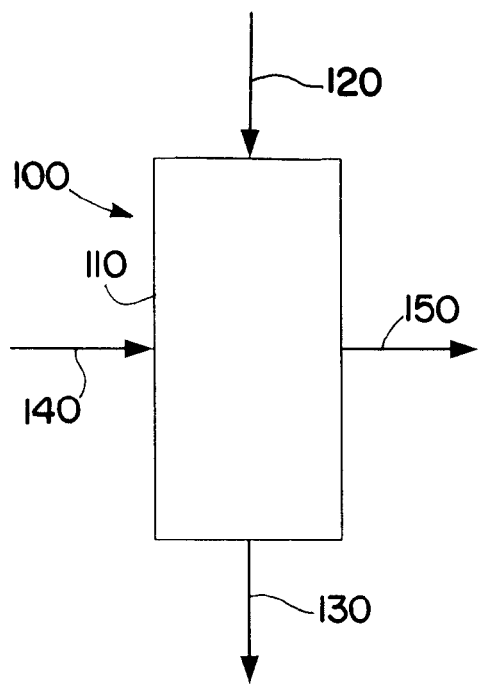
FIG. 6 is a schematic illustration of a microchannel reactor that may be used in accordance with the invention, the microchannel reactor comprising a plurality of repeating units comprising one or more process microchannels containing a catalyst, and heat exchange channels for exchanging heat with the process microchannels.

The following description of the microchannel reactor used to make styrene in accordance with the inventive process is also applicable to the microchannel reactors used upstream for making ethylene and ethylbenzene. In one embodiment, the microchannel reactor may be in the form illustrated in FIG. 6. Referring to FIG. 6, microchannel reactor 100 comprises microchannel reactor core 110, feed inlet 120, product outlet 130, heat exchange fluid inlet 140, and heat exchange fluid outlet 150. The microchannel reactor core 110 may comprise a plurality of repeating units, each of the repeating units comprising one or more process microchannels. The process microchannels may be operated in parallel in combination with a header or manifold assembly for providing for the flow of reactants into the process microchannels, and a footer or manifold assembly providing for the flow of product out of the process microchannels. The microchannel reactor core 110 may further comprise one or more heat exchange channels adjacent to and/or in thermal contact with the process microchannels. The heat exchange channels may be microchannels. When the reaction that is conducted in the process microchannels is an exothermic reaction, the heat exchange channels may be used to cool the process microchannels. When the reaction that is conducted in the process microchannels is an endothermic reaction, the heat exchange channels may be used to heat the process microchannels. The heat exchange change channels may be used to preheat one or more reactants and/or cool down the product. Various combinations of heating and/or cooling may be employed to provide for desired temperature profiles along the lengths of the process microchannels. Each of the process microchannels may contain a catalyst. The catalyst may be in any of the forms discussed below and is positioned in reaction zones in the process microchannels. In operation, a feed composition comprising ethylbenzene flows into the microchannel reactor core 110 as indicated by arrow 120. Optionally, oxygen may be combined with the feed composition when the reaction is an oxidative dehydrogenation reaction. When oxygen is employed in the reaction, the ethylbenzene and oxygen may be mixed upstream of the microchannel reactor 100, in the header or manifold assembly of the microchannel reactor core 110, or in the process microchannels within the microchannel reactor core 110. Within each process microchannel, the ethylbenzene and oxygen may be mixed with each other in a mixing zone upstream of the reaction zone or in the reaction zone. Part of the oxygen may be mixed with the ethylbenzene in a mixing zone upstream of the reaction zone, and part of the oxygen may be mixed with the ethylbenzene in the reaction zone. When the oxygen and ethylbenzene are mixed with each other in the process microchannels, the oxygen may enter the process microchannels as a staged addition feed stream. The ethylbenzene, or the ethylbenzene in combination with oxygen, may undergo reaction in the process microchannels to form a product comprising styrene. The product flows through the footer or manifold assembly in the microchannel reactor core 110 and out of the microchannel reactor core 110 as indicated by arrow 130. Heat exchange fluid enters the microchannel reactor core 110 as indicated by arrow 140, circulates through heat exchange channels in the microchannel reactor core 110, heats or cools the process microchannels, and flows out of the microchannel reactor core 110 as indicated by arrow 150.

Figure 46:
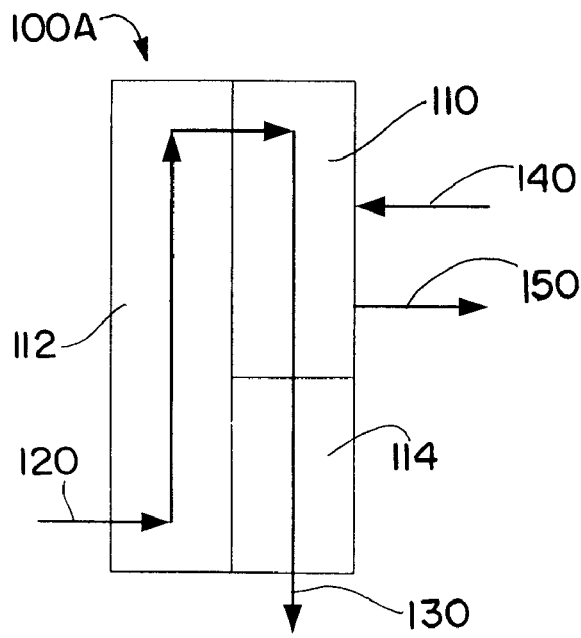
FIG. 46 is a schematic illustration of a microchannel reactor that may be used in accordance with the inventive process, the microchannel reactor being used in combination with an adjacent preheat section and a downstream cool down section.
Figure 47:
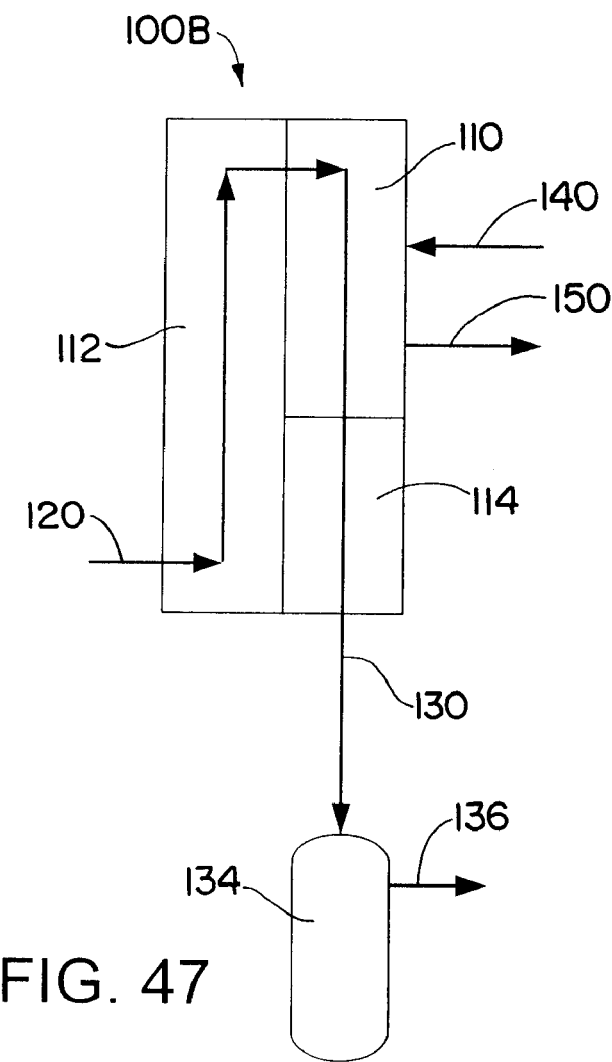
FIG. 47 is a schematic illustration that is identical to FIG. 46 with the exception that a styrene knockout drum for collecting styrene is provided downstream of the cool-down section.

The microchannel reactor core 110 may be positioned adjacent to or in thermal contact with a preheat section and/or upstream from a cool down section. The preheat section may be positioned adjacent to or in thermal contact with the cool down section. The preheat section and cool down section may each comprise a plurality of process microchannels that are the same as or similar to the process microchannels in the microchannel core 110 except that the process microchannels in the preheat and cool down sections do not contain catalyst. This is illustrated in FIGS. 46 and 47. Referring to FIG. 46, microchannel reactor 100A is the same as microchannel reactor 100 illustrated in FIG. 6 except that the microchannel reactor 100A further comprises preheat section 112 and cool down section 114. The microchannel reactor core 110 may be operated at a temperature in the range from about 220° C. to about 850° C., and in one embodiment about 300° C. to about 550° C. for a dehydrogenation process. For an oxidative dehydrogenation process the microchannel core 110 may be operated at a temperature in the range from about 300° C. to about 550° C., and in one embodiment from about 350° C. to about 500° C. Heat from the microchannel reactor core 110 may be used to heat reactants flowing into the microchannel reactor core 110 through preheat section 112. The reactants may be heated in the preheat section 112 from room temperature or ambient temperature up to the temperature in the microchannel reactor core 110. In one embodiment, the reactants may be heated in the preheat section 112 from room temperature or ambient temperature to a temperature in the range from about 50° C. to about 500° C., and in one embodiment in the range from about 150° C. to about 400° C. Similarly, the relatively cool reactants entering the preheat section 112, as indicated by arrow 120, may be used to cool the relatively hot product flowing out of the microchannel reactor core 110 through the cool-down section 114, as indicated by arrow 130. In the cool down section 114 the product may be cooled to a temperature in the range from about 550° C. to about 250° C., and in one embodiment from about 450° C. to about 300° C. Additional cooling may be employed in the cool down using a relatively cool heat exchange fluid flowing in heat exchange channels, which may be microchannels, in the cool down section 114. This process may be conducted in an apparatus having a box-like construction wherein the microchannel reactor and cool-down sections 114 are adjacent to the preheat section 112 as illustrated in FIG. 46.

The process illustrated in FIG. 47 is the same as the process illustrated in FIG. 46 with the exception that the microchannel reactor 100B illustrated in FIG. 47 also includes styrene knockout drum 134 which cools the product flowing from the cool-down section 114 as indicated by arrow 130. The temperature of the product stream entering the styrene knockout drum 134 may be in the range from about 350° C. to about 50° C., and in one embodiment about 250° C. The product flowing out of the styrene knockout drum 134 may be at a temperature in the range from about 100° C. to about −20° C., and in one embodiment about 5° C. The residence time of the product in the styrene knockout drum 134 may be in the range from about 0.01 to about 1000 seconds, and in one embodiment from about 10 to about 100 seconds. The product stream flows out of the knockout drum as indicated by arrow 136. The knockout drums 134 may be in the form of any vessel or container suitable for receiving the product flowing out of the cool down section 114. The internal volume of the knockout drum 134 may be relatively large compared to the internal volume of the process microchannels in the microchannel reactor core 110. For example, the internal volume of the knockout drum 134 may be up to about 10000 times the internal volume of the process microchannels, and in one embodiment from about 4 to about 10000 times the internal volume of the process microchannels in the microchannel reactor core 110. The knockout drum 134 may be useful in preventing or reducing the tendency of the product styrene to polymerize.

Figure 7:
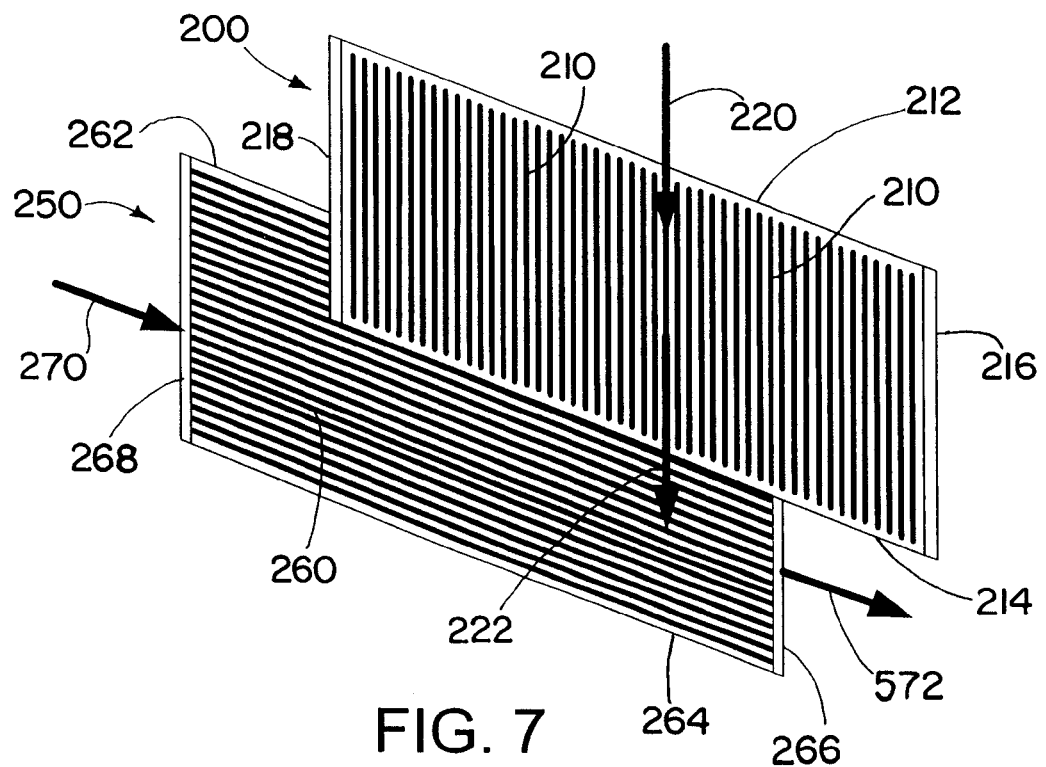
FIG. 7 is a schematic illustration of a layer of process microchannels and a layer of heat exchange channels that may be used in the microchannel reactor illustrated in FIG. 6. Each of the process microchannels may contain a catalyst.

In one embodiment, the microchannel reactor core 110 may contain layers 200 of process microchannels and layers 250 of heat exchange channels (e.g., microchannels) aligned side by side as illustrated in FIG. 7. Alternately, the layers 200 and 250 may be stacked one above the other. For each heat exchange layer 250, one or more process microchannel layers 200 may be used. Thus, for example, two, three, four, five, six or more process microchannel layers 200 may be employed with a single heat exchange layer 250. Alternatively, two or more heat exchange layers 250 may be employed with each process microchannel layer 200. Process microchannel layer 200 comprises a plurality of process microchannels 210 which provide for the flow of process fluid. Heat exchange microchannel layer 250 comprises a plurality of heat exchange microchannels 260 which provide for the flow of heat exchange fluid. The heat exchange layers 250 may be used for heating or cooling. In one embodiment, each process microchannel layer 200 may be positioned between adjacent heat exchange microchannel layers 250 on each side of the process microchannel layer 200. In one embodiment, two or more process microchannel layers 200 may be positioned adjacent to each other to form a vertically or horizontally oriented stack of process microchannel layers, and a heat exchange layer 250 may be positioned on one or both sides of the stack. In various embodiments of the invention, layers of staged addition channels, which may be microchannels, may be used in combination with the process microchannels, and for these embodiments one or more layers of the staged addition channels may be positioned adjacent to each of the process microchannel layers. Each combination of one or more process microchannel layers 200, heat exchange channel layers 250 and optional staged addition channels layers may be referred to as a repeating unit.

The process microchannels 210 in process microchannel layer 200 may be aligned in parallel. Each process microchannel 210 may extend along the length of microchannel layer 200 from end 212 to end 214. The process microchannels 210 may extend along the width of the process microchannel layer 200 from end 216 to end 218. The catalyst may be positioned in the process microchannels 210. The flow of process fluid through the process microchannels 210 may be in the direction indicated by arrows 220 and 222. The staged addition channels, when used, may be configured in the same way as the process microchannels 210 except that the staged addition channels do not contain a catalyst. For each process microchannel 210, one or more adjacent staged addition channels may be used. The process microchannels and staged addition channels may have at least one common wall with an opening to permit flow of fluid from the staged addition channel into the process microchannel at various or numerous points along the length of the process microchannel.

The heat exchange microchannels 260 may be aligned in parallel in heat exchange microchannel layer 250. Each heat exchange microchannel 260 may extend along the width of microchannel layer 250 from end 266 to end 268. The heat exchange microchannels 260 may extend along the length of microchannel layer 250 from end 262 to end 264 of microchannel layer 250. The heat exchange fluid may flow through the heat exchange microchannels 260 in the direction indicated by arrows 270 and 272. The flow of heat exchange fluid in the direction indicated by arrows 270 and 272 may be cross-current to the flow of process fluid flowing through process microchannels 210, as indicated by arrows 220 and 222. Alternatively, the heat exchange microchannels 260 may be oriented to provide for flow of the heat exchange fluid along the length of the microchannel layer 250 from end 262 to end 264 or from end 264 to end 262. This would result in the flow of heat exchange fluid in a direction that would be cocurrent or counter-current to the flow of process fluid through the process microchannels 210.

The number of microchannels 210 and 260 in each of the microchannel layers 200 and 250, as well as the number of channels in the optional staged addition layers, may be any desired number, for example, one, two, three, four, five, six, eight, ten, hundreds, thousands, tens of thousands, hundreds of thousands, millions, etc. The number of repeating units containing process microchannel layers, heat exchange channel layers and optionally staged addition channel layers that may be used in the microchannel reactor core 110 may be any number, for example, one, two, three, four, five, six, eight, ten, hundreds, thousands, etc.

Figure 8:
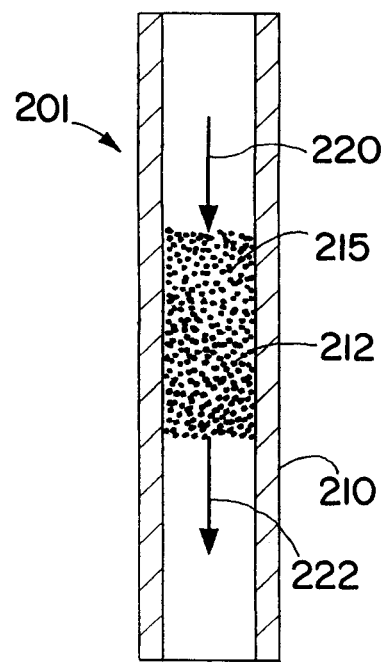
FIG. 8 is a schematic illustration of a repeating unit comprising a process microchannel that may be used in the microchannel reactor illustrated in FIG. 6. The process microchannel contains a reaction zone comprising a catalyst. The catalyst illustrated in FIG. 8 is in the form of a bed of particulate solids. However, any of the catalyst forms discussed in the specification may be used in the process microchannel illustrated in FIG. 8.

A number of repeating units that may be used in the microchannel reactor core 110 are illustrated in FIGS. 8-12. The microchannel reactor core 110 may contain any number of these repeating units, for example, one, two, three, four, five, six, eight, ten, hundreds, thousands, etc. The repeating unit 201 illustrated in FIG. 8 comprises process microchannel 210 which includes reaction zone 212 wherein catalyst 215 is situated. The catalyst 215 illustrated in FIG. 8 is in the form of a bed of particulate solids. However, any of the catalyst forms discussed in the specification may be used in the process microchannel illustrated in FIG. 8. One or more heat exchange channels may be positioned adjacent to one or both sides of the process microchannel 210. Alternatively, one or more heat exchange channels may be positioned remotely from, but in thermal contact with, the process microchannel 210.

Figure 9:
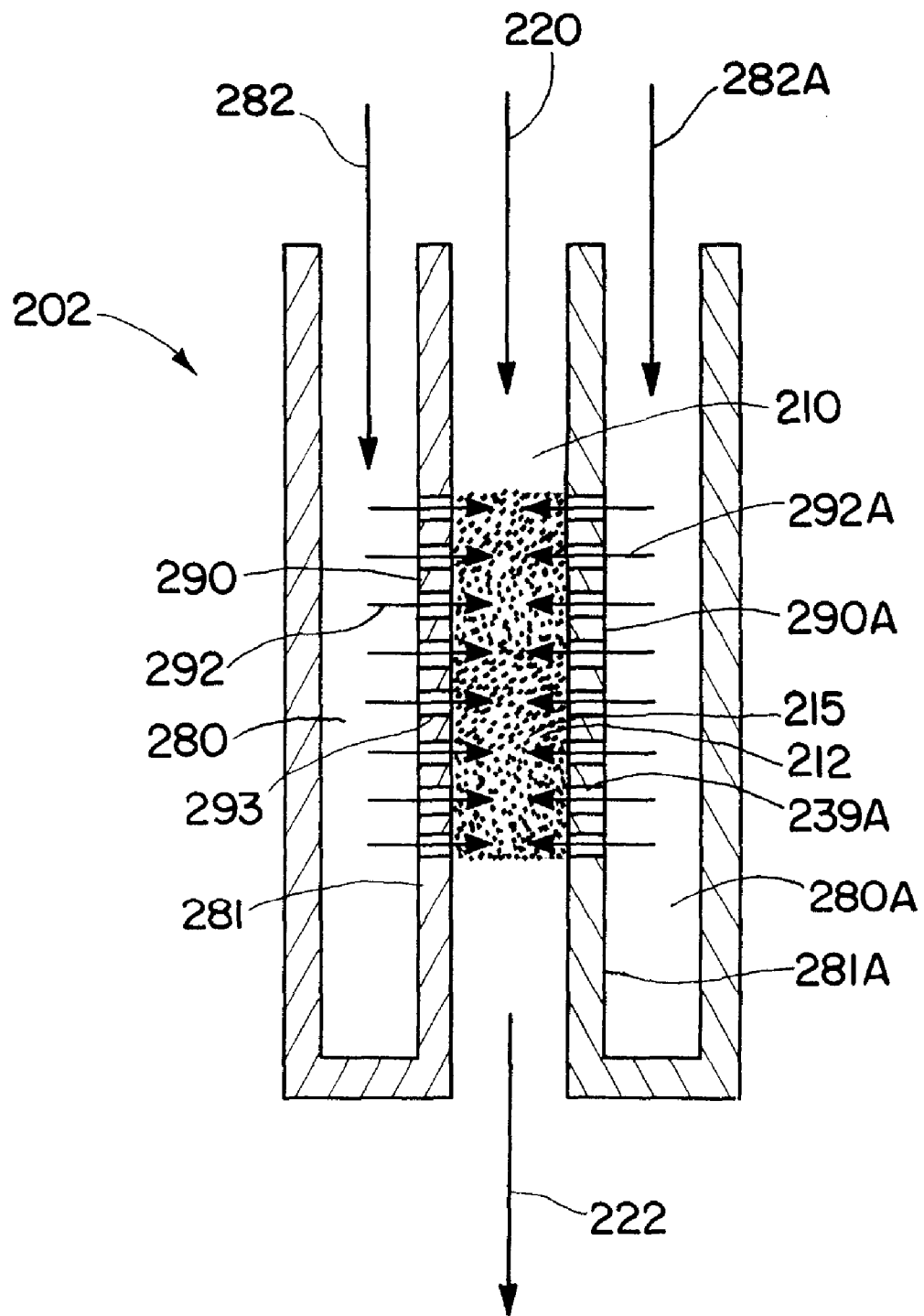
FIG. 9 is a schematic illustration of an alternate embodiment of a repeating unit that may be used in the microchannel reactor illustrated in FIG. 6. This repeating unit comprises a process microchannel and two adjacent staged addition channels. Each of the staged addition channels has a common wall with the process microchannel and an apertured section positioned in each of the common walls. The process microchannel contains a reaction zone comprising a catalyst. The catalyst illustrated in FIG. 9 is in the form of particulate solids. However, a catalyst having any of the forms discussed in the specification may be used in the reaction zone. This repeating unit may be used for oxidative dehydrogenation processes wherein a staged addition feed stream comprising oxygen flows from the staged addition channel through the apertured section into the process microchannel where it contacts and mixes with a feed composition comprising ethylbenzene and reacts to form styrene.

The repeating unit 202 illustrated in FIG. 9 comprises process microchannel 210 and adjacent staged addition channels 280 and 280A. The staged addition channels may be microchannels although alternatively they may be larger channels. Each of the staged addition channels 280 and 280A has a common wall 281 and 281A with the process microchannel 210 and an apertured section 290 and 290A positioned in each of the common walls 281 and 281A. Each of the apertured sections 290 and 290A contain a plurality of apertures 293 and 293A for permitting the flow of the staged addition feed stream through the apertured sections. The process microchannel 210 contains a reaction zone 212 wherein catalyst 215 is situated. The catalyst illustrated in FIG. 9 is in the form of particulate solids. However, a catalyst having any of the forms discussed in the specification may be used in the reaction zone.

Figure 10:
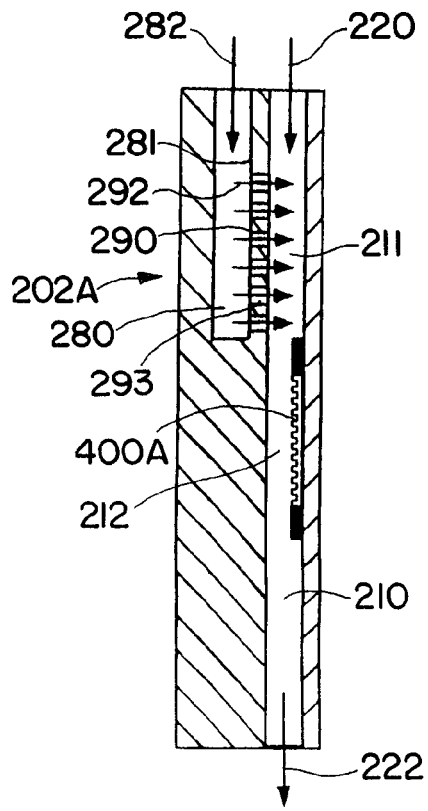
FIG. 10 is a schematic illustration of another alternate embodiment of a repeating unit that may be used in the microchannel reactor illustrated in FIG. 6. The repeating unit comprises a process microchannel which contains a reaction zone. A catalyst is positioned in the reaction zone. The repeating unit also includes a staged addition channel adjacent to the process microchannel and an apertured section positioned between the process microchannel and the staged addition channel. This repeating unit may be used for oxidative dehydrogenation processes wherein a staged addition feed stream comprising oxygen flows from the staged addition channel through the apertured section into the process microchannel where it contacts and mixes with a feed composition comprising ethylbenzene and reacts to form styrene. The staged addition feed stream and the feed composition contact each other in a mixing zone upstream of the reaction zone.

Repeating unit 202A, which may be used in the microchannel reactor core 110, is illustrated in FIG. 10. Repeating unit 202A comprises process microchannel 210, staged addition channel 280, and apertured section 290. A common wall 281 separates process microchannel 210 and staged addition channel 280. The apertured section 290 is positioned in common wall 281. The apertured section 290 contains a plurality of apertures 293 for permitting the flow of staged addition feed stream through the apertured section. The process microchannel 210 has a mixing zone 211, and a reaction zone 212. Microgrooved support strip 400A, which supports a catalyst, is positioned in the reaction zone 212. The support strip 400A is described below. The mixing zone 211 is upstream from the reaction zone 212. A feed composition comprising ethylbenzene flows into process microchannel 210, as indicated by the arrow 220, and into the mixing zone 211. A staged addition feed stream comprising oxygen flows into staged addition channel 280, as indicated by arrow 282, and from the staged addition channel 280 through the apertured section 290 into mixing zone 211, as indicated by arrows 292. The direction of flow of the staged addition feed stream in the staged addition channel 280, as indicated by arrow 282, is cocurrent with the direction of flow of the feed composition in the process microchannel 210, as indicated by arrow 220. Alternatively, the flow of staged addition feed stream in the staged addition channel 280 may be counter-current or cross-current relative to the flow of the feed composition in the process microchannel 210. The feed composition and staged addition contact each other in the mixing zone 211 and form a reactant mixture. The reactant mixture flows from the mixing zone 211 into the reaction zone 212, contacts the catalyst, and reacts to form the product comprising styrene. The product exits the process microchannel 210, as indicated by arrow 222. A heat exchange channel may be positioned adjacent to the staged addition channel 280 or the process microchannel 210. Alternatively, one or more heat exchange channels may be positioned remotely from, but in thermal contact with, the staged addition channel 280 and/or the process microchannel 210. In either case the heat exchange channels may exchange heat with the process fluids in the staged addition channel 280 and the process microchannel 210.

In an alternate embodiment of the repeating unit 202 illustrated in FIG. 10, a supplemental mixing zone may be provided in the process microchannel 210 between the mixing zone 211 and the reaction zone 212.

Figure 11:
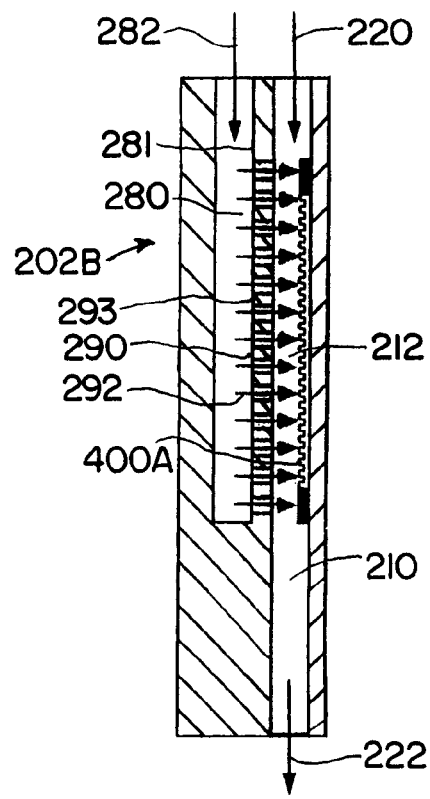
FIG. 11 is a schematic illustration of an alternate embodiment of the repeating unit illustrated in FIG. 10 wherein the staged addition feed stream and the feed composition contact and mix with each other in the reaction zone.

The repeating unit 202B illustrated in FIG. 11 is identical to the repeating unit 202A illustrated in FIG. 10 with the exception that the repeating unit 202B does not contain the separate mixing zone 211. With repeating unit 202B, the staged addition feed stream flows through the apertured section 290 into the reaction zone 212 where it contacts the feed composition and reacts in the presence of the catalyst to form the product comprising styrene. The product then flows out of the process microchannel 210, as indicated by arrow 222.

Figure 12:
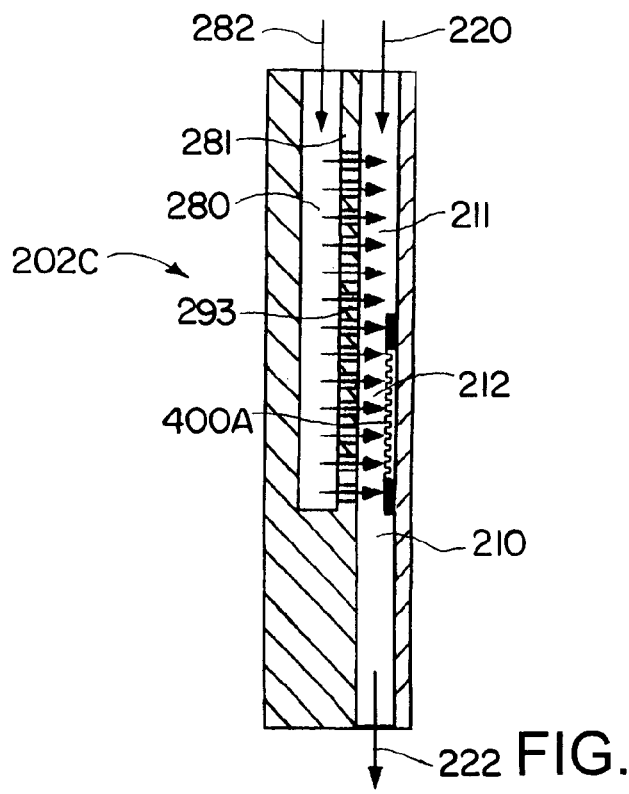
FIG. 12 is a schematic illustration of another alternate embodiment of the repeating unit illustrated in FIG. 10 wherein part of the staged addition feed stream contacts and mixes with the feed composition in a mixing zone upstream of a reaction zone, and part of the staged feed stream contacts and mixes with the feed composition in the reaction zone.

The repeating unit 202C illustrated in FIG. 12 is identical to the repeating unit 202A illustrated in FIG. 10 with the exception that part of the staged addition feed stream mixes with the feed composition in the mixing zone 211, and part of the staged addition feed stream mixes with the feed composition in the reaction zone 212. The amount of the staged addition feed stream that mixes with the feed composition in the mixing zone 211 may be from about 1% to about 99% by volume of the staged addition feed stream, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume of the staged addition feed stream. The remainder of the staged addition feed stream mixes with the feed composition in the reaction zone 212.

The apertures 293 and 293A may be of sufficient size to permit the flow of the staged addition feed stream through the apertured sections 290 and 290A, respectively. The apertures may be referred to as pores. The apertured sections 290 and 290A containing the foregoing apertures may have thicknesses in the range from about 0.01 to about 50 mm, and in one embodiment about 0.05 to about 10 mm, and in one embodiment about 0.1 to about 2 mm. The apertures may have average diameters in the range up to about 250 microns, and in one embodiment up to about 100 microns, and in one embodiment up to about 50 microns, and in one embodiment in the range from about 0.001 to about 50 microns, and in one embodiment from about 0.05 to about 50 microns, and in one embodiment from about 0.1 to about 50 microns. In one embodiment, the apertures may have average diameters in the range from about 0.5 to about 10 nanometers (nm), and in one embodiment about 1 to about 10 nm, and in one embodiment about 5 to about 10 nm. The number of apertures in the apertured sections may be in the range from about 1 to about $5 \times 10^8$ apertures per square centimeter, and in one embodiment about 1 to about $1 \times 10^6$ apertures per square centimeter. The apertures may or may not be isolated from each other. A portion or all of the apertures may be in fluid communication with other apertures within the apertured section. That is, a fluid may flow from one aperture to another aperture. The ratio of the thickness of the apertured sections 290 and 290A to the length of the apertured sections along the flow path of the fluids flowing through the process microchannels 210 may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1.

In one embodiment, the apertured sections 290 and 290A may comprise an interior portion that forms part of one or more of the interior walls of each process microchannel 210. A surface feature sheet may overlie this interior portion of the apertured section. Surface features may be formed in and/or on the surface feature sheet. The staged addition feed stream may flow through the apertured section and the surface feature sheet into the process microchannel. Part of the staged addition feed stream may be detached from the surface of the surface feature sheet while part may flow within the surface features of the surface feature sheet. The surface feature sheet may contain angled surface features that have relatively small widths or spans relative to the overall flow length. The surface feature sheet may provide mechanical support for the apertured section. The surface features may impart a vortical flow pattern to the staged addition feed stream. The vortical flow pattern may impart shear to the staged addition feed stream flowing through the apertured section and thus reduce the size of the staged addition feed stream bubbles or droplets in the bulk flow path.

Figure 13:
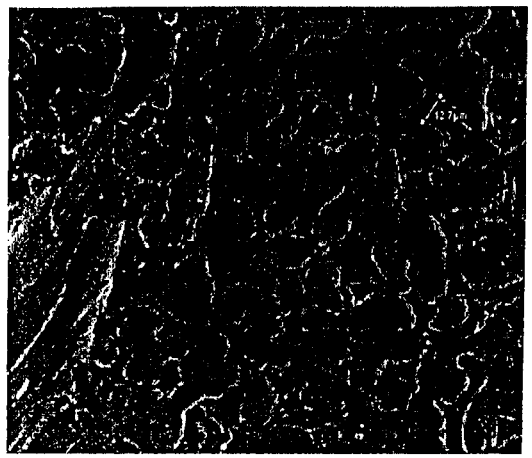
FIG. 13 is a scanning electron microscopic (SEM) image of a porous stainless steel substrate before being heat treated. This substrate may be used for making an apertured section for a process microchannel used with the inventive process.
Figure 14:
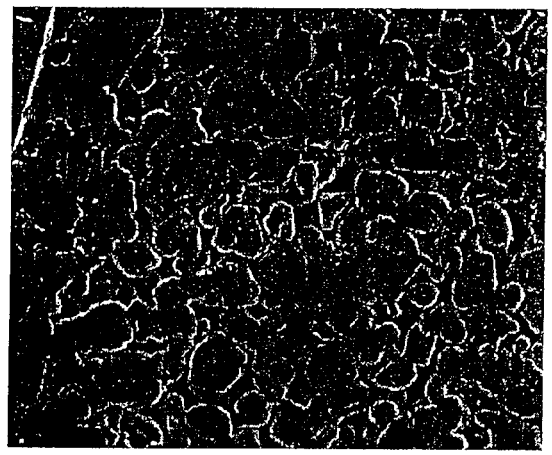
FIG. 14 is an SEM image of the substrate illustrated in FIG. 13 after being heat treated. This substrate may be used for making an apertured section for a process microchannel used with the inventive process.

The apertured sections 290 and 290A may be constructed of any material that provides sufficient strength and dimensional stability to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The apertures may be formed using known techniques such as laser drilling, microelectro machining system (MEMS), lithography electrodeposition and molding (LIGA), electrical sparkling, photochemical machining (PCM), electrochemical machining (ECM), electrochemical etching, and the like. The apertures may be formed using techniques used for making structured plastics, such as extrusion, or membranes, such as aligned carbon nanotube (CNT) membranes. The apertures may be formed using techniques such as sintering or compressing metallic powder or particles to form tortuous interconnected capillary channels and the techniques of membrane fabrication. The apertures may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The apertures may be reduced in size by heat treating as well as by methods that form an oxide scale or coating on the internal side walls of the apertures. These techniques may be used to partially occlude the apertures to reduce the size of the openings for flow. FIGS. 13 and 14 show a comparison of SEM surface structures of a stainless steel porous substrate before and after heat treatment at the same magnification and the same location. FIG. 13 shows the surface before heat treating and FIG. 14 shows the surface after heat treating. The surface of the porous material after the heat treatment has a significantly smaller gap and opening size. The average distance between the openings is correspondingly increased.

Figure 15:
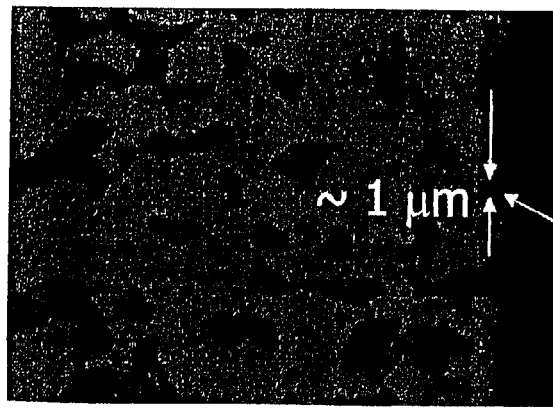
FIG. 15 is an SEM image of a tailored porous substrate which may be used for making an apertured section for a process microchannel used with the inventive process.
Figure 16:
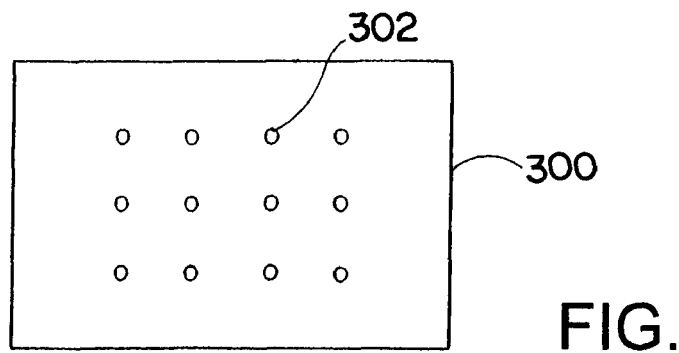
FIG. 16 is a plan view of an apertured sheet which may be used in making an apertured section for a process microchannel used with the inventive process.
Figure 17:
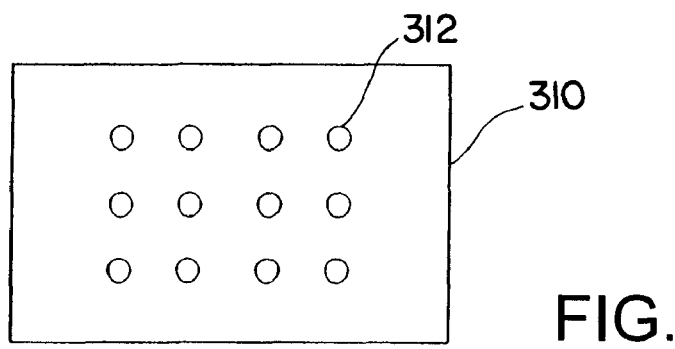
FIG. 17 is a plan view of an apertured sheet or plate which may be used in making an apertured section for a process microchannel used with the inventive process.

The apertured sections 290 and 290A may be made from a metallic or nonmetallic porous material having interconnected channels or pores of an average pore size in the range from about 0.01 to about 1000 microns, and in one embodiment in the range from about 0.01 to about 200 microns. These pores may function as the apertures 293 and 293A. The porous material may be made from powder or particulates so that the average inter-pore distance is similar to the average pore size. The porous material may be tailored by oxidization at a high temperature in the range from about 300° C. to about 1000° C. for a duration of about 1 hour to about 20 days, or by coating a thin layer of another material such as alumina by sol coating or nickel using chemical vapor deposition over the surface and the inside of pores to block the smaller pores, decrease pore size of larger pores, and in turn increase the inter-pore distance. An SEM image of a tailored substrate or apertured section is shown in FIG. 15.

The making of substrates for use as apertured sections 290 and 290A with sufficiently small micro-scale apertures or pores 293 and 293A to provide a staged addition feed stream having bubble or droplet sizes smaller than about one micron can be problematic. One of the reasons for this lies in the fact that relatively high surface roughness occurs with untreated regular porous materials such as a metallic porous substrates made from powder/particles by compression and/or sintering. These metallic porous substrates typically do not have the required pore size in the surface region when a given nominal pore size is lower than a certain value. While the bulk of the porous material may have the specified nominal pore size, the surface region is often characterized by merged pores and cavities of much larger sizes. This problem can be overcome by tailoring these substrates to provide for the desired pore size and inter-pore distance in the surface region. This may be done by removing a surface layer from the porous substrate and adding a smooth new surface with smaller openings. The droplet size or bubble size of staged addition feed stream that may be formed using these tailored substrates may be reduced without increasing the pressure drop across the substrate. Since direct grinding or machining of the porous surface may cause smearing of the surface structure and blockage of the pores, the porous structure may be filled with a liquid filler, followed by solidification and mechanical grinding/polishing. The filler is then removed to regain the porous structure of the material. The filler may be a metal with a low melting point such as zinc or tin or the precursor of a polymer such as an epoxy. The liquid filling and removing steps may be assisted by the use of a vacuum. Grinding/polishing may be effected using a grinding machine and a grinding powder. Metal filler removal may be effected by melting and vacuum suction, or by acid etching. Epoxies or other polymers may be removed by solvent dissolution or by burn-off in air.

Referring to FIGS. 16-19, the apertured sections 290 and 290A, in one embodiment, may be constructed of a relatively thin sheet 300 containing relatively small apertures 302, and a relatively thick sheet or plate 310 containing relatively large apertures 312. The apertures 312 may be aligned with or connected to the apertures 302. The relatively thin sheet 300 overlies and is bonded to the relatively thick sheet or plate 310, the relatively thin sheet 300 facing the interior of process microchannel 210 and the relatively thick sheet 310 facing the interior of the staged addition channel 280 or 280A. The relatively thin sheet 300 may be bonded to the relatively thick sheet 310 using any suitable procedure (e.g., diffusion bonding) to provide a composite construction 320 with enhanced mechanical strength. The relatively thin sheet 300 may have a thickness in the range from about 0.001 to about 0.5 mm, and in one embodiment about 0.05 to about 0.2 mm. The relatively small apertures 302 may have any shape, for example, circular, triangular or rectangular. The relatively small apertures 302 may have an average diameter in the range from about 0.05 to about 50 microns, and in one embodiment about 0.05 to about 20 microns. The relatively thick sheet or plate 310 may have a thickness in the range from about 0.01 to about 5 mm, and in one embodiment about 0.1 to about 2 mm. The relatively large apertures 312 may have any shape, for example, circular, triangular or rectangular. The relatively large apertures 312 may have an average diameter in the range from about 0.01 to about 4000 microns, and in one embodiment about 1 to about 2000 microns, and in one embodiment about 10 to about 1000 micron. The total number of apertures 302 in sheet 300 and the total number of apertures 312 in sheet or plate 310 may be in the range from about 1 to about 10000 apertures per square centimeter, and in one embodiment from about 1 to about 1000 apertures per square centimeter. The sheet 300 and the sheet or plate 310 may be constructed of any of the materials described above as being useful for constructing the apertured sections 290 and 290A. The apertures 302 and 312 may be aligned or connected in such a manner that fluid flowing through the apertured sections 290 and 290A flows initially through the apertures 312 then through the apertures 302. The relatively short passageway for the fluid to flow through the relatively small apertures 302 enables the fluid to flow through the apertures 302 with a relatively low pressure drop as compared to the pressure drop that would occur if the passageway in the apertures had a depth equal to the combined depth of apertures 302 and 312

Figure 18:
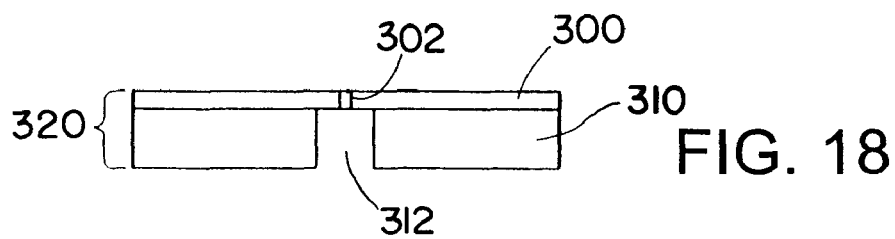
FIG. 18 is an illustration of a relatively thin apertured sheet overlying a relatively thick apertured sheet or plate which may be used in making an apertured section for a process microchannel used with the inventive process.
Figure 19:
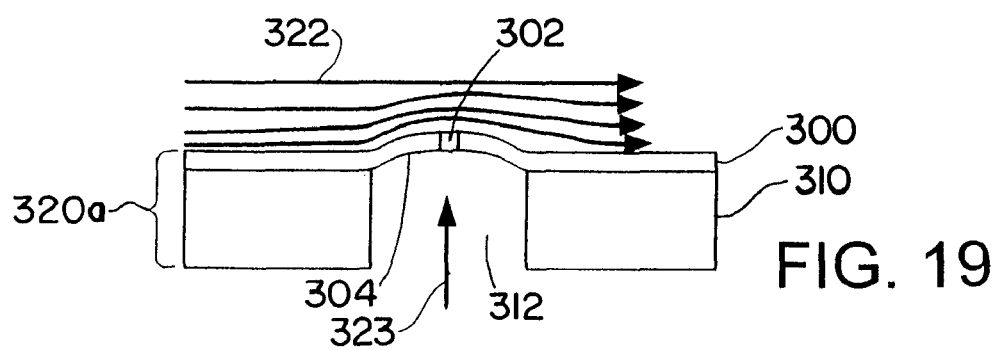
FIG. 19 is an illustration of a relatively thin apertured sheet overlying a relatively thick apertured sheet or plate which may be used in making an apertured section for a process microchannel used with the inventive process.

In the embodiment illustrated in FIG. 19, the composite construction 320a has the same design as illustrated in FIG. 18 with the exception that convex portion 304 of the relatively thin sheet 300 covering the aperture 312 is provided. Convex portion 304 provides increased local shear force in the adjacent channel. The staged addition feed stream flows through the apertures 312 and 302 in the direction indicated by arrow 323. The directional arrows 322 in FIG. 19 show the flow of the feed composition in the process microchannel adjacent to the aperture 302. The increased local shear force leads to a smaller droplet size or gas bubble for the fluid flowing through the aperture 302.

Figure 20:
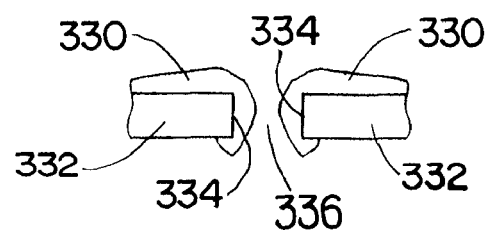
FIG. 20 is an illustration of an alternate embodiment of an aperture that may be used in the apertured section of a process microchannel used with the inventive process, the aperture having a coating partially filling it and overlying its sidewalls.

In the embodiment illustrated in FIG. 20, a surface coating 330 is deposited on the surface of sheet or plate 332 and on the internal sidewalls 334 of aperture 336. This coating provides a facilitated way of reducing the diameter of the apertures 293 and 293A. The coating material used to form coating 330 may be alumina, nickel, gold, or a polymeric material (e.g., Teflon). The coating 330 may be applied to the sheet or plate 332 using known techniques including chemical vapor deposition, metal sputtering, metal plating, sintering, sol coating, and the like. The diameter of the apertures may be controlled by controlling the thickness of the coating 330.

In one embodiment, the apertured sections 290 and 290A may be formed from an asymmetric porous material, for example, a porous material having multiple layers of sintered particles. The number of layers may be two, three, or more. An advantage of these multilayered substrates is that they provide enhanced durability and adhesion. Examples include sintered ceramics that have relatively large pores on one side and relatively small pores on the other side. The relatively small pores may have diameters in the range of about 2 to about 10 nm. The relatively small pores may be positioned in a relatively thin layer of the multilayered substrate. The relatively thin layer may have a thickness in the range of about 1 to about 10 microns. The side with the relatively small pores may be placed facing the interior of the process microchannel 210 to take advantage of relatively high shear forces to remove the relatively small droplets of reactant and/or liquid catalyst as they are formed.

During the inventive process the staged addition feed stream may flow through the apertured sections 290 and 290A into the process microchannel 210. In one embodiment, the apertured section may extend along at least about 5% of the axial length of the process microchannel, and in one embodiment at least about 20% of the axial length of the process microchannel, and in one embodiment at least about 35% of the axial length of the process microchannel, and in one embodiment at least about 50% of the axial length of the process microchannel, and in one embodiment at least about 65% of the axial length of the process microchannel, and in one embodiment at least about 80% of the axial length of the process microchannel, and in one embodiment at least about 95% of the axial length of the process microchannel, and in one embodiment from about 5% to about 100% of the axial length of the process microchannel, and in one embodiment from about 10% to about 95% of the axial length of the process microchannel, and in one embodiment from about 25% to about 75% of the axial length of the process microchannel, and in one embodiment from about 40% to about 60% of the axial length of the process microchannel.

The dehydrogenation catalyst may comprise at least one oxide of iron, chromium or a combination thereof. In one embodiment, the catalyst may comprise iron oxide and one or more of potassium oxide, molybdenum oxide, cerium oxide, and calcium carbonate. In one embodiment, the catalyst may comprise one or more Group VII nobel metals (e.g., platinum, iridium, rhodium, palladium). The catalytic metals may be combined with a carrier such as a refractory inorganic oxide. Alumina may be used as the carrier.

The oxidative dehydrogenation catalyst may comprise any vanadium-containing, molybdenum-containing or tungsten-containing oxidative dehydrogenation catalyst. Catalysts containing combinations of two or more of V, Mo and W may be used. The catalyst may comprise one or more of $V_2O_5$, $MoO_3$ or $WO_3$ catalysts. The catalyst may be supported. The support may comprise $Al_2O_3$, $MgO$, $MgAl_2O_4$, $CaO$, $TiO_2$, $ZrO_2$, $SiO_2$, $Ga_2O_3$, rare earth oxide, active carbon, carbon fibers, molecular sieves, or a combination of two or more thereof. The catalyst may comprise any vanadate, molybdate, tungstate, or a combination of two or more thereof. Examples may include $FeVO_4$, $CrVO_4$, $NaVO_3$, $BiVO_4$, $AlVO_4$, $CeVO_4$, $VOPO_4$, $LaVO_4$, $SmVO_4$, $NiMoO_4$, $MgMoO_4$, $CaMoO_4$, $FeMoO_4$, $Fe_2(MoO_4)_3$, $MgWO_4$, $CaWO_4$, $NiWO_4$, $FeWO_4$, or a combination of two or more thereof. The catalyst may be promoted by alkali, alkaline earth, rare earth, transition metal oxides, Group VB elements (P, As, Sb and Bi), or a combination of two or more thereof. The catalyst may be prepared by impregnation, sol-gel, co-precipitation, ion-exchange, solution evaporation or deposition-precipitation. The catalyst may be coated on a substrate. The substrate may have a flat surface or a structured surface. Examples of the substrates may include flat coupons, shims, honeycombs, gauze, foams, fins, felts, and/or surface-featured coupons. The materials of the substrates may be made of a material comprising metal, alloys, super alloys, ceramics, or a combination of two or more thereof. The metallic substrates may be heat treated prior to catalyst coating. The catalyst coating may be performed by slurry-coating, sol-coating or solution-coating.

The catalyst may have any size and geometric configuration that fits within the process microchannels. The catalyst may be in the form of particulate solids (e.g., pellets, powder, fibers, and the like) having a median particle diameter of about 1 to about 1000 microns, and in one embodiment about 10 to about 500 microns, and in one embodiment about 25 to about 250 microns.

The catalyst may comprise a graded catalyst.

The catalyst may be in the form of a mesoporous material wherein the average pore size may be at or above about 1 nanometer (nm), for example, in the range from about 1 to about 100 nm, and in one embodiment from about 1 to about 20 nm. In one embodiment, mesoporous catalysts may be surprisingly active and selective for forming styrene.

Figures 21, 22, 23:
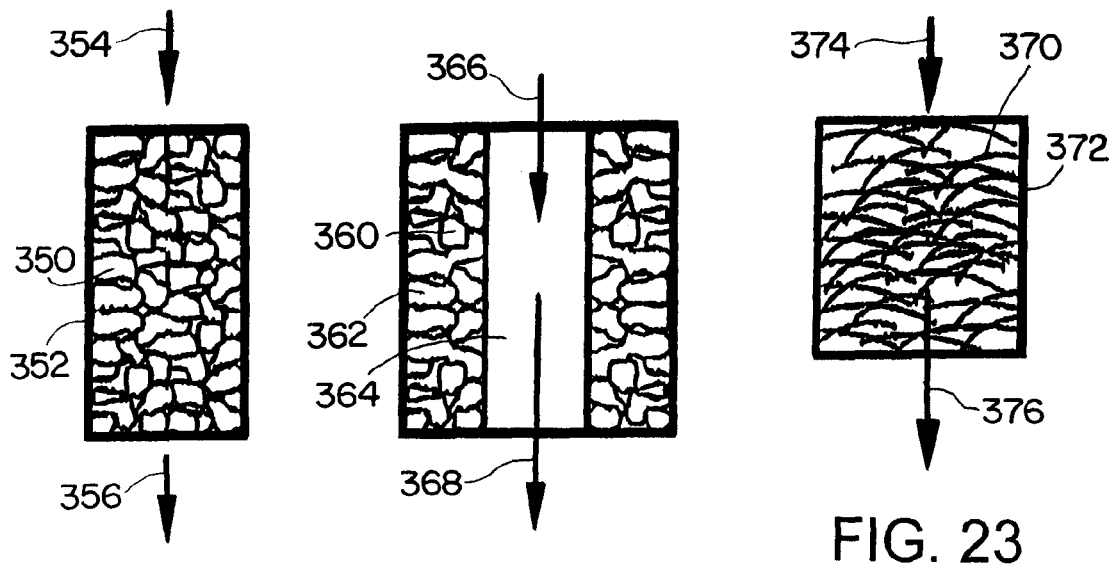
FIG. 21 is a schematic illustration of the reaction zone of a process microchannel that may be used with the inventive process, the reaction zone comprising a catalyst having a packed bed configuration.
FIG. 22 is a schematic illustration of the reaction zone of a process microchannel that may be used with the inventive process, the reaction zone comprising a catalyst having a flow-by configuration.
FIG. 23 is a schematic illustration of the reaction zone of a process microchannel that may be used with the inventive process, the reaction zone comprising a catalyst having a flow-through configuration.

The catalyst may be in the form of a fixed bed of particulate solids such as illustrated in FIG. 21. Referring to FIG. 21, the catalyst 350 is contained within process microchannel 352. The reactants flow through the catalyst bed as indicated by arrows 354 and 356.

The catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a support having a structure of tangled strands, like steel wool. The catalyst may be supported on a support having a honeycomb structure or a serpentine configuration.

The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 22. In FIG. 22 the catalyst 360 is contained within process microchannel 362. An open passage way 364 permits the flow of the reactants through the process microchannel 362 in contact with the catalyst 360 as indicated by arrows 366 and 368.

The catalyst may be supported on a flow-through support structure such as a foam, wad, pellet, powder, or gauze. An example of a flow-through structure is illustrated in FIG. 23. In FIG. 23, the flow-through catalyst 370 is contained within process microchannel 372 and the reactants flow through the catalyst 370 as indicated by arrows 374 and 376.

The support may be formed from a material comprising silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof. In one embodiment, the support structure may be made of a heat conducting material, such as a metal, to enhance the transfer of heat away from the catalyst.

The catalyst may be directly washcoated on the interior walls of the process microchannels, grown on the walls from solution, or coated in situ on a fin structure. The catalyst may be in the form of a single piece of porous contiguous material, or many pieces in physical contact. In one embodiment, the catalyst may comprise a contiguous material and have a contiguous porosity such that molecules can diffuse through the catalyst. In this embodiment, the fluids may flow through the catalyst rather than around it. In one embodiment, the cross-sectional area of the catalyst may occupy from about 1 to about 99%, and in one embodiment from about 10 to about 95% of the cross-sectional area of the process microchannels. The catalyst may have a surface area, as measured by BET, of greater than about 0.5 $m^2/g$, and in one embodiment greater than about 2 $m^2/g$, and in one embodiment greater than about 5 $m^2/g$, and in one embodiment greater than about 10 $m^2/g$, and in one embodiment greater than about 25 $m^2/g$, and in one embodiment greater than about 50 $m^2/g$.

The catalyst may comprise a porous support, an interfacial layer overlying the porous support, and a catalyst material dispersed or deposited on the interfacial layer. The interfacial layer may be solution deposited on the support or it may be deposited by chemical vapor deposition or physical vapor deposition. In one embodiment the catalyst comprises a porous support, optionally a buffer layer overlying the support, an interfacial layer overlying the support or the optional buffer layer, and a catalyst material dispersed or deposited on the interfacial layer. Any of the foregoing layers may be continuous or discontinuous as in the form of spots or dots, or in the form of a layer with gaps or holes.

The porous support may have a porosity of at least about 5% as measured by mercury porosimetry and an average pore size (sum of pore diameters divided by number of pores) of about 1 to about 1000 microns. The porous support may be made of any of the above indicated materials identified as being useful in making a support structure. The porous support may comprise a porous ceramic support or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. $\alpha$-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 µm, and in one embodiment about 0.05 to about 5 µm.

In one embodiment of the invention, adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $\gamma$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 µm, and in one embodiment from about 1 to about 50 µm. The interfacial layer may be either crystalline or amorphous. The interfacial layer may have a BET surface area of at least about 1 m²/g.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

Figure 24:
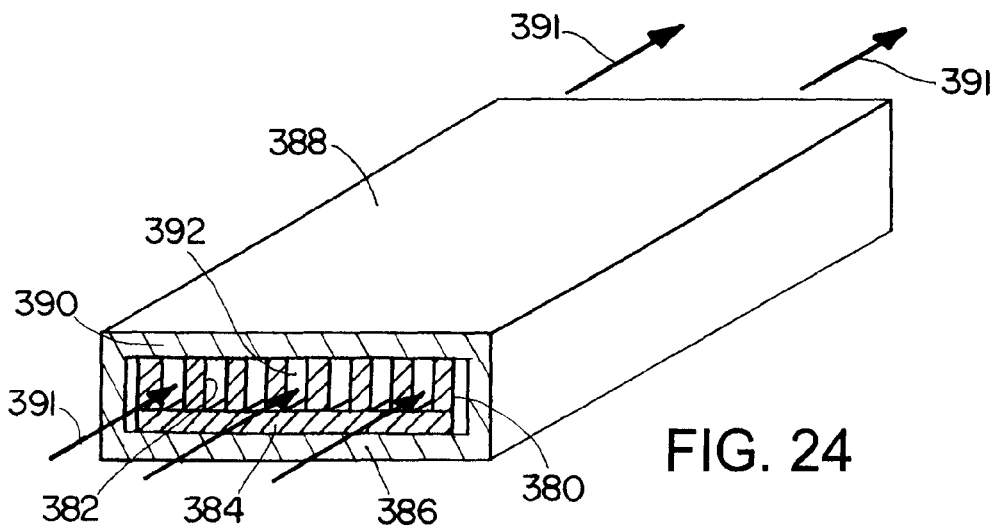
FIG. 24 is a schematic illustration of a process microchannel that may be used in the inventive process, the process microchannel containing a fin assembly comprising a plurality of fins, a catalyst being supported by the fins.
Figures 25, 26:
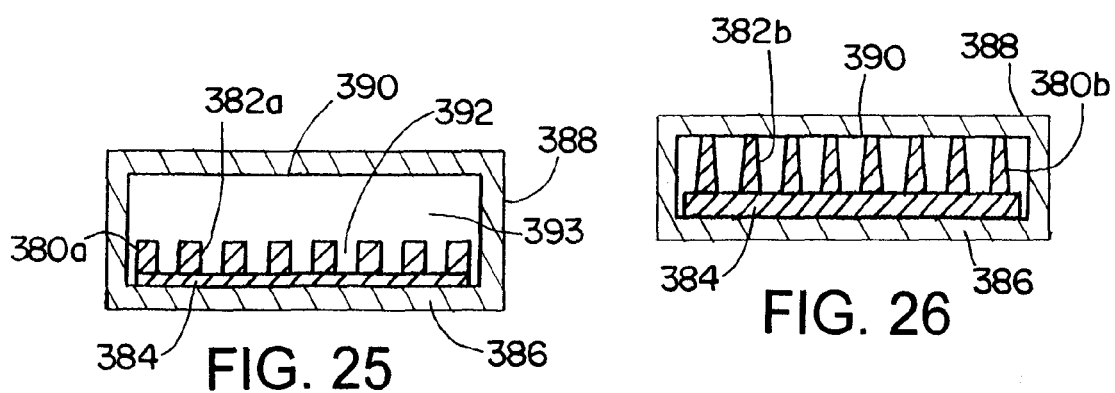
FIG. 25 is a schematic illustration of an alternate embodiment of the process microchannel and fin assembly illustrated in FIG. 24.
FIG. 26 is a schematic illustration of an another alternate embodiment of the process microchannel and fin assembly illustrated in FIG. 24.

The catalyst may be supported on an assembly of one or more fins positioned within the process microchannels. Examples are illustrated in FIGS. 24-26. Referring to FIG. 24, fin assembly 380 includes fins 382 which are mounted on fin support 384 which overlies base wall 386 of process microchannel 388. The fins 382 project from the fin support 384 into the interior of the process microchannel 388. The fins 382 extend to the interior surface of upper wall 390 of process microchannel 388. Fin channels 392 between the fins 392 provide passage ways for fluid to flow through the process microchannel 388 parallel to its length. Each of the fins 382 has an exterior surface on each of its sides, this exterior surface provides a support base for the catalyst. With the inventive process, the reactants flow through the fin channels 392, contact the catalyst supported on the exterior surface of the fins 382, and react to form the product. The fin assembly 380a illustrated in FIG. 25 is similar to the fin assembly 380 illustrated in FIG. 24 except that the fins 382a do not extend all the way to the interior surface of the upper wall 390 of the microchannel 388. The fin assembly 380b illustrated in FIG. 26 is similar to the fin assembly 380 illustrated in FIG. 24 except that the fins 382b in the fin assembly 380b have cross sectional shapes in the form of trapezoids. Each of the fins (382, 382a, 382b) may have a height ranging from about 0.02 mm up to the height of the process microchannel 838, and in one embodiment from about 0.02 to about 10 mm, and in one embodiment from about 0.02 to about 5 mm, and in one embodiment from about 0.02 to about 2 mm. The width of each fin (382, 382a, 382b) may range from about 0.02 to about 5 mm, and in one embodiment from about 0.02 to about 2 mm and in one embodiment about 0.02 to about 1 mm. The length of each fin (382, 382a, 382b) may be of any length up to the length of the process microchannel 838, and in one embodiment up to about 10 m, and in one embodiment about 1 cm to about 10 m, and in one embodiment about 1 cm to about 5 m, and in one embodiment about 1 cm to about 2.5 m. The gap between each of the fins (382, 382a, 382b) may be of any value and may range from about 0.02 to about 5 mm, and in one embodiment from about 0.02 to about 2 mm, and in one embodiment from about 0.02 to about 1 mm. The number of fins (382, 382a, 382b) in the process microchannel 388 may range from about 1 to about 50 fins per centimeter of width of the process microchannel 388, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. As indicated above, each of the fins may have a cross-section in the form of a rectangle or square as illustrated in FIG. 24 or 25, or a trapezoid as illustrated in FIG. 26. When viewed along its length, each fin (382, 382a, 382b) may be straight, tapered or have a serpentine configuration. The fin assembly (380, 380a, 380b) may be made of any material that provides sufficient strength, dimensional stability and heat transfer characteristics to permit operation for which the process microchannel is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin assembly (380, 380a, 380b) may be made of an $Al_2O_3$ forming material such as an alloy comprising Fe, Cr, Al and Y, or a $Cr_2O_3$ forming material such as an alloy of Ni, Cr and Fe.

Figure 27:
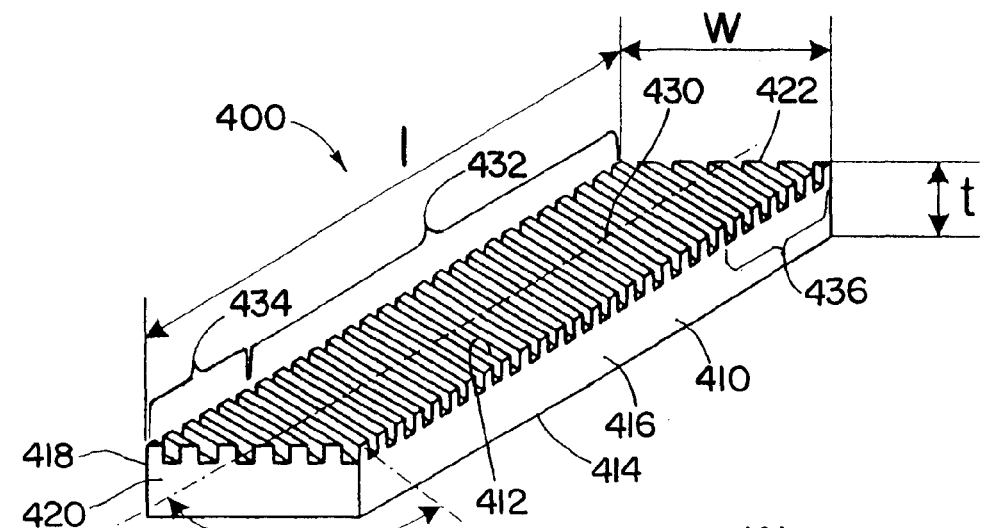
FIG. 27 is a schematic illustration of a microgrooved support strip that may be used to support a catalyst for use with the inventive process, the support strip comprising a top surface, a bottom surface, a front edge, back edge and side edges. The edges may be sufficiently open to permit fluid to flow through the edges.
Figure 28:
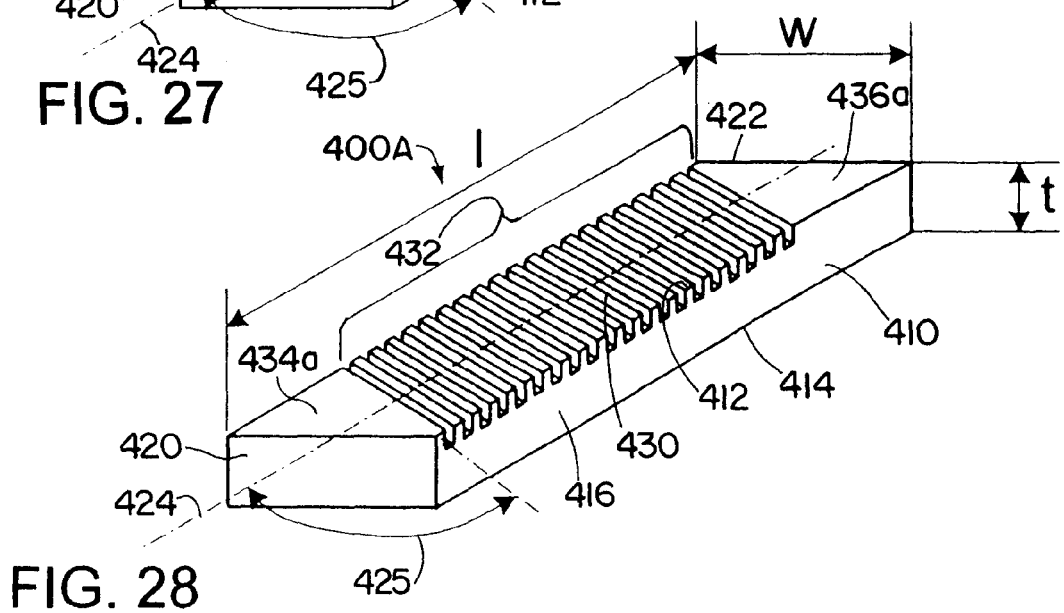
FIG. 28 is a schematic illustration of a microgrooved support strip similar to the support strip illustrated in FIG. 27 with the exception that the front edge and the back edge of the microgrooved support strip illustrated in FIG. 28 are closed and thus do not permit fluid to flow through the front and back edges.
Figure 29:
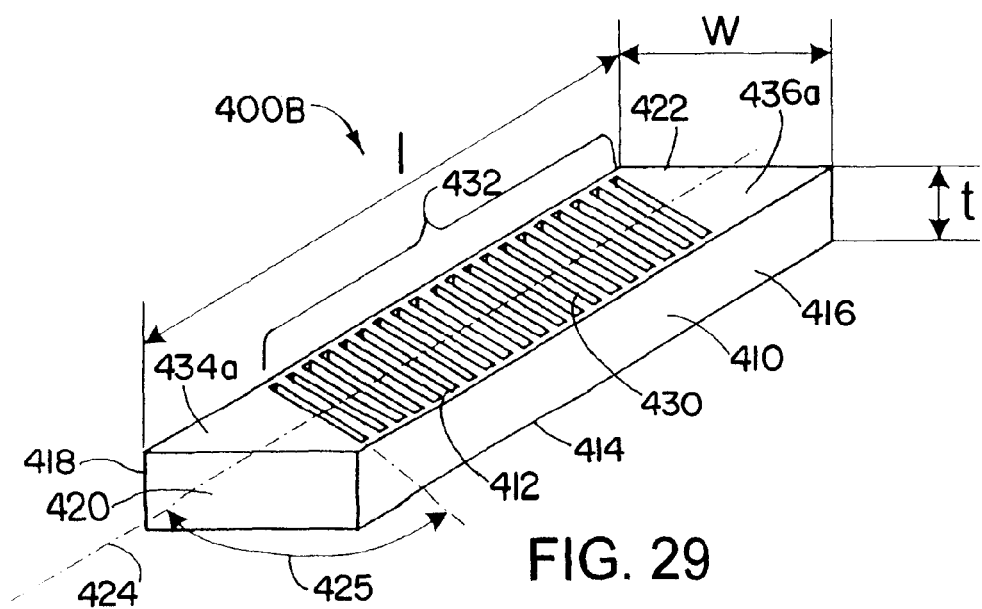
FIG. 29 is a schematic illustration of a microgrooved support strip similar to the support strip illustrated in FIG. 28 with the exception that the side edges of the microgrooved support strip illustrated in FIG. 29 are closed and thus do not permit fluid to flow through the side edges. The microgrooves may penetrate part way or all the way through the support strip. Penetration of the microgrooves all the way through the support strip may permit fluid to flow through the microgrooves in the direction from the top surface to the bottom surface, or vice versa.

The catalyst may be supported by the microgrooved support strip illustrated in FIGS. 27, 28 or 29. Referring to FIG. 27, microgrooved support strip 400 comprises support strip 410 which is rectangular in shape and has a length (l), width (w) and thickness (t). The support strip 410 has a first or top surface 412, a second or bottom surface 414, a first side edge 416, a second side edge 418, a front edge 420 and a back edge 422. The support strip 410 has a center axis 424 extending along the length (l) of the support strip. A plurality of parallel microgrooves 430 are formed in the first surface 412. A first group 432 of parallel microgrooves extends from the first side edge 416 of the support strip 410 to the second side edge 418. A second group 434 of the microgrooves 430 extends from the front edge 420 to the second side edge 418. A third group 436 of the microgrooves 430 extends from the first side edge 416 of the support strip 410 to the back edge 422. The microgrooves 430 are oriented at an angle 425 relative to the center axis 420 that is sufficient to permit fluid to flow in the microgrooves 430 in a general direction from the front edge 420 toward the back edge 422. That is, the microgrooves 430 do not extend straight across the top surface 412 at an angle of 90° with the center axis 424. The front edge 420, back edge 422 and side edges 416 and 418 of the microgrooved support strip 400 are open. That is, the microgrooves 430 have open ends that project through the front edge 420, back edge 422 and side edges 416 and 418. These open ends may permit the flow of fluid through the front edge, back edge and side edges.

The microgrooves 430 illustrated in FIG. 27 have cross-sections in the form of squares. Alternatively, each of the microgrooves 430 may have a rectangular cross-section, a vee shaped cross-section, a semi-circular cross-section, a dovetail shaped cross-section, or a trapezoid shaped cross-section. Those skilled in the art will recognize that microgrooves with other cross-sectional shapes may be used. Each of the microgrooves 430 has a depth, width and length. The depth of each of the microgrooves 430 may be in the range from about 0.1 to about 1000 microns, and in one embodiment from about 1 to about 100 microns. The width, which would be the width at its widest dimension, for each of the microgrooves 430 may be in the range of about 0.1 to about 1000 microns, and in one embodiment from about 1 to about 500 microns. The length of each of the microgrooves 430 may be of any dimension which depends upon the width (w) of the support strip 410.

The length of each microgroove 430 may be in the range of about 0.1 to about 100 cm, and in one embodiment from about 0.1 to about 10 cm. The spacing between the microgrooves 430 may be in the range up to about 1000 microns, and in one embodiment from about 0.1 to about 1000 microns, and in one embodiment from about 1 to about 1000 microns.

Each of the microgrooves 430 may be oriented toward the front edge 420 and the first side edge 416 and forms an angle 425 with the center axis 424 that is sufficient to permit fluid to flow in the microgrooves in a general direction toward the second side edge 418 and back edge 422. The angle 425 may be more than about 0° and less than 90°. The angle 125 may be in the range from about 50° to about 80°, and in one embodiment from about 60° to about 75°. The microgrooves 430 may be formed in the first surface 412 of the support strip 410 by any suitable technique, including photochemical machining, laser etching, water jet machining, and the like.

The support strip 410 may have a thickness (t) in the range from about 0.1 to about 5000 microns, and in one embodiment from about 1 to about 1000 microns. The support strip 410 may have any width (w) and any length (l), the width and length depending upon the dimensions of the microchannel for which the support strip 410 is to be used. The support strip 410 may have a width (w) in the range from about 0.01 to about 100 cm, and in one embodiment from about 0.1 to about 10 cm. The length (l) of the support strip 110 may be in the range of about 0.01 to about 100 cm, and in one embodiment from about 0.1 to about 10 cm. The support strip 410 as illustrated in FIG. 27 is in the form of a rectangle. However, it is to be understood that the support strip 410 may have any configuration, for example, square, circle, oval, etc., to conform to the design of the microchannel for which it is to be used.

The support strip 410 may be made of any material that provides sufficient strength, dimensional stability and heat transfer characteristics to permit the use of the microgrooved support strip 400 in a microchannel for supporting a catalyst. The support strip 410 may be made of metal, silicon carbide, graphite or a combination of two or more thereof. The metal may comprise steel, aluminum, titanium, nickel, platinum, rhodium, copper, chromium, brass, or an alloy of any of the foregoing metals. The support structure 410 may be made of stainless steel or an alloy comprising iron, chromium, aluminum and yttrium.

The microgrooved support strip 400A illustrated in FIG. 28 is the same as the microgrooved support strip 400 illustrated in FIG. 27 with the exception that the second group 434 of microgrooves 430 and third group 436 of microgrooves 430 that are present in the microgroove support strip 400 are not present in the microgrooved support strip 400A. The microgrooved support strip 400A includes non-grooved sections 434a and 436a which provide the microgrooved support strip 100A with a front edge 420 and a back edge 422 that are closed. That is, the front edge 420 and the back edge 422 of the microgrooved support strip 400A are sufficiently blocked to prevent fluid from flowing through the front edge 420 and back edge 422.

Figure 35:
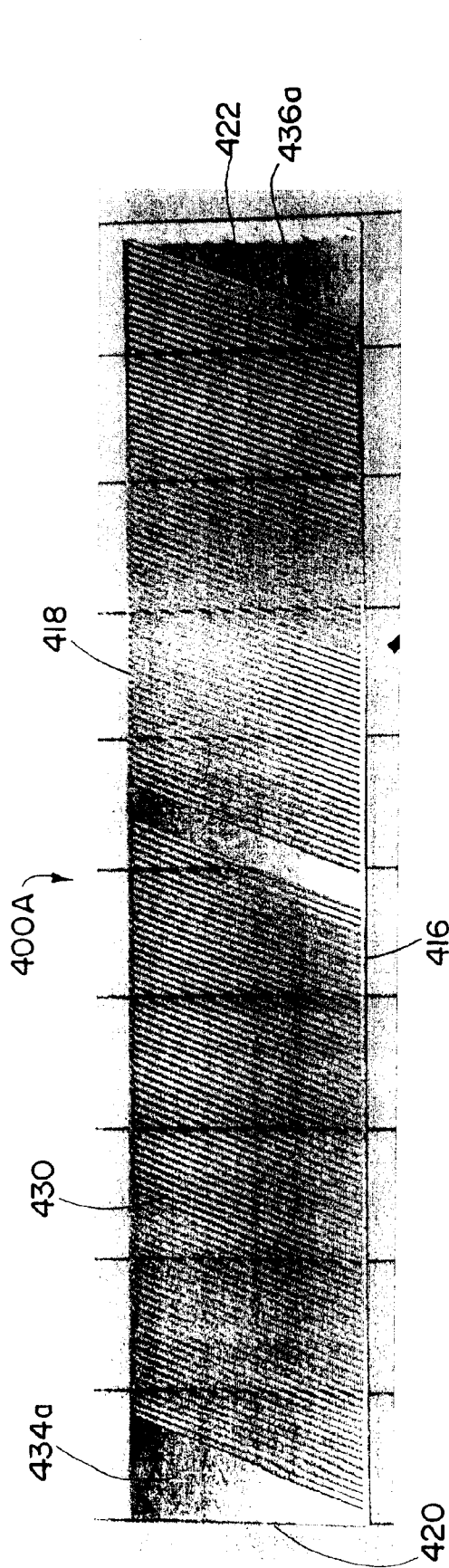
FIG. 35 is a photograph of a microgrooved support structure suitable for supporting a catalyst for use with the inventive process, the support structure being made of an alloy of iron, chromium, aluminum and yttrium, the thickness of the support structure being 0.002 inch (50.8 microns), the ribs dividing the microgrooves having a thickness of 0.007 inch (178 microns), and the microgrooves having a width of 0.007 inch (178 microns).
Figure 36:
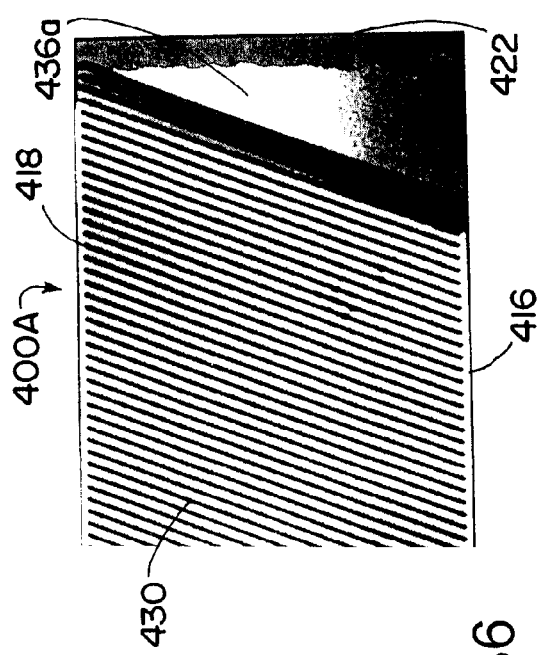
FIG. 36 is a photograph of a microgrooved support structure similar to the support structure illustrated in FIG. 35 with the exception that the microgrooved support structure illustrated in FIG. 36 is made of stainless steel.

The microgrooved support strip 400A is also shown in FIGS. 35 and 36. FIG. 35 is a photograph of a microgrooved support structure made of an alloy of iron, chromium, aluminum and yttrium, the thickness of the support structure being 0.002 inch (50.8 microns), the ribs dividing the microgrooves having a thickness of 0.007 inch (178 microns), and the microgrooves having a width of 0.007 inch (178 microns). FIG. 36 is a photograph of a microgrooved support structure similar to the support structure illustrated in FIG. 35 with the exception that the microgrooved support structure illustrated in FIG. 36 is made of stainless steel.

The microgrooved support strip 400B illustrated in FIG. 29 is the same as the microgrooved support strip 400A illustrated in FIG. 28 with the exception that the side edges 416 and 418 in the microgrooved support strip 400B are closed. The microgrooves 430 extend between the side edges 416 and 418 but not through the side edges. Thus, the flow of fluid through the side edges 416 and 418 may be blocked. Also, the microgrooves 430 may penetrate part way or all the way through the support strip 410. Penetration of the microgrooves 430 all the way through the support strip 410 may be sufficient to permit fluid to flow through the support strip 410 from the top surface 412 to the bottom surface 414, or vice versa.

The microgrooves 430 may be aligned at an angle of about 90° or a right angle with the center axis 424, and in one embodiment extend from the first side edge 416 to the second side edge 418.

The microgrooves 430 may be aligned parallel to the center axis 424, and in one embodiment extend from the front edge 420 to the back edge 422.

The microgrooved support strips 400 and 400B may be used as flow-through and/or flow-by support structures in a microchannel. Microgrooved support strip 400A may be used as a flow by support structure in a microchannel.

Figures 30, 31:
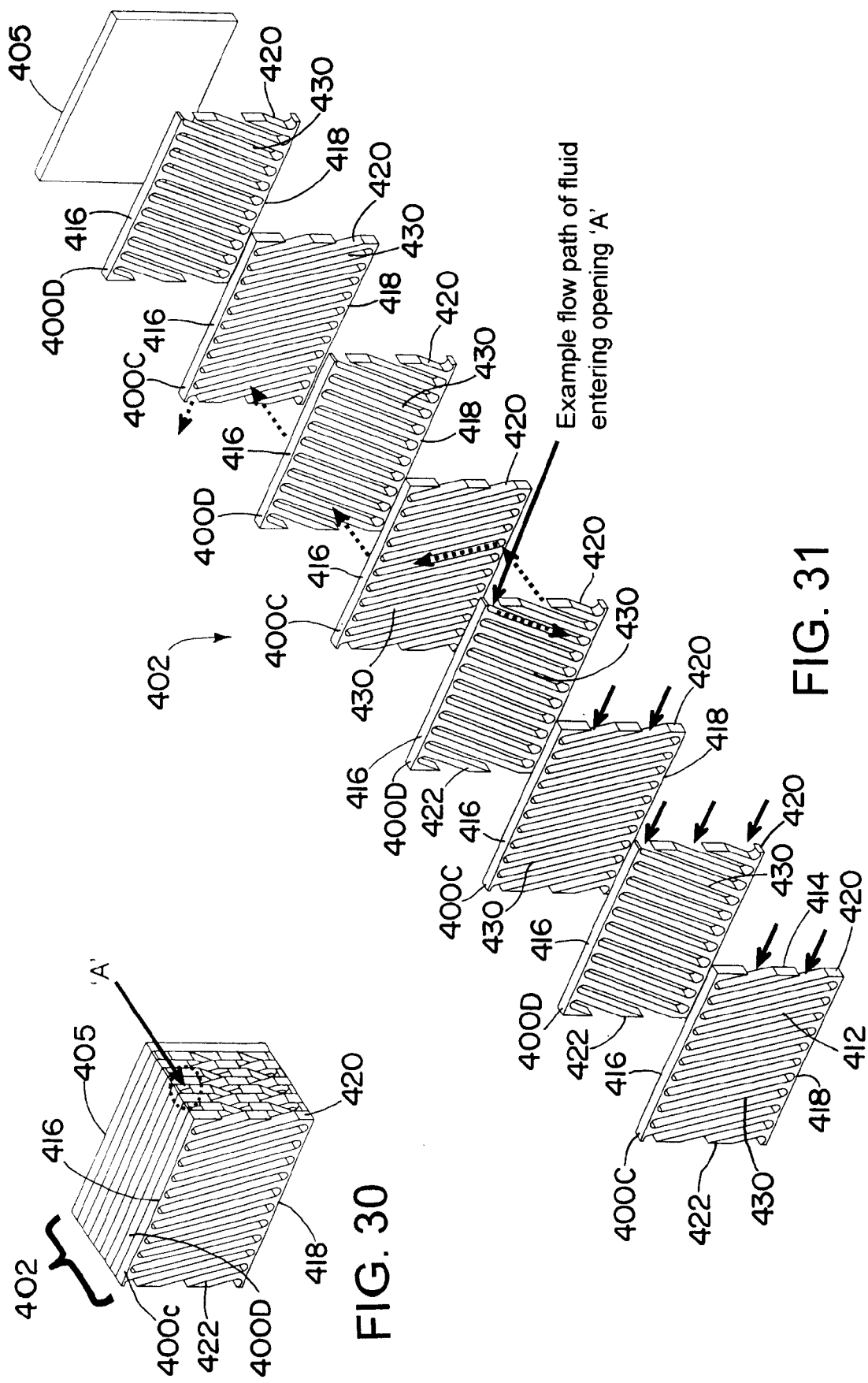
FIG. 30 is a schematic illustration showing a plurality of microgrooved support strips stacked one above another forming a composite support structure, the front and back edges of each of the microgrooved support strips being open sufficiently to permit fluid to flow through such edges. The microgrooves in each of the support strips project through the support strips sufficiently to permit fluid to flow through the support strips from one support strip to another.
FIG. 31 is a schematic illustration of an exploded view of the composite support structure illustrated in FIG. 30. The support structure illustrated in FIG. 31 comprises four (4) first microgrooved support strips and four (4) second microgrooved support strips positioned side by side in alternating sequence. The microgrooves in each of the support strips project through the support strips sufficiently to permit fluid to flow through the support strips from one support strip to another. The first microgrooved support strips employ microgrooves that form angles with the center axis of the support strips that are oriented toward the front edges and first side edges of the support strips and are more than about 0° and less than 90°, for example, in the range from about 60° to about 80°. The second microgrooved support strips employ microgrooves that form angles with the center axis of the support strips that are oriented toward the front edges and first side edges of the support strips and are more than 90° and less than about 180°, for example, in the range from about 100° to about 120°.

In one embodiment, a plurality of the microgrooved support strips may be stacked one above another or positioned side by side to form a composite support structure which may be used to support a catalyst for use in the inventive process. The composite support structure, in one embodiment, is illustrated in FIGS. 30 and 31. The support strips 400C and 400D illustrated in FIGS. 30 and 31 have open front 420 and back edges 422, closed side edges 416 and 418, and microgrooves 430 that penetrate all the way through the support strip 410 from the top surface 412 to the bottom surface 414. The open front edges 420, back edges 422 and microgrooves 430 permit fluid to flow through the microgrooved support strips from one support strip to another support strip within the composite support structure as the fluid flows through the composite support structure. The number of microgrooved support strips employed in such a composite support structure may be of any number, for example up to about 50, and in one embodiment up to about 30, and in one embodiment up to about 15, and in one embodiment up to about 10. The composite support structure also includes end plates to prevent fluid from flowing out of the sides of the composite construction.

The composite support structure 402 illustrated in FIGS. 30 and 31 comprises eight (8) microgrooved support strips, four each of microgrooved support strips 400C and 400D positioned side by side in alternating sequence and two end plates 405 (only one end plate is shown in FIG. 5). The microgrooved support strips 400C and 400D each comprise support strip 410 which is rectangular in shape and has a length, width and thickness. The support strip 410 has a center axis extending along the length of the support strip. A plurality of parallel microgrooves 430 are formed in the support strip 410 and project through the support strip from the top surface 412 to the bottom surface 414. The open front 420 and back edges 422 and the open microgrooves 430 permit fluid to flow from one microgrooved support strip to another within the composite support structure 402. A first group of parallel microgrooves extends from the first side edge 416 of the support strip 410 to the second side edge 418. A second group of the microgrooves 430 extends from the front edge 420 to the second side edge 418. A third group of the microgrooves 430 extends from the first side edge 416 of the support strip 410 to the back edge 422. The microgrooves 430 extend to the side edges 416 and 418 but do not project through these side edges. The end plates 405 prevent fluid from flowing out of the sides of the composite support structure 402. The second end plate 405 that is not shown in the drawings would be positioned adjacent to the first microgrooved support strip 400C on the left side in FIGS. 30 and 31. The microgrooves 430 in the support strips 400C are oriented at an angle relative to the center axis of the support strip and the side edge 416 that is more than 90° and less than 180°, and in one embodiment in the range from about 100° to about 150°. The microgrooves 430 in the support strip 400D are oriented at an angle relative to the center axis of the support strip and the side edge 116 that is more than 0° and less than 90°, and in one embodiment in the range from about 50° to about 80°. Fluid flows through the composite structure 402 by entering the front edge 420 of the support strips 400C and 400D, flowing in and through the microgrooves 430 and transferring from the microgrooves 430 in one support strip (400C or 400D) to the microgrooves 430 in another support strip (400C or 400D) until the fluid reaches the back edge 422 of the support strips and then flows out of composite support structure 402. FIG. 31 shows an example of a flow path through the composite support structure 402 for a fluid entering opening 'A' of the composite support structure illustrated in FIG. 20. The flow of fluid through the composite support structure 402 may be described as permeating, diffusing and advecting from one layer to another until the fluid passes from the front end of the composite support structure to the back end.

The catalyst may be supported by a composite support structure, comprising: at least one first support strip comprising a first surface, a second surface, a length with a center axis extending along the length, a front edge, a back edge, a first side edge, a second side edge, the front edge and the back edge extending from the first side edge and to the second side edge, a plurality of parallel microgrooves in the first surface aligned at an angle of about 90° with the center axis; and at least one second support strip comprising a first surface, a second surface, a length with a center axis extending along the length, a front edge, a back edge, a first side edge, a second side edge, the front edge and the back edge extending from the first side edge to the second side edge, a plurality of parallel microgrooves in the first surface aligned parallel with the center axis; the first support strip being adjacent to the second support strip with the second surface of the first support strip contacting the first surface of the second support strip; the microgrooves penetrating through the support strips sufficiently to permit fluid to flow through the support strips from one support strip to another support strip.

The catalyst may be supported by a composite support structure, comprising: at least one first support strip comprising a first surface, a second surface, a length with a center axis extending along the length, a front edge, a back edge, a first side edge, a second side edge, the front edge and the back edge extending from the first side edge and to the second side edge, and a plurality of parallel microgrooves in the first surface; at least one second support strip comprising a first surface, a second surface, a length with a center axis extending along the length, a front edge, a back edge, a first side edge, a second side edge, the front edge and the back edge extending from the first side edge to the second side edge, and a plurality of parallel microgrooves in the first surface; the first support strip being adjacent to the second support strip with the second surface of the first support strip contacting the first surface of the second support strip; the microgrooves penetrating through the support strips sufficiently to permit fluid to flow through the support strips from one support strip to another; microgrooves in the first surface of the first support strip intersecting microgrooves in the first surface of the second support strip to provide through holes extending through the first support strip and through the second support strip. In one embodiment, the through holes may be of sufficient dimension to permit reactants and/or product to flow from the first surface of the first support strip to the first surface of the second support strip and/or from the first surface of the second support strip to the first surface of the first support strip. In one embodiment, the first support strip and the second support strip are made of thermally conductive materials and the contacting between the second surface of the first support strip and the first surface of the second support strip is sufficient to permit heat to be conducted between the first support strip and the second support strip.

An advantage of the microgrooved support strips and composite structures relates to the fact that microsized particles of catalyst may be positioned in and anchored to the microgrooves thus reducing the tendency of the particulates being swept away by the flow of process fluids through the microchannels.

The support strips 400, 400A or 400B, or the composite support structure 402 may be positioned or mounted on one or more walls within a microchannel to form one or more structured walls within the microchannel.

Figure 59:
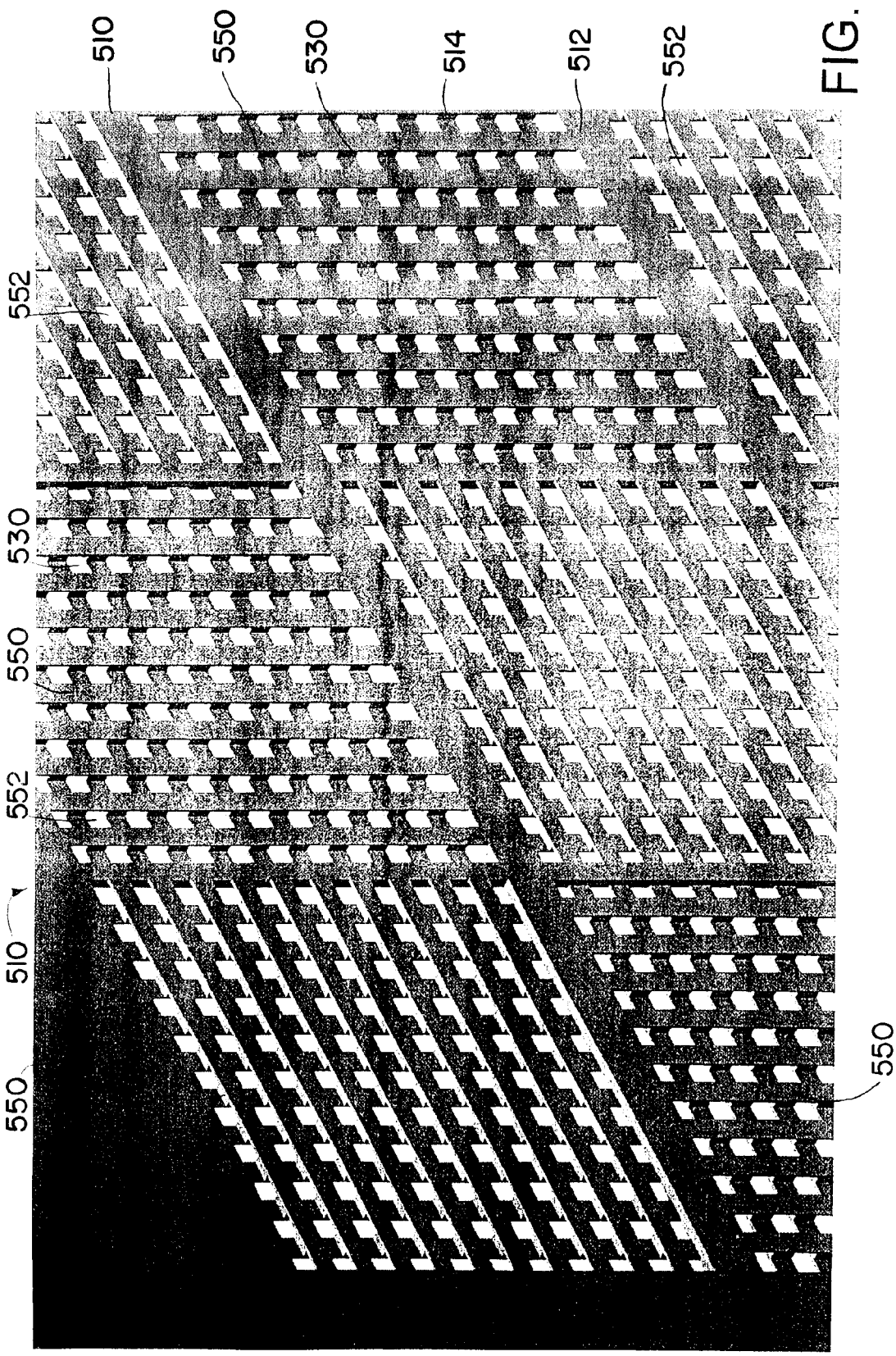
FIG. 59 is a schematic illustration of a shim which has a front or first surface and a back or second surface, and grooves or microgrooves formed in each surface, the grooves or microgrooves in the front or first surface intersecting the grooves or microgrooves in the back or second surface with the result being the formation of a plurality of voids, through holes or openings in the shim.
Figure 60:
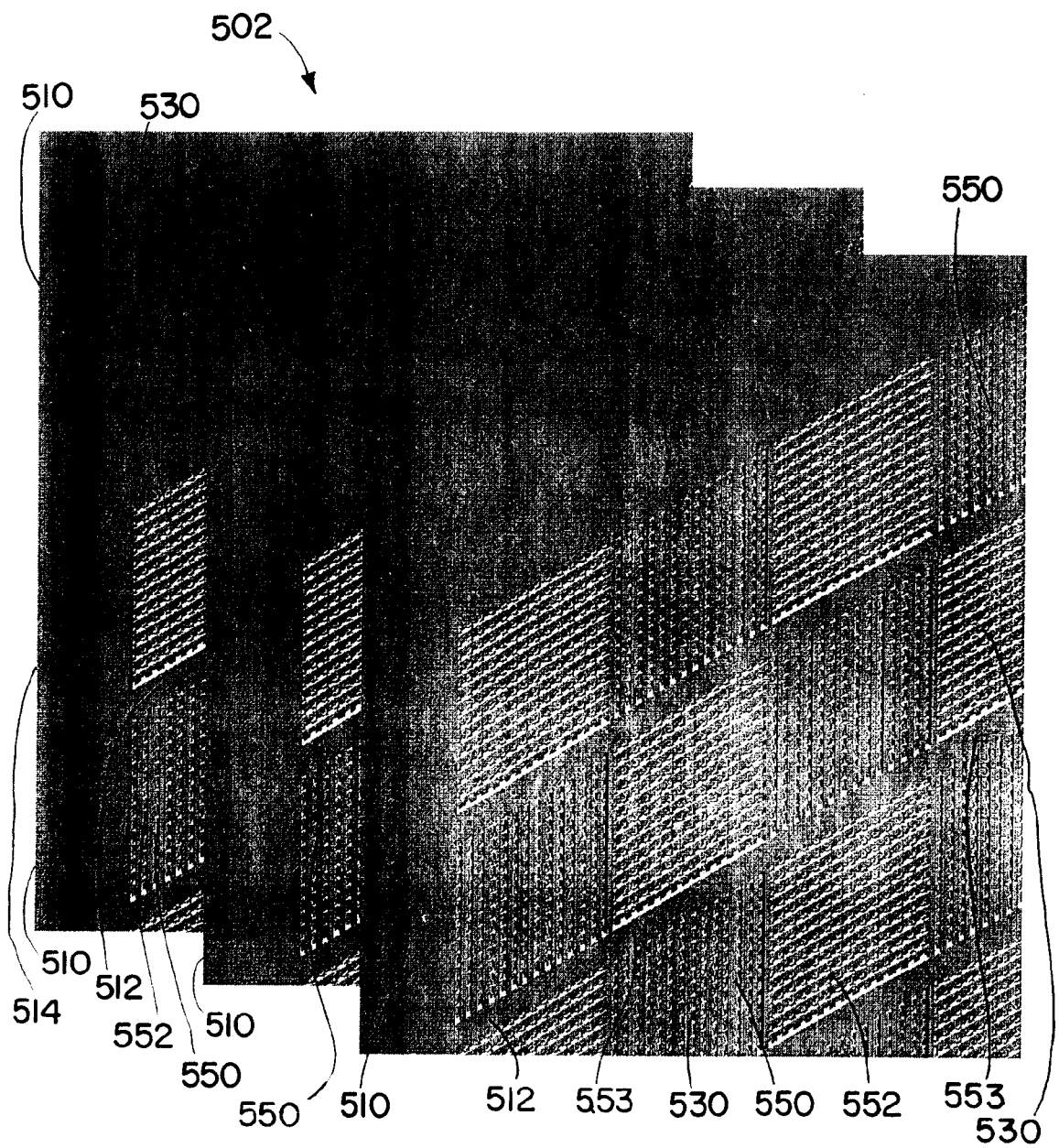
FIG. 60 is a schematic illustration of a composite structure comprising a plurality of the shims illustrated in FIG. 59.

The catalyst may be supported by one or more structured walls within the process microchannels wherein the one or more structured walls may be formed from one or more shims. One or more of the shims may contain one or more void spaces, openings or through holes. The shims may contain grooves or microgrooves that are formed in one surface of the shims or in both the front or first surface and the back or second surface of the shims. The grooves or microgrooves from the first surface may intersect the grooves or microgrooves from the second surface to form a plurality of voids, through holes or openings in the shim. Examples are illustrated in FIGS. 59 and 60. FIG. 59 illustrates a shim 510 which has a front or first surface 512 and a back or second surface 514, and a plurality of grooves or microgrooves 530 formed in each surface. The grooves or microgrooves 530 formed in the front surface 512 are parallel to each other and are positioned in an array of block patterns 550 wherein in a first block pattern 550 the grooves or microgrooves are aligned in a first or horizontal direction and then in an adjacent second block pattern 550 the grooves or microgrooves are aligned in a second or vertical direction. The array of block patterns 550 comprises a plurality of block patterns 550 arranged in successive rows positioned one above another, the successive rows forming a plurality of columns positioned side by side one another. The grooves or microgrooves 530 formed in the back surface 514 are also parallel to each other and are positioned in an array of block patterns 550 similar to the block patterns 550 in the front surface 512 with the exception that where the front surface 512 has grooves or microgrooves that are aligned in a first or horizontal direction the back surface 514 has grooves or microgrooves 530 that are aligned in a second or vertical direction. Similarly, where the front surface 512 has grooves or microgrooves 530 that are aligned in a second or vertical direction the back surface 514 has grooves or microgrooves that are aligned in a first or horizontal direction. The grooves or microgrooves 530 in the front surface 512 and the grooves or microgrooves 530 in the back surface 514 partially penetrate the shim 510. The penetration of the grooves or microgrooves 530 in the front surface and back surface is sufficient for the grooves or microgrooves 530 in the front surface 512 to intersect the grooves or microgrooves 530 in the back surface 514 with the result being the formation of an array of voids, through holes or openings 552 in the shim 510 at the points where the grooves or microgrooves intersect. The openings 552 may be of sufficient size to permit a fluid to flow or diffuse through the openings 552. The number of openings may range from about 1 to about 200,000 openings per cm$^2$, and in one embodiment from about 10 to about 100,000 openings per cm$^2$. The openings 552 may have average dimensions (e.g., diameter) in the range from about 1 to about 2000 microns, and in one embodiment from about 10 to about 1000 microns. The block patterns 550 may have the dimensions of about 0.01 by about 500 mm, and in one embodiment about 0.5 by about 20 mm. The separation between each block pattern 550 and the next adjacent block pattern may be in the range from about 0.01 to about 10 mm, and in one embodiment about 0.1 to about 1 mm. In this embodiment, the pattern is alternated in an A, B, A, B fashion. In an alternate embodiment the geometry may be varied such that the surface area to volume of the structure may be different along the length of the reactor or in different zones of the reactor. By this manner a reaction with a very high rate of heat release near the top of the reactor may be advantaged by the use of a structure with a higher surface area to volume near the middle or end of the reactor where the kinetics are slower and the rate of heat transfer lower. The resulting heat generation rate along the reactor length or heat flux profile along the reactor length may be made more even or uniform. The pattern may be further optimized to maximize selectivity to the desired reaction products. The pattern may also be optimized to create a tailored gradient within the catalyst structure, along the length of the catalyst structure, or both.

The grooves or microgrooves 530 in the front or first surface 512 intersect the grooves or microgrooves in the back or second surface 514 at right angles in the illustrated embodiment, however, it is to be understood that the angles of intersection may be of any value (e.g., from about 30° to about 120°) and are therefore not limited to being only right angles.

FIG. 60 illustrates a composite structure 502 comprising a plurality of the shims 510 illustrated in FIG. 59 which may be stacked one above another or positioned side by side. Any number of shims 510 may be stacked one above the other or positioned side by side in the composite support structure 502. For example, 2, 3, 4, 6, 8, 10, 20, 30, 50, 100, etc., shims 510 may be stacked one above another.

The catalyst may be deposited on the support strips 400, 400A, 400B, 400C or 400D, or shims 510, using conventional techniques. These may include washcoating the catalyst on the support strips or shims, growing the catalyst on the support strips or shims, or depositing the catalyst on the support strips or shims using vapor deposition. The vapor deposition may be chemical vapor deposition or physical vapor deposition. The catalyst may be deposited by slurry-coating, sol-coating or solution-coating. In one embodiment, the catalyst may be in the form of microsized particulates deposited in and adhered to the grooves or microgrooves of the support strips or shims. The catalyst loading may be in the range from about 0.1 to about 100 milligrams (mg) per square centimeter of support strip or shim, and in one embodiment in the range from about 1 to about 10 mg of catalyst per square centimeter of support strip or shim. The microsized particulates may have average particle sizes in the range from about 0.01 to about 100 microns, and in one embodiment in the range from about 0.1 to about 50 microns, and in one embodiment in the range from about 0.1 to about 10 microns, and in one embodiment from about 0.1 to about 7 microns, and in one embodiment from about 0.1 to about 5 microns, and in one embodiment from about 0.1 to about 3 microns, and in one embodiment from about 0.1 to about 2 microns, and in one embodiment from about 0.1 to about 1 micron, and in one embodiment from about 0.1 to about 0.5 micron.

Figure 38:
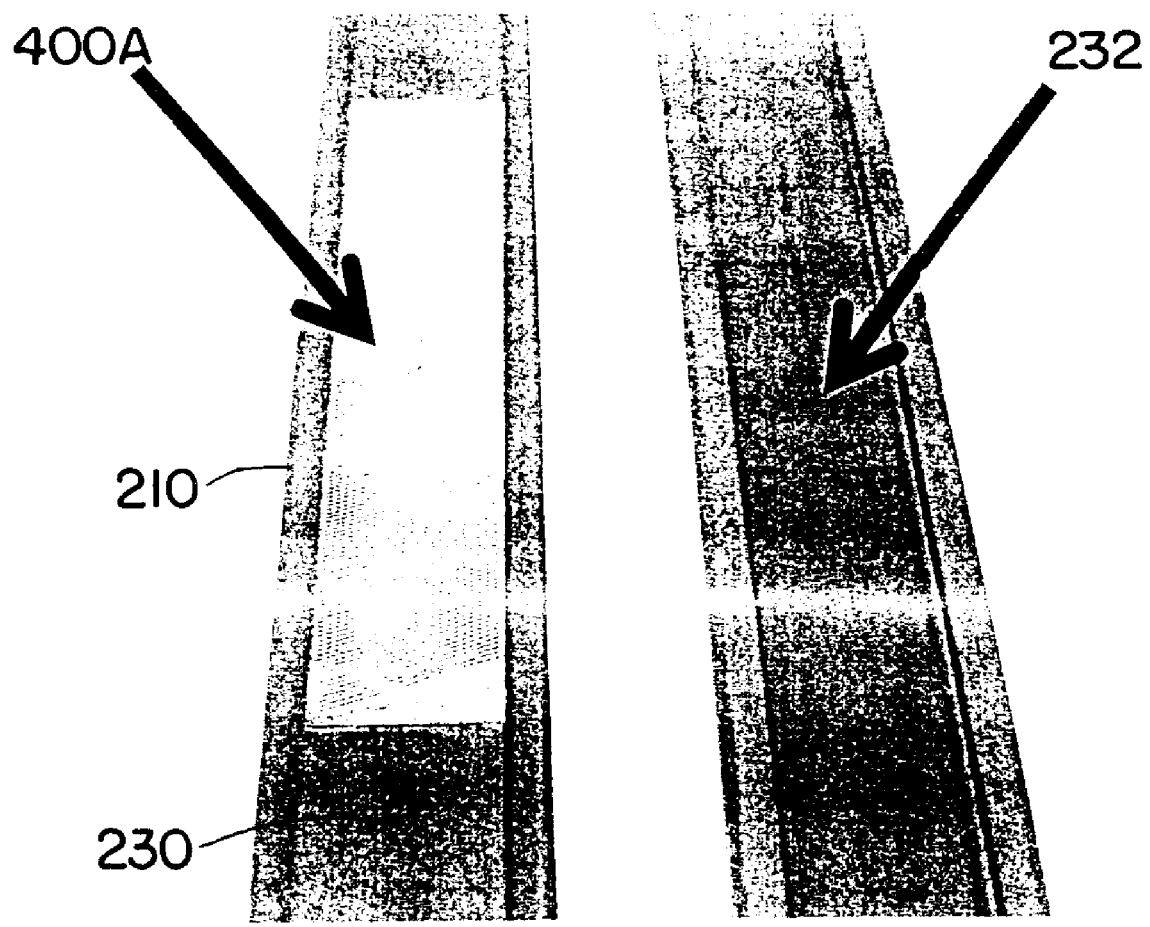
FIG. 38 is a photograph of a process microchannel containing two catalyst supporting microgrooved support structures of the type illustrated in FIG. 28. The process microchannel has a length of 2.5 inches (6.35 cm), a width of 0.5 inch (12.7 mm), and a height of 0.002 inch (50.8 microns). A top plate for the process microchannel is shown on the right side of FIG. 38.

Repeating units for use in microchannel reactor core 110 employing support strip 400A for supporting a catalyst are illustrated in FIGS. 32, 33 and 48-53. The number of these repeating units that may be used in the microchannel reactor core 110 may be any number, for example, one, two, three, four, five, six, eight, ten, hundreds, thousands, etc. Referring to FIG. 32, repeating unit 201A includes process microchannel 210 with support strip 400A mounted on interior wall 230 of the process microchannel 210. Bulk flow region 234 is defined by the space within the process microchannel 210 above the support strip 400A. Process fluid flows through the process microchannel 210 as indicated by arrows 220 and 222. In flowing through the process microchannel 210, the process fluid flows through the bulk flow region 234 in contact with the catalyst support strip 400A. The catalyst may be in the form of microsized particulates positioned in the microgrooves 430. The support strip 400A is a flow-by support strip. However, some of the process fluid may flow in the microgrooves 430 in contact with the catalyst. The flow of the process fluid through the microgrooves 430 may be in the general direction from the first side edge 416 toward the second side edge 418 and the back edge 422. FIG. 38 is a photograph of a process microchannel 210 corresponding to the process microchannel 210 schematically illustrated in FIG. 32.

The repeating unit 201B illustrated in FIG. 33 is similar to the repeating unit 201A illustrated in FIG. 32 with the exception that the process microchannel 210 illustrated in FIG. 33 contains opposite interior walls 230 and 232 and a catalyst supporting support strip 400A mounted on each of the opposite interior walls.

Figure 34:
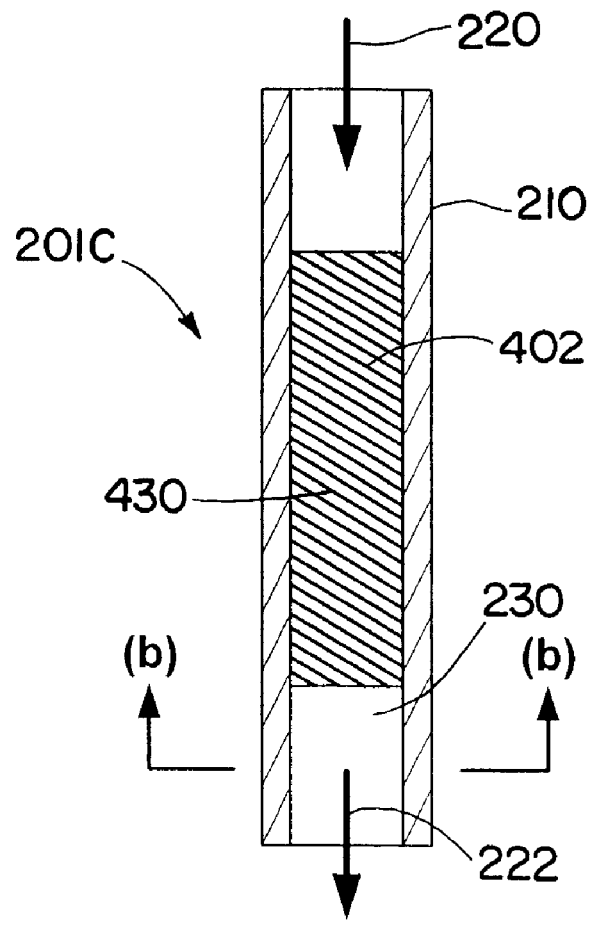
FIG. 34(a) is a schematic illustration of a repeating unit comprising a process microchannel that may be used in the microchannel reactor illustrated in FIG. 6. The process microchannel contains a catalyst supporting composite support structure of the type illustrated in FIGS. 30 and 31.
FIG. 34(b) is a cross-sectional view of the process microchannel illustrated in FIG. 34(a) taken along line (b)-(b).
Figure 34:
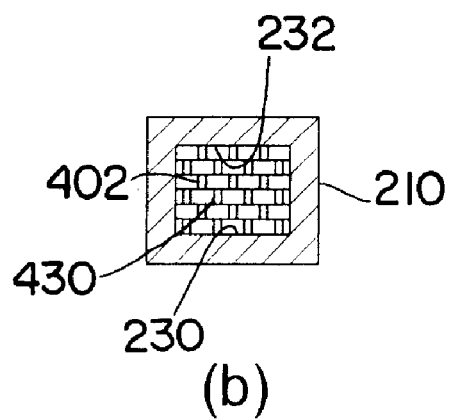

The repeating unit 201C illustrated in FIG. 34 contains composite support structure 402 in its reaction zone. The process fluids flow through the process microchannel 210 in the direction indicated by arrows 220 and 222. The composite support structure 402 is a flow-through device. In the composite support structure 402, the openings in the microgrooves 430 in each of the support strips 400C and 400D are sufficient to permit flow to permeate, defuse and/or weakly advect from layer to layer to fully access the catalytic sites.

Figure 39:
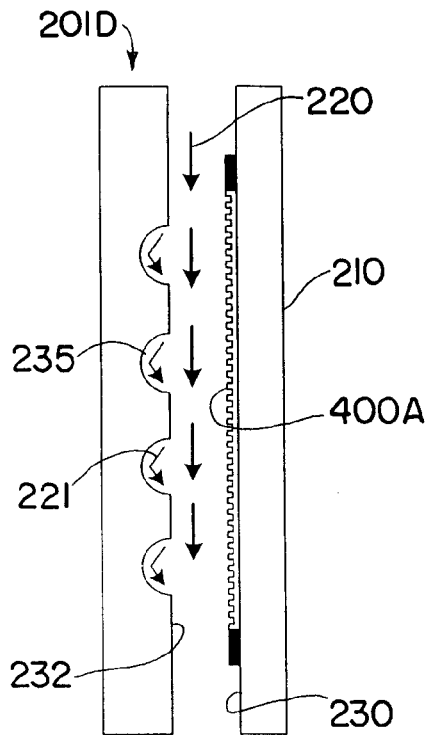
FIG. 39 is a schematic illustration of a repeating unit comprising a process microchannel that may be used in the microchannel reactor illustrated in FIG. 6. The process microchannel contains a catalyst supporting microgrooved support strip on one interior wall of the process microchannel and surface features for modifying the flow of process fluid in the process microchannel on an opposite interior wall. The microgrooved support strip corresponds to the microgrooved support strip illustrated in FIG. 28. The surface features are in the form of spherical depressions in the interior wall of the process microchannel. The flow of process fluid through the process microchannel is indicated by the arrows in FIG. 39.

The repeating unit 201D illustrated in FIG. 39 includes process microchannel 210 which has support strip 400A mounted on interior wall 230 and surface features 235 formed in the opposite interior wall 232. Process fluid flows through the process microchannel 210 as indicated by arrows 220. The flow of the process fluid is modified as the process fluid flows through surface features 235. The surface features 235 illustrated in FIG. 39 are in the form of spherical depressions in the microchannel wall 232. The modification of the flow of the process fluids by the surface features 235 enhances contact between the process fluid and the catalyst supported by the support structure 400A.

Figure 40:
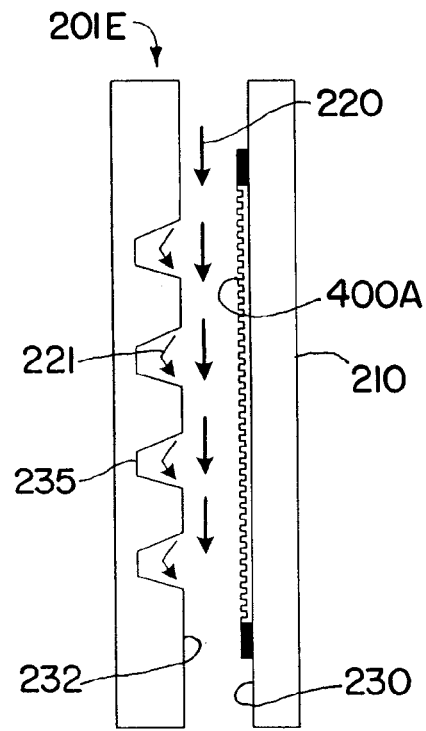
FIG. 40 is a schematic illustration of a repeating unit comprising a process microchannel that may be used in the microchannel reactor illustrated in FIG. 6. The process microchannel contains a catalyst supporting microgrooved support strip on one interior wall of the process microchannel and surface features for modifying the flow of process fluid in the process microchannel on an opposite interior wall. The microgrooved support strip corresponds to the microgrooved support strip illustrated in FIG. 28. The surface features are in the form of frustrum depressions in the interior wall of the process microchannel. The flow of process fluid through the process microchannel is indicated by the arrows in FIG. 40.

The repeating unit 201E illustrated in FIG. 40 is similar to the repeating unit 201D illustrated in FIG. 39 with the exception that the surface features 235 are in the form of frustrum depressions in the microchannel wall 232.

Figure 41:
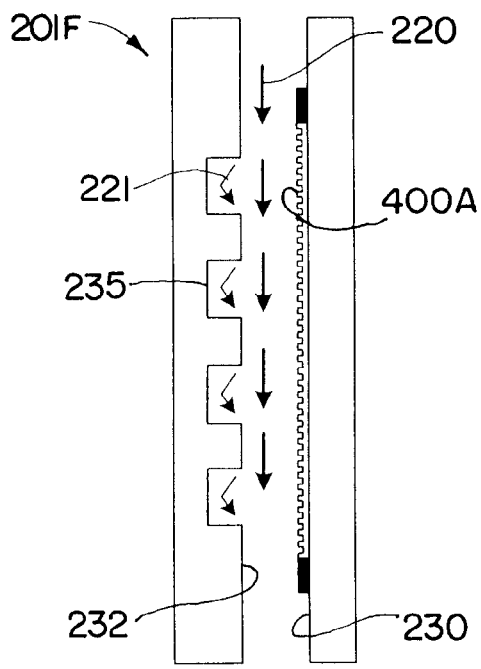
FIG. 41 is a schematic illustration of a repeating unit comprising a process microchannel that may be used in the microchannel reactor illustrated in FIG. 6. The process microchannel contains a catalyst supporting microgrooved support strip on one wall of the process microchannel and surface features for modifying the flow of process fluid in the process microchannel on an opposite interior wall. The microgrooved support strip corresponds to the microgrooved support strip illustrated in FIG. 28. The surface features are in the form of angled rectangular depressions in the interior wall of the process microchannel. The flow of process fluid through the process microchannel is indicated by the arrows in FIG. 41.

The repeating unit 201F illustrated in FIG. 41 is similar to the repeating unit 201D illustrated in FIG. 39 with the exception that the surface features 235 in FIG. 41 are in the form of rectangular depressions in the microchannel wall 232.

Figure 42:
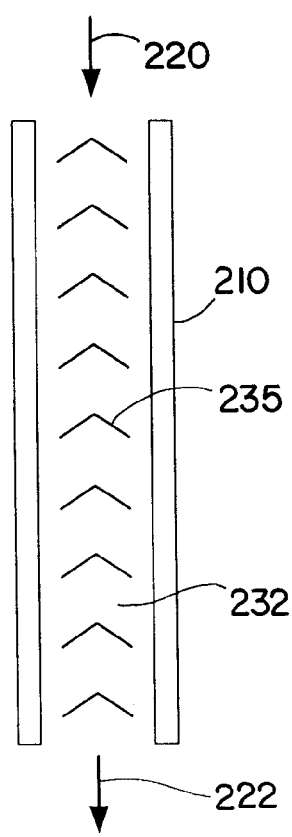
FIG. 42 is a schematic illustration of a modified version of the surface features illustrated in FIGS. 39, 40 or 41 that may be used in combination with the catalyst supporting microgrooved support strip illustrated in FIGS. 39, 40 or 41. The surface features illustrated in FIG. 42 comprise depressions in or projections from the microchannel wall which are in the form of vanes.
Figure 43:
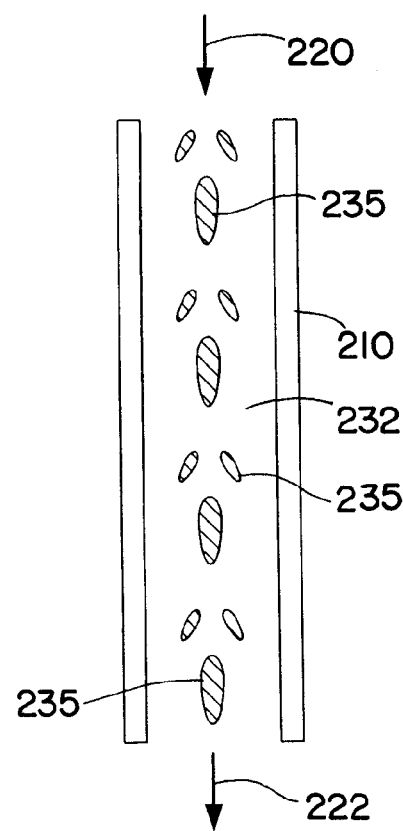
FIG. 43 is a schematic illustration of a modified version of the surface features illustrated in FIGS. 39, 40 or 41 that may be used in combination with the catalyst supporting microgrooved support strip illustrated in FIGS. 39, 40 or 41. The surface features illustrated in FIG. 43 comprise depressions in or projections from the microchannel wall which are in the form of air foils.
Figure 44:
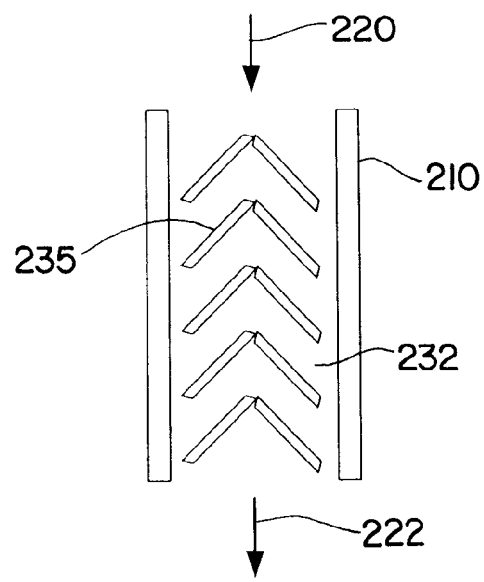
FIG. 44 is a schematic illustration of a modified version of the surface features illustrated in FIGS. 39, 40 or 41 that may be used in combination with the catalyst supporting microgrooved support strip illustrated in FIGS. 39, 40 or 41. The surface features illustrated in FIG. 44 comprise angular rectangular depressions in or projections from the microchannel wall.

The interior wall 232 of process microchannel 210 is illustrated in FIGS. 42, 43 and 44 wherein surface features of different forms are provided. The surface features in FIG. 42 are in the form of depressions in or projections from the microchannel wall 232 which are in the form of vanes. The surface features illustrated in FIG. 43 are in the form of depressions in or projections from the microchannel wall 232 which are in the form of air foils. The surface features illustrated in FIG. 44 are in the form of angular rectangular depressions in or projections from the microchannel wall 232.

Figure 45:
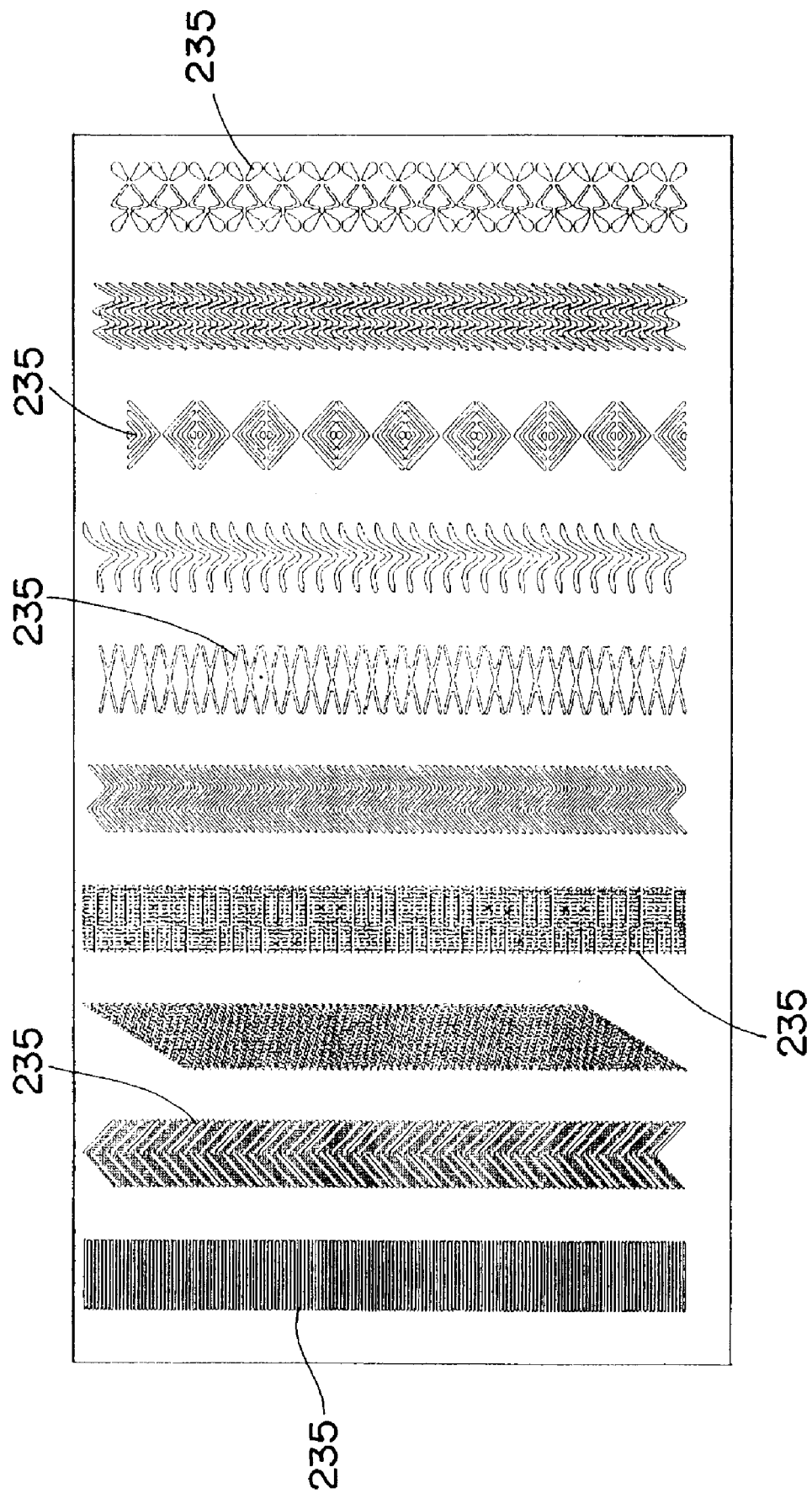
FIG. 45 is a schematic illustration of various surface feature designs that may be used in the process microchannels illustrated in FIGS. 39, 40 or 41 in combination with a catalyst supporting microgrooved support strip. Each of the configurations illustrated in FIG. 45 comprise depressions in or projections from the process microchannel wall.

Surface features 235 of various designs are illustrated in FIG. 45. Each of the surface features 235 illustrated in FIG. 45 may be in the form of a depressions in or a projections from microchannel wall 232.

Figure 48:
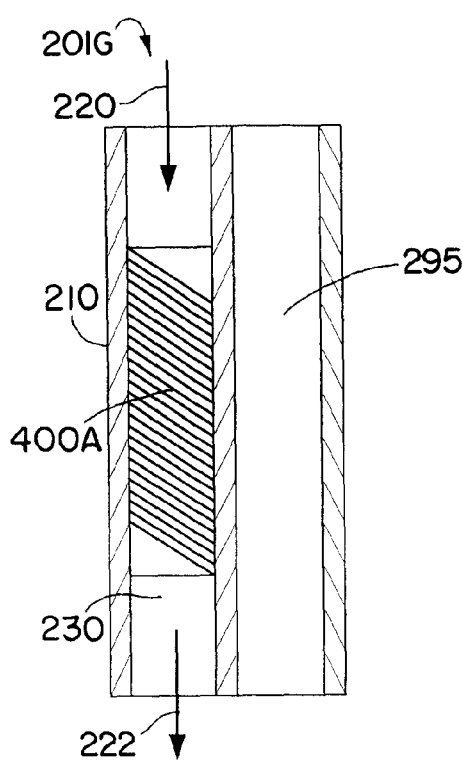
FIG. 48 is a schematic illustration of a repeating unit comprising a process microchannel and a heat exchange channel that may be used in the microchannel reactor illustrated in FIG. 6. The process microchannel contains a reaction zone comprising a catalyst supporting microgrooved support strip corresponding to the support strip illustrated in FIG. 28. The flow of heat exchange fluid in the heat exchange channel may be co-current or counter-current relative to the flow of process fluid in the process microchannel.

The repeating unit 201G illustrated in FIG. 48 comprises process microchannel 210 and heat exchange channel 295. This repeating unit is similar to repeating unit 210A illustrated in FIG. 32 except that repeating unit 201G includes heat exchange channel 295. The flow of heat exchange fluid in the heat exchange channel 295 may be co-current or counter-current relative to the flow of process fluid in the process microchannel 210.

Figure 49:
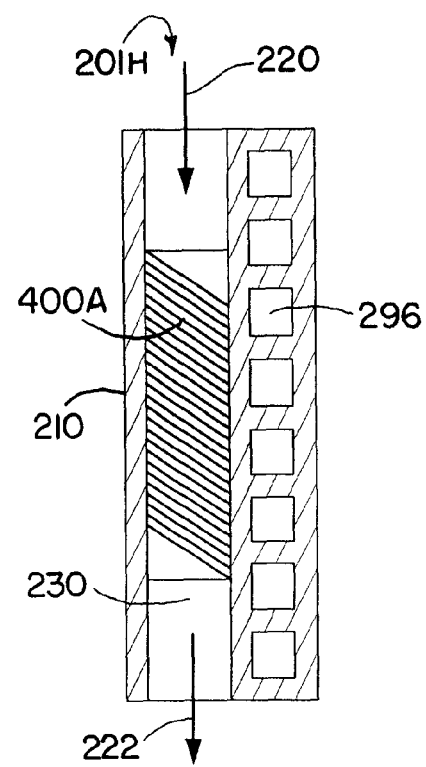
FIG. 49 is a schematic illustration of a repeating unit comprising a process microchannel and a plurality of heat exchange channels that may be used in the microchannel reactor illustrated in FIG. 6. The process microchannel contains a reaction zone comprising a catalyst supporting microgrooved support strip corresponding to the support strip illustrated in FIG. 28. The flow of heat exchange fluid in the heat exchange channels is cross-current relative to the flow of process fluid in the process microchannel.

FIG. 49 is a schematic illustration of repeating unit 201H which comprises process microchannel 210 and a plurality of heat exchange channels 296. The process microchannel 210 contains a reaction zone comprising a catalyst supporting support 400A. The flow of heat exchange fluid in the heat exchange channels 296 is cross-current relative to the flow of process fluid in the process microchannel.

Figure 50:
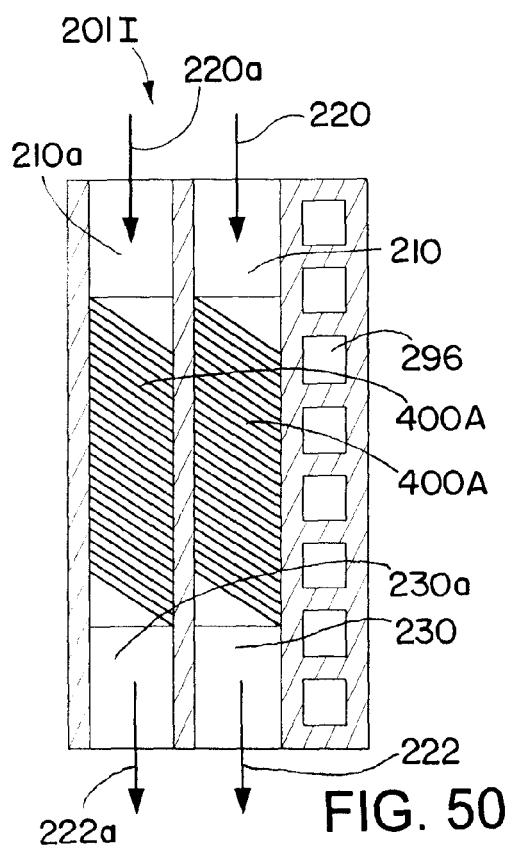
FIG. 50 is a schematic illustration of a repeating unit comprising two adjacent process microchannels, and a plurality of heat exchange channels that may be used in the microchannel reactor illustrated in FIG. 6. The process microchannels contain reaction zones comprising catalyst supporting microgrooved support strips corresponding to the support strip illustrated in FIG. 28. The heat exchange channels are adjacent to one of the process microchannel and in thermal contact with the other process microchannel. The flow of heat exchange fluid in the heat exchange channels is cross-current relative to the flow of process fluid in the process microchannels.

FIG. 50 is a schematic illustration of a repeating unit comprising two adjacent process microchannels 210 and 210a, and a plurality of heat exchange channels 296. The process microchannels 210 contain reaction zones comprising catalyst supporting support strips 400A. The heat exchange channels 296 are adjacent to microchannel 210 and in thermal contact with process microchannel 210a. The flow of heat exchange fluid in the heat exchange channels 296 is cross-current relative to the flow of process fluid in the process microchannels 210 and 210a.

Figure 51:
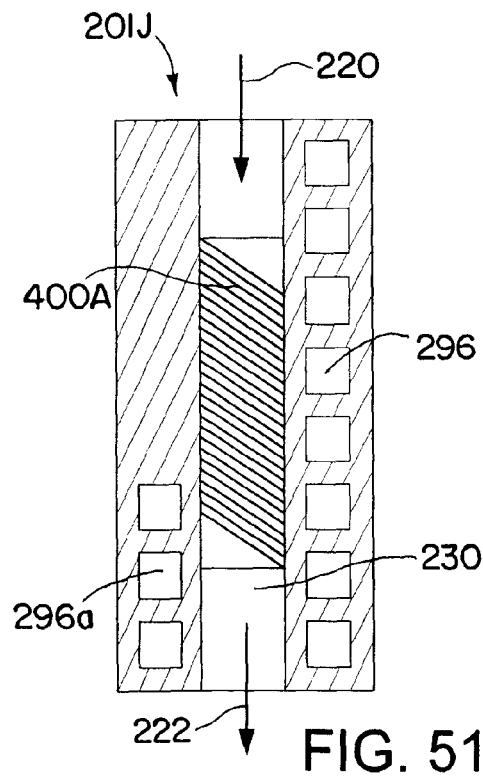
FIG. 51 is a schematic illustration of a repeating unit similar to the repeating unit illustrated in FIG. 49 with the exception that the repeating unit illustrated in FIG. 51 includes additional heat exchange channels near the exit of the process microchannel. These additional heat exchange channels may be used to provide for additional heating or cooling.

FIG. 51 is a schematic illustration of repeating unit 201J which is similar to repeating unit 201H illustrated in FIG. 49 with the exception that the repeating unit 201J includes additional heat exchange channels 296a near the exit of the process microchannel. These additional heat exchange channels may be used to provide for additional heating or cooling.

Figure 52:
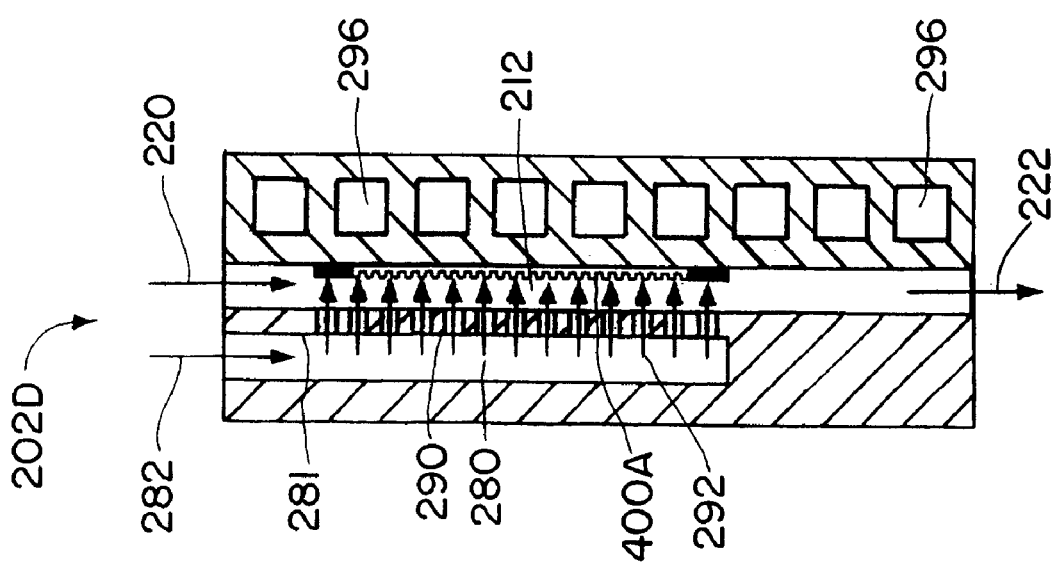
FIG. 52 is a schematic illustration of a repeating unit comprising a process microchannel, a staged addition channel, and a plurality of heat exchange channels that may be used in the microchannel reactor illustrated in FIG. 6. The process microchannel contains a reaction zone comprising a catalyst supporting microgrooved support strip corresponding to the support strip illustrated in FIG. 28. The staged addition channel and the process microchannel have a common wall with an apertured section positioned in the common wall. A feed composition comprising ethylbenzene flows in the process microchannel. A staged addition feed stream comprising oxygen flows from the staged addition channel through the apertured section into the process microchannel where it contacts and mixes with the feed composition. The oxygen and ethylbenzene react in the presence of the catalyst to form styrene. Heat exchange fluid flows in the heat exchange channels in a direction that is cross-current relative to the direction of flow of process fluids in the process microchannel.

FIG. 52 is a schematic illustration of repeating unit 202D which comprises process microchannel 210, staged addition channel 280, and a plurality of heat exchange channels 296. The process microchannel 210 contains a reaction zone 210 containing a catalyst supporting support strip 400A. The staged addition channel 280 and the process microchannel 210 have a common wall 281 with an apertured section 290 positioned in the common wall. A feed composition comprising ethylbenzene flows in the process microchannel as indicated by arrow 220. A staged addition feed stream comprising oxygen flows from the staged addition channel 280 through the apertured section 290 into the process microchannel 210 where it contacts and mixes with the feed composition. The oxygen and ethylbenzene react in the presence of the catalyst to form styrene. Heat exchange fluid flows in the heat exchange channels 296 in a direction that is cross-current relative to the direction of flow of process fluids in the process microchannel 210.

Figure 53:
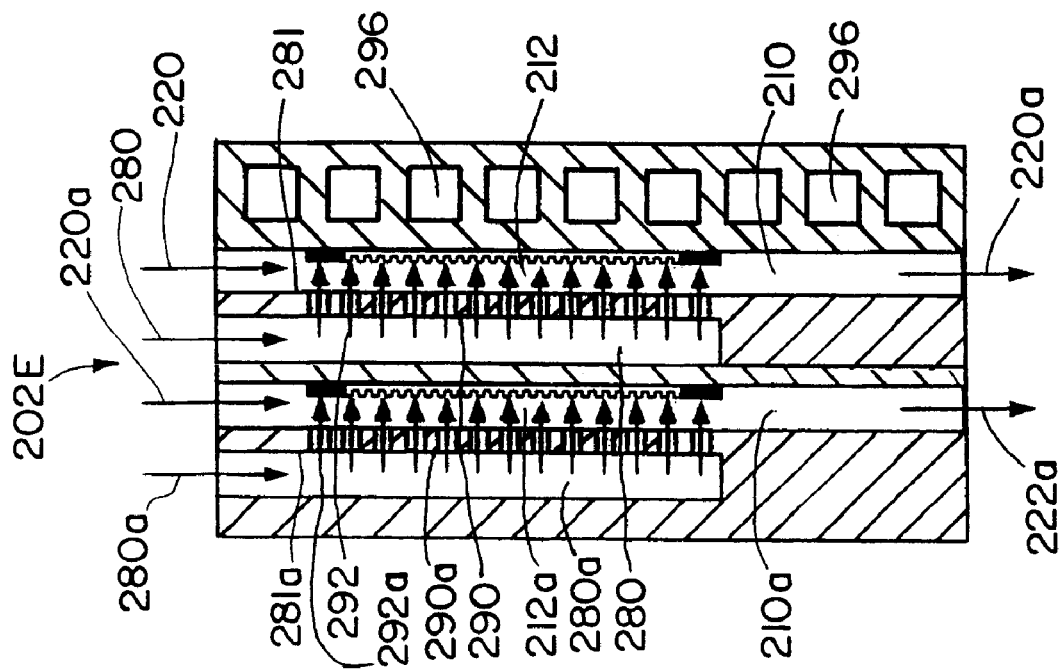
FIG. 53 is a schematic illustration of a repeating unit that is similar to the repeating unit illustrated in FIG. 52 with the exception that the repeating unit illustrated in FIG. 53 contains two adjacent sets of process microchannels, staged addition channels and apertured sections. One of these sets is adjacent to the heat exchange channels while the other set is in thermal contact with the heat exchange channels.

FIG. 53 is a schematic illustration of repeating unit 202E that is similar to the repeating unit 202D illustrated in FIG. 52 with the exception that the repeating unit 202E contains two adjacent sets of process microchannels, staged addition channels and apertured sections. One of these sets is adjacent to the heat exchange channels 296 while the other set is in thermal contact with the heat exchange channels 296.

The microchannel reactor core 110 including the process microchannels, optional staged addition channels, and heat exchange channels, as well as any process headers, process footers, heat exchange headers or heat exchange footers, and structured wall strips or shims, may be made of any material that provides sufficient strength, dimensional stability and heat transfer characteristics to permit operation of the inventive process. These materials include steel; aluminum, titanium; nickel, platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The microchannel reactor core 110 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel reactor core 110 may be constructed by forming layers or sheets with portions removed that allow flow passage. A stack of sheets may be assembled via diffusion bonding, laser welding, diffusion brazing, and similar methods to form an integrated device. The microchannel reactor core 110 may be assembled using a combination of sheets or laminae and partial sheets or strips. In this method, the channels or void areas may be formed by assembling strips or partial sheets to reduce the amount of material required.

In one embodiment, subsections or modular units of the microchannel reactor core 110 may be fabricated using the following components: a substrate piece with a hermetically sealed perimeter and open top/bottom for process flow; and a heat exchange piece. The substrate piece and heat exchange piece may be joined (welded, glued, soldered, etc.) to form a leak-free operating unit. The heat exchange piece may be extruded. The substrate piece and the heat exchange piece may be made from plastic, metal, or other materials as discussed above.

In one embodiment, the microchannel reactor core 110 may be made by a process that comprises laminating or diffusion bonding shims made of any of the above-indicated materials (e.g., metal, plastic or ceramic) so that each layer has a defined geometry of channels and openings through which to convey fluids. After the individual layers have been created, the microgrooved support strips and/or composite support structures may be inserted and the desired catalyst or sorption medium may be applied to the microgrooved support strips and/or composite support structures. The catalyst or sorption medium may be applied to the microgrooved support strips and/or composite support structures prior to inserting the support strips into the desired process microchannels. The layers may then be stacked in a prescribed order to build up the lamination. The layers may be stacked side-by-side or one above the other. The completed stack may then be diffusion bonded to prevent fluids from leaking into or out of the microchannel reactor or microchannel separator. After bonding, the device may be trimmed to its final size and prepared for attachment of pipes and manifolds.

Feature creation methods include photochemical etching, milling, drilling, electrical discharge machining, laser cutting, and stamping. A useful method for mass manufacturing is stamping. In stamping, care should be taken to minimize distortion of the material and maintain tight tolerances of channel geometries. Preventing distortion, maintaining shim alignment and ensuring that layers are stacked in the proper order are factors that should be controlled during the stacking process.

The stack may be bonded through a diffusion process. In this process, the stack may be subjected to elevated temperatures and pressures for a precise time period to achieve the desired bond quality. Selection of these parameters may require modeling and experimental validation to find bonding conditions that enable sufficient grain growth between metal layers.

The next step, after bonding, may be to machine the device. A number of processes may be used, including conventional milling with high-speed cutters, as well as highly modified electrical discharge machining techniques. A full-sized bonded microchannel reactor or microchannel separator unit or sub-unit that has undergone post-bonding machining operations may comprise, for example, tens, hundreds or thousands of shims.

The microchannel reactor 100 may have appropriate manifolds, valves, conduit lines, etc. to control flow of the process fluid, and the flow of the heat exchange fluid. These are not shown in the drawings, but can be readily provided by those skilled in the art.

The staged addition channels 280 and 280A may be microchannels or they may have larger dimensions. The process microchannels 210 and the staged addition channels 280 and 280A may have cross sections with any shape, for example, a square, rectangle, circle, semi-circle, etc. Each process microchannel 210 and staged addition channel 280 and 280A may have an internal height or gap of up to about 10 mm, and in one embodiment up to about 6 mm, and in one embodiment up to about 4 mm, and in one embodiment up to about 2 mm. In one embodiment, the height or gap may be in the range of about 0.05 to about 10 mm, and in one embodiment about 0.05 to about 6 mm, and in one embodiment about 0.05 to about 4 mm, and in one embodiment about 0.05 to about 2 mm. The width of each process microchannel 210 and staged addition channel 280 and 280A may be of any dimension, for example, up to about 3 meters, and in one embodiment about 0.01 to about 3 meters, and in one embodiment about 0.1 to about 3 meters. The length of each process microchannel 210 and staged addition channel 280 and 280A may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters.

The heat exchange channels 260, 295 and 296 may be microchannels or they may have larger dimensions. Each of the heat exchange channels 260, 295 and 296 may have a cross section having any shape, for example, a square, rectangle, circle, semi-circle, etc. Each of the heat exchange channels 260, 295 and 296 may have an internal height or gap of up to about 10 mm, and in one embodiment in the range of about 0.05 to about 10 mm, and in one embodiment from about 0.05 to about 5 mm, and in one embodiment from about 0.05 to about 2 mm. The width of each of these channels may be of any dimension, for example, up to about 3 meters, and in one embodiment from about 0.01 to about 3 meters, and in one embodiment about 0.1 to about 3 meters. The length of each of the heat exchange channels 260, 295 and 296 may be of any dimension, for example, up to about 10 meters, and in one embodiment from about 0.1 to about 10 meters, and in one embodiment from about 0.2 to about 6 meters, and in one embodiment from 0.2 to about 3 meters.

In one embodiment, the process microchannels and heat exchange channels used in the microchannel reactor core 110 may have rectangular cross sections and be aligned in side-by-side vertically oriented planes or horizontally oriented stacked planes. These planes may be tilted at an inclined angle from the horizontal. These configurations may be referred to as parallel plate configurations. Various combinations of two or more process microchannels with a single heat exchange channel, or two or more heat exchange channels in combination with a single process microchannel may be employed. An array of these rectangular channels may be arranged in a modularized compact unit for scale-up.

The cross-sectioned shape and size of the process microchannels may vary along their axial length to accommodate changing hydrodynamics of the reaction. For example, if the reaction is an oxidative dehydrogenation reaction and one of the reactants is in excess, the fluidic properties of the reaction mixture may change over the course of the reaction. Surface features may be used to provide a different geometry, pattern, angle, depth, or ratio of size relative to the cross-section of the microchannel along its axial length to accommodate these hydrodynamic changes.

The separation between each process microchannel or staged addition channel and the next adjacent heat exchange channel may be in the range from about 0.05 mm to about 50 mm, and in one embodiment about 0.1 to about 10 mm, and in one embodiment about 0.2 mm to about 2 mm.

Figure 61:
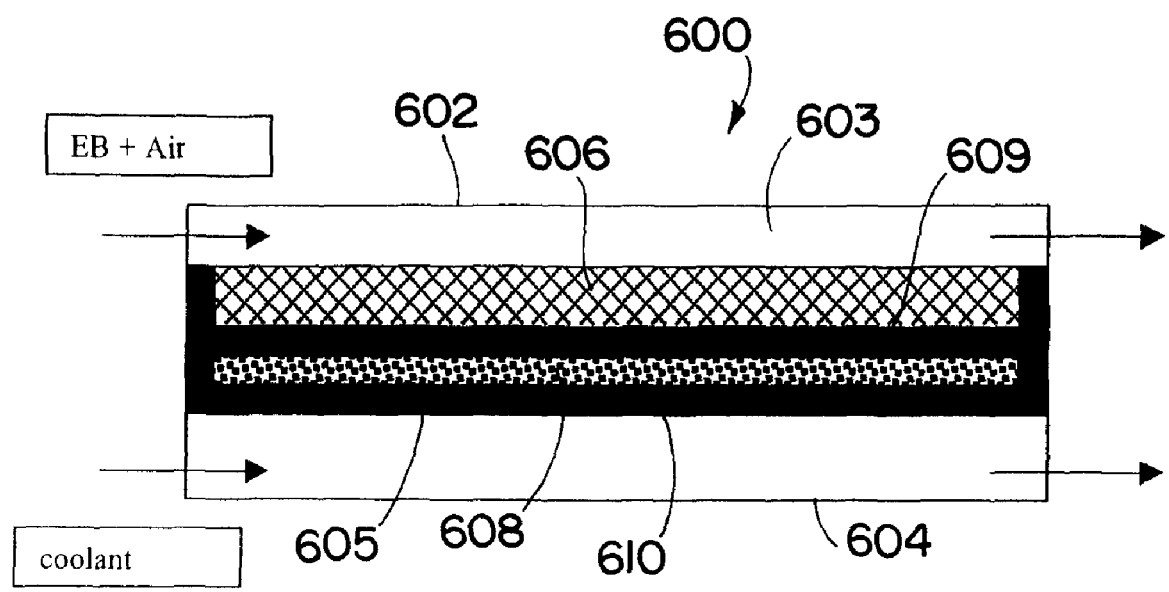
FIG. 61 is a schematic illustration of an apparatus which comprises a process microchannel, a heat exchange channel and a heat transfer wall positioned between the process microchannel and heat exchange channel, the heat transfer wall comprising a thermal resistance layer.

The invention may relate to an apparatus, comprising: a process microchannel; a heat exchange channel; and a heat transfer wall positioned between the process microchannel and the heat exchange channel, the heat transfer wall comprising at least one thermal resistance layer. The thermal resistance layer may be positioned on either or both sides of the heat transfer wall and/or embedded in the heat transfer wall. The apparatus, which is illustrated in FIG. 61, may be used as a repeating unit within the microchannel reactor 100. Referring to FIG. 61, the apparatus, which may be referred to as repeating unit 600, comprises process microchannel 602 and heat exchange channel 604. Heat transfer wall 605 is positioned between the process microchannel 602 and heat exchange channel 604. The process microchannel 602 includes bulk flow region 603 and structured wall 606 which may be used to support a catalyst. Thermal resistance layer 608 may be embedded within the heat transfer wall 605 as illustrated in FIG. 61. Alternatively or additionally, the thermal resistance layer 608 may be positioned on the process microchannel side of the heat transfer wall 605 and/or on the heat exchange channel side of the heat transfer wall 605. The thermal resistance layer 608 may have the same construction as the structured wall 606 (except that no catalyst is present). The thermal resistance layer 608 may be separated from the interior of the process microchannel 602 by wall 609 and from the interior of the heat exchange channel 604 by wall 610. In FIG. 61 only half the process microchannel 602 is shown. The other half of the process microchannel may comprise a second structured wall for supporting a catalyst. The second half of the process microchannel may comprise a second heat transfer wall 605 including a second thermal resistance layer 608. A second heat exchange channel may be provided on the other side of the process microchannel 602. A staged addition channel may be positioned adjacent the process microchannel 602.

The heat exchange channel 604 may be a microchannel or it may have a larger dimension. The process microchannel 602 and the heat exchange channel 604 may each have an internal height or gap of up to about 10 mm, and in one embodiment in the range of about 0.05 to about 10 mm, and in one embodiment from about 0.05 to about 5 mm, and in one embodiment from about 0.05 to about 2 mm. The width of each of these channels may be of any dimension, for example, up to about 3 meters, and in one embodiment from about 0.01 to about 3 meters, and in one embodiment about 0.1 to about 3 meters. The length of each of the these channels may be of any dimension, for example, up to about 10 meters, and in one embodiment from about 0.1 to about 10 meters, and in one embodiment from about 0.2 to about 6 meters, and in one embodiment from 0.2 to about 3 meters. The heat transfer wall may have a thickness in the range from about 0.05 to about 5 mm, and in one embodiment from about 0.05 to about 4 mm, and in one embodiment from about 0.05 to about 3 mm, and in one embodiment from about 0.05 to about 2 mm, and in one embodiment from about 0.05 to about 1.5 mm, and in one embodiment from about 0 to about 1 mm. The thermal resistance layer 608 may have a thickness in the range from about 1 to about 99% of the thickness of the heat transfer wall 605, and in one embodiment from about 1 to about 80%, and in one embodiment from about 1 to about 50%, and in one embodiment from about 1 to about 30%, and in one embodiment from about 1 to about 20%, and in one embodiment from about 1 to about 10%.

The process microchannel 602, heat exchange channel 604, heat transfer wall 605, and thermal resistance layer 608 may independently be made of a material comprising: steel; monel; inconel; aluminum; titanium; nickel; copper; brass; an alloy of any of the foregoing metals; ceramics; glass; quartz; silicon; or a combination of two or more thereof.

The construction and/or material of construction of the thermal resistance layer 608 may comprise any construction and/or material of construction having a different thermal conductivity than the thermal conductivity of the heat transfer wall 605. The thermal resistance layer 608 may comprise a vacuum, a gaseous material, a liquid and/or a solid material embedded in the heat transfer wall 605. The solid material may contain void spaces, openings and/or through holes. The thermal resistance layer may comprise one or more strips or shims which may contain void spaces, openings and/or through holes. The thermal resistance layer may comprise one or more strips with grooves or microgrooves formed in the strip. The thermal resistance layer may comprise one or more shims, each of the shims having a first surface and a second surface, and grooves or microgrooves formed in the first surface and/or the second surface.

The thermal resistance layer 608 and/or heat transfer wall 605 may comprise one or more sub-assemblies of a thermal resistant construction. Each sub-assembly may comprise two or more shims stacked one above another with one or more void spaces positioned between the shims. The void spaces may comprise a vacuum, air or an inert gas. The thermal resistance layer 608 and/or heat transfer wall 605 may comprise any desired number of these sub-assemblies stacked one above another, for example, from 1 to about 100 sub-assemblies, and in one embodiment from 1 to about 50 sub-assemblies, and in one embodiment from 1 to about 20 sub-assemblies, and in one embodiment from 1 to about 10 sub-assemblies, and in one embodiment from 1 to about 5 sub-assemblies, and in one embodiment from 1 to about 3 sub-assemblies, and in one embodiment 1 or 2 sub-assemblies.

The structured wall 606 and the thermal resistance layer 608 may be constructed by stacking a plurality of the shims illustrated in FIGS. 59 and 60 one above another. The shims used to form the structured wall 606 and thermal resistance layer 608 may independently have alternating patterns such that a porous structure may be created when the shims are stacked together to form the structured wall 606 and/or thermal resistance layer 608. The openings in the alternating shims may be arranged to create solid metal connections through the stack of shims along with completely open large pores through the stack to facilitate rapid diffusion. There may be cross members that extend from the solid metal connections through some of the open porous area to further increase the internal surface area. The openings in the structured wall 606 and/or thermal resistance layer 608 may vary from about 25 microns to about 500 microns, and in one embodiment from about 50 to about 250 microns.

The mass of reactants may diffuse and to some extent flow within the open porous structure of the structured wall 606. The catalyst may coat part of or the entire surface area of the structured wall 606.

The bulk flow region 603 in the process microchannel may reduce the impediment to flow resistance and allow the reactants to diffuse into the open structured walls 606 to access the catalyst.

In one embodiment, the heat transfer wall 605 may form an interior wall of the process microchannel 602 and one or more shims may be positioned on said interior wall to form structured wall 606, the one or more shims containing void spaces, openings or through holes. A catalyst may be supported by the one or more shims.

The microchannel reactor 100 may comprise one or more of the repeating units 600. In one embodiment, the microchannel reactor may comprise from 1 to about 50,000 of the repeating units 600, and in one embodiment from about 10 to about 50,000 of the repeating units 600, and in one embodiment from about 10 to about 30,000 repeating units, and in one embodiment from about 10 to about 10,000 of the repeating units 600, and in one embodiment from about 10 to about 5000 repeating units 600, and in one embodiment from about 10 to about 2000 repeating units 600, and in one embodiment from about 10 to about 1000 repeating units 600, and in one embodiment from about 10 to about 500 repeating units 600, and in one embodiment from about 10 to about 100 repeating units 600.

Figure 77:
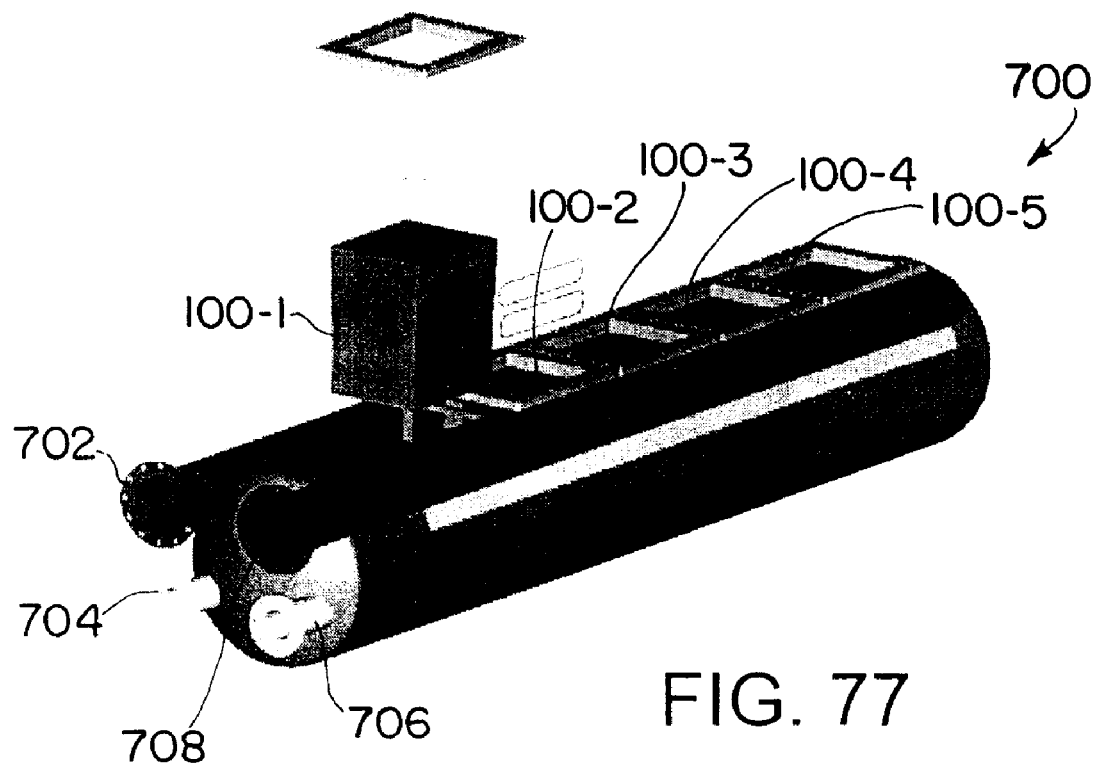
FIGS. 77 and 78 are schematic illustrations of a pressurizable vessel that may be used for housing microchannel reactors provided for in accordance with the invention.
Figure 78:
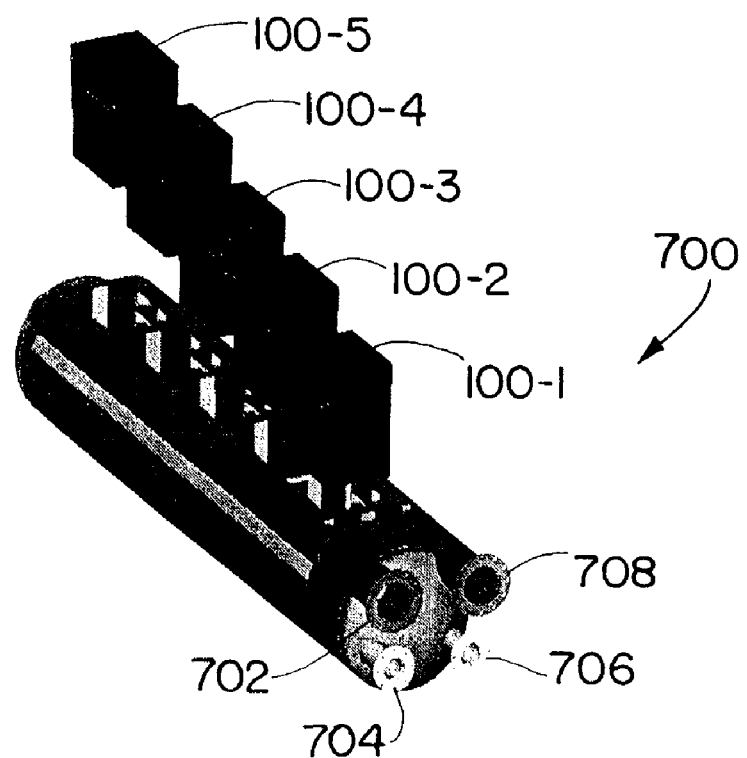

A plurality of the microchannel reactors 100 may be housed in vessel 700 which is illustrated in FIGS. 77 and 78. Referring to FIGS. 77 and 78, the vessel 700 contains five microchannel reactors 100. These are identified in FIGS. 77 and 78 as microchannel reactors 100-1, 100-2, 100-3, 100-4 and 100-5. Although five microchannel reactors 100 are disclosed in the drawings, it will be understood that the vessel 700 may contain any desired number of microchannel reactors. For example, the vessel 700 may contain from 1 to about 1000 microchannel reactors 100, and in one embodiment from about 3 to about 500 microchannels reactors 100, and in one embodiment from about 3 to about 250 microchannel reactors 100, and in one embodiment from about 3 to about 150 microchannel reactors 100, and in one embodiment from about 5 to about 50 microchannel reactors 100, and in one embodiment from about 5 to about 12 microchannel reactors 100. In one embodiment, the vessel 700 may contain from 1 to about 50 microchannel reactors 100, and in one embodiment from 1 to about 20 microchannel reactors 100. Each microchannel reactor 100 may comprise from about 1 to about 50,000 process microchannels, and in one embodiment from about 10 to about 50,000 process microchannels, and in one embodiment from about 10 to about 30,000, and in one embodiment from about 10 to about 10,000 process microchannels. The vessel 700 may be a pressurizable vessel. The vessel 700 includes inlets 702 and 704, and outlets 706 and 708. The inlet 702 is connected to a manifold which may be provided for flowing the ethylbenzene feed to the process microchannels in the microchannel reactors 100-1, 100-2, 100-3, 100-4 and 100-5. The inlet 704 is connected to a manifold which may be provided for flowing heat exchange fluid to the heat exchange channels in the microchannel reactors 100-1, 100-2, 100-3, 100-4 and 100-5. The outlet 706 is connected to a manifold which may be provided for flowing product from the microchannel reactors 100-1, 100-2, 100-3, 100-4 and 100-5 out of the vessel 700. The inlet 708 is connected to a manifold which may provide for the flow of the oxygen or source of oxygen (e.g., air) to staged addition channels that may be in the microchannel reactors 100-1, 100-2, 100-3, 100-4 and 100-5. The vessel 700 also includes an outlet (not shown in the drawings) providing for the flow of heat exchange fluid from the microchannel reactors 100-1, 100-2, 100-3, 100-4 and 100-5.

The vessel 700 may be constructed from any suitable material sufficient for operating under the pressures and temperatures required for operating the microchannel reactors. For example, the shell and heads of the vessels 700 may be constructed of cast steel. The flanges, couplings and pipes may be constructed of stainless steel or other suitable alloys. The vessel 700 may have any desired diameter, for example, from about 30 to about 500 cm, and in one embodiment from about 100 to about 300 cm. The axial length of the vessel 700 may be of any desired value, for example, from about 0.5 to about 50 meters, and in one embodiment from about 0.5 to about 15 meters, and in one embodiment from about 1 to about 10 meters.

As indicated above, the microchannel reactors 100 may comprise a plurality of process microchannels, heat exchange channels and optionally staged addition channels stacked one above the other or positioned side-by-side. The microchannel reactors 100 may be in the form of cubic blocks as illustrated in FIGS. 77 and 78. Each of these cubic blocks may have a length, width and height. The length may be in the range from about 10 to about 1000 cm, and in one embodiment in the range from about 50 to about 200 cm. The width may be in the range from about 10 to about 1000 cm, and in one embodiment in the range from about 50 to about 200 cm. The height may be in the range from about 10 to about 1000 cm, and in one embodiment in the range from about 50 to about 200 cm.

In one embodiment, the reaction zone 212 in the process microchannel 210 may be characterized by having a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel 210 may have a cross-sectional area of about 0.05 to about 10,000 mm$^2$, and in one embodiment about 0.05 to about 5000 mm$^2$, and in one embodiment about 0.1 to about 2500 mm$^2$. The bulk flow regions may comprise from about 5% to about 95%, and in one embodiment about 30% to about 80% of the cross-section of the process microchannels.

In one embodiment of the invention relatively short contact times, high selectivity to the desired product and relatively low rates of deactivation of the catalyst may be achieved by limiting the diffusion path required for the catalyst. For example, this may be achieved when the catalyst is in the form of a thin layer on an engineered support such as a metallic foam or on the wall of the process microchannel. This allows for increased space velocities. In one embodiment, the thin layer of catalyst can be produced using chemical vapor deposition. This thin layer may have a thickness in the range up to about 1 micron, and in one embodiment from about 0.1 to about 1 micron, and in one embodiment about 0.25 micron. These thin layers may reduce the time the reactants are within the active catalyst structure by reducing the diffusional path. This decreases the time the reactants spend in the active portion of the catalyst. The result may be increased selectivity to the product and reduced unwanted by-products. An advantage of this mode of catalyst deployment is that, unlike conventional catalysts in which the active portion of the catalyst may be bound up in an inert low thermal conductivity binder, the active catalyst film is in intimate contact with either the engineered structure or the wall of the process microchannel. This may leverage high heat transfer rates attainable in the microchannel reactor and allows for close control of temperature. The result is the ability to operate at increased temperature (faster kinetics) without promoting the formation of undesired by-products, thus producing higher productivity and yield and prolonging catalyst life.

In one embodiment, the catalyst may be regenerated. This may be done by flowing a regenerating fluid through the process microchannels in contact with the catalyst. The regenerating fluid may comprise hydrogen or a diluted hydrogen stream. The diluent may comprise nitrogen, argon, steam, methane, carbon dioxide, or a mixture of two or more thereof. The concentration of $H_2$ in the regenerating fluid may range up to about 100% by volume, and in one embodiment from about 1 to about 100% by volume, and in one embodiment about 1 to about 50% volume. The regenerating fluid may flow from the header through the process microchannels to the footer, or in the opposite direction from the footer through the process microchannels to the header. The temperature of the regenerating fluid may be from about 20 to about 600° C., and in one embodiment about 20 to about 400° C., and in one embodiment about 80 to about 200° C. The pressure within the process microchannels during this regeneration step may range from about 1 to about 100 atmospheres absolute pressure, and in one embodiment about 1 to about 10 atmospheres. The residence time for the regenerating fluid in the process microchannels may range from about 0.001 to about 10 seconds, and in one embodiment about 0.01 second to about 1 second.

The contact time of the process fluids with the catalyst within the process microchannels may be in the range up to about 100 seconds, and in one embodiment in the range from about 1 millisecond (ms) to about 100 seconds, and in one embodiment in the range from about 1 ms to about 50 seconds, and in one embodiment in the range from about 1 ms to about 25 seconds, and in one embodiment in the range from about 1 ms to about 10 seconds, and in one embodiment from about 1 ms to about 1 second, and in one embodiment from about 1 ms to about 500 ms, and in one embodiment about 1 ms to about 200 ms, and in one embodiment about 1 ms to about 100 ms, and in one embodiment about 1 ms to about 50 ms, and in one embodiment about 1 ms to about 20 ms, and in one embodiment about 1 ms to about 10 ms. In one embodiment, the reactants may be combined with up to about 50% by volume diluent (e.g., nitrogen gas) and the contact time may be up to about 25 seconds, and in one embodiment up to about 10 seconds, and in one embodiment up to about 1 second. In one embodiment, the reactants may be combined with up to about 25% by volume diluent and the contact time may be up to about 50 seconds, and in one embodiment up to about 25 seconds, and in one embodiment up to about 5 seconds. In one embodiment, the reactants may be combined with up to about 10% by volume diluent and the contact time may be up to about 100 seconds, and in one embodiment up to about 50 seconds, and in one embodiment up to about 10 seconds.

The flow rate of process fluid flowing in the process microchannels may be in the range from about 0.001 to about 500 lpm, and in one embodiment about 0.001 to about 250 lpm, and in one embodiment about 0.001 to about 100 lpm, and in one embodiment about 0.001 to about 50 lpm, and in one embodiment about 0.001 to about 25 lpm, and in one embodiment about 0.01 to about 10 lpm. The velocity of fluid flowing in the process microchannels may be in the range from about 0.01 to about 200 m/s, and in one embodiment about 0.01 to about 75 m/s, and in one embodiment about 0.01 to about 50 m/s, and in one embodiment about 0.01 to about 30 m/s, and in one embodiment about 0.02 to about 20 m/s. The Reynolds Number for the fluid flowing in the process microchannels may be in the range from about 0.0001 to about 100000, and in one embodiment about 0.001 to about 10000.

The space velocity (or gas hourly space velocity (GHSV)) for the flow of the process fluids in the process microchannels may be at least about 1000 $hr^{-1}$ (normal liters of feed per hour per liter of volume within the process microchannels), and in one embodiment at least about 2000 $hr^{-1}$, and in one embodiment at least about 4000 $hr^{-1}$, and in one embodiment at least about 7000 $hr^{-1}$, and in one embodiment at least about 10000 $hr^{-1}$. The space velocity may be in the range from about 1000 to about 500000 $hr^{-1}$, and in one embodiment in the range from about 4000 to about 40000 $hr^{-1}$. The volume within the process microchannels may include all volume in the process microchannels in which a process fluid may flow in a flow-through manner or a flow-by manner. The volume may include the volume within any microgrooved supports positioned in the microchannels as well as the volume within any surface features that may be present in the process microchannels.

The management of heat exchange with the inventive process may provide advantageous control of the conversion of ethylbenzene and the selectivity to styrene. The heat exchange channels may be adapted for heat exchange fluid to flow in the heat exchange channels in a direction that is co-current with the flow of fluid in process microchannels and/or staged addition channels that are adjacent to or in thermal contact with the heat exchange channels. Alternatively, the heat exchange fluid may flow through the heat exchange channels in a direction that is countercurrent to the flow of fluid through the process microchannels and/or staged addition channels. Alternatively, the heat exchange channels may be oriented relative to the process microchannels and/or staged addition channels to provide for the flow of heat exchange fluid in a direction that is cross-current relative to the flow of fluid through the process microchannels and/or staged addition channels. The heat exchange channels may have a serpentine configuration to provide a combination of cross-flow and co-current or counter-current flow.

The heat exchange fluid may be any fluid. These include air, steam, liquid water, gaseous nitrogen, liquid nitrogen, other gases including inert gases, carbon monoxide, carbon dioxide, oils such as mineral oil, gaseous hydrocarbons, liquid hydrocarbons, and heat exchange fluids such as Dowtherm A and Therminol which are available from Dow-Union Carbide. The heat exchange fluid may comprise one or more organic compounds containing 1 to about 5 carbon atoms per molecule such as methylenechloride, fluorochloromethanes (e.g., dichlordifluoromethane), hydrocarbons containing 1 to about 5 carbon atoms per molecule (e.g., methane, ethane, ethylene, propanes, butanes, pentanes, etc.), or a mixture of two or more thereof.

The heat exchange fluid may comprise the feed composition, staged addition feed stream and/or product. This can provide process pre-heat, cool-down and/or an increase in overall thermal efficiency of the process.

In one embodiment, the heat exchange channels may comprise process channels wherein an endothermic or exothermic process is conducted. These heat exchange process channels may be microchannels. Examples of endothermic processes that may be conducted in the heat exchange channels include steam reforming and dehydrogenation reactions. Examples of exothermic processes that may be conducted in the heat exchange channels include water-gas shift reactions, methanol synthesis reactions and ammonia synthesis reactions.

In one embodiment, the heat exchange fluid undergoes a phase change in the heat exchange channels. This phase change provides additional heat addition to or removal from the process microchannels and/or second reactant stream channels beyond that provided by convective heating or cooling. An example of such a phase change would be an oil or water that undergoes boiling.

In one embodiment, the vapor mass fraction quantity of the boiling of the phase change fluid may be up to about 100%, and in one embodiment up to about 75%, and in one embodiment up to about 50%, and in one embodiment in the range from about of 1% to about 50%.

The pressure within each individual heat exchange channel may be controlled using passive structures (e.g., obstructions), orifices and/or mechanisms upstream of the heat exchange channels or in the channels. By controlling the pressure within each heat exchange channel, the temperature within each heat exchange channel can be controlled. A higher inlet pressure for each heat exchange fluid may be used where the passive structures, orifices and/or mechanisms let down the pressure to the desired heat exchange microchannel pressure. By controlling the temperature within each heat exchange channel, the temperature in the process microchannels in thermal contact with the heat exchange microchannel can be controlled. Thus, for example, each process microchannel may be operated at a desired temperature by employing a specific pressure in the heat exchange channel in thermal contact with the process microchannel. This may provide the advantage of precisely controlled temperatures for each process microchannel. The use of precisely controlled temperatures for each process microchannel may provide the advantage of a tailored temperature profile and an overall reduction in the energy requirements for the reaction process.

The heat flux for heat exchange in the microchannel reactor may be in the range from about 0.01 to about 500 watts per square centimeter ($W/cm^2$) of the surface area of the heat transfer walls in the microchannel reactor, and in one embodiment from about 0.01 to about 250 $W/cm^2$. The heat flux may be in the range from about 0.01 to about 125 $W/cm^2$, and in one embodiment about 0.1 to about 50 $W/cm^2$, and in one embodiment from about 0.1 to about 10 $W/cm^2$. The heat flux may be in the range from about 1 to about 500 $W/cm^2$, and in one embodiment from about 1 to about 250 $W/cm^2$, and in one embodiment, from about 1 to about 100 $W/cm^2$, and in one embodiment from about 1 to about 50 $W/cm^2$, and in one embodiment from about 1 to about 25 $W/cm^2$, and in one embodiment from about 1 to about 10 $W/cm^2$.

In one embodiment, the temperature of the reactant streams entering the microchannel reactor may be within about 200° C., and in one embodiment within about 100° C., and in one embodiment within about 50° C., and in one embodiment within about 20° C., of the temperature of the product exiting the microchannel reactor.

The use of controlled heat exchange between heat exchange channels in thermal contact with or adjacent to the process microchannels and/or staged addition channels may allow for uniform temperature profiles for the process microchannels and/or staged addition channels. This provides for the possibility of a more uniform heat exchange at more rapid rates than can be obtained with conventional processing equipment such as mixing tanks. For a microchannel reactor employing multiple process microchannels and staged addition channels, the temperature difference between the process microchannels and/or staged addition channels at least one common position along the lengths of the process microchannels may be less than about 5° C., and in one embodiment less than about 2° C., and in one embodiment less than about 1° C.

The heat exchange channels in thermal contact with or adjacent to either the process microchannels and/or staged addition channels may employ separate temperature zones along the length of such channels. For example, in one embodiment, the temperature in a first zone near the entrance to the process microchannel may be maintained at a temperature above or below a second temperature in a second zone near the end of the process microchannel. A cool down or quench zone may be incorporated into the process microchannels to cool the product. Numerous combinations of thermal profiles are possible, allowing for a tailored thermal profile along the length of the process microchannels and/or staged addition channels, including the possibility of heating or cooling zones before and/or after the reaction zone in the process microchannels to heat or cool the reactants and/or product.

The heat exchange fluid entering the heat exchange channels may be at a temperature in the range from about 50° C. to about 650° C., and in one embodiment in the range from about 150° C. to about 600° C., and in one embodiment in the range from about 250° C. to about 500° C. The heat exchange fluid exiting the heat exchange channels may be at a temperature in the range from about 100° C. to about 700° C., and in one embodiment in the range from about 200° C. to about 650° C., and in one embodiment in the range from about 300° C. to about 550° C. The residence time of the heat exchange fluid in the heat exchange channels may be in the range from about 5 ms to about 1 minute, and in one embodiment from about 20 ms to about 1 minute, and in one embodiment from about 50 ms to about 1 minute, and in one embodiment about 100 ms to about 1 minute. The pressure drop for the heat exchange fluid as it flows through the heat exchange channels may be in the range up to about 1 atm/m, and in one embodiment up to about 0.5 atm/m, and in one embodiment up to about 0.1 atm/m, and in one embodiment from about 0.01 to about 1 atm/m. The heat exchange fluid may be in the form of a vapor, a liquid, or a mixture of vapor and liquid. The Reynolds Number for the flow of vapor through the heat exchange channels may be in the range from about 10 to about 5000, and in one embodiment about 100 to about 3000. The Reynolds Number for the flow of liquid through heat exchange channels may be in the range from about 10 to about 10000, and in one embodiment about 100 to about 5000.

The temperature of the reactants entering the microchannel reactor reactor core 110 may be in the range up to about 600° C., and in one embodiment in the range from about 150° C. to about 600° C., and in one embodiment from about 250° C. to about 550° C.

The temperature within the process microchannels for a dehydrogenation reaction process may be in the range from about 650° C. to about 900° C., and in one embodiment from about 700° C. to about 850° C. The temperature within the process microchannels for an oxidative dehydrogenation reaction process may be in the range from about 250° C. to about 650° C., and in one embodiment from about 350° C. to about 550° C., and in one embodiment from about 400° C. to about 500° C.

The temperature of the product exiting the microchannel reactor core 110 may be in the range up to about 650° C., and in one embodiment in the range from about 150° C. to about 650° C., and in one embodiment from about 200° C. to about 600° C., and in one embodiment from about 250° C. to about 550° C.

The pressure within the process microchannels may be in the range up to about 50 atmospheres absolute pressure, and in one embodiment up to about 40 atmospheres, and in one embodiment up to about 30 atmospheres. In one embodiment the pressure may be in the range from about 1 to about 50 atmospheres absolute pressure, and in one embodiment from about 10 to about 40 atmospheres, and in one embodiment from about 20 to about 30 atmospheres.

The pressure drop of the process fluids as they flow in the process microchannels may be in the range up to about 5 atmospheres per meter of length of the process microchannel (atm/m), and in one embodiment up to about 1 atm/m, and in one embodiment up to about 0.1 atm/m.

The pressure drop for the stage addition feed stream flowing through the apertured sections may be in the range up to about 0.1 atm, and in one embodiment from about 0.001 to about 0.1 atm, and in one embodiment from about 0.001 to about 0.05 atm, and in one embodiment about 0.001 to about 0.005 atm. The reactants and products flowing through the process microchannels may be in the form of a vapor, a liquid, or a mixture of vapor and liquid. The Reynolds Number for the flow of vapor through the process microchannels may be in the range from about 10 to about 10000, and in one embodiment about 100 to about 3000. The Reynolds Number for the flow of liquid through the process microchannels may be about 10 to about 10000, and in one embodiment about 100 to about 3000.

The conversion of the ethylbenzene may be in the range from about 25% or higher per cycle, and in one embodiment about 50% or higher per cycle, and in one embodiment from about 25 to about 100%, and in one embodiment from about 50% to about 100% per cycle. In one embodiment, the conversion may be at least about 70%.

The conversion of the oxygen, when used, may be in the range from about 40% or higher per cycle, and in one embodiment from about 40% to about 100% per cycle.

The yield of styrene may be in the range from about 20% or higher, and in one embodiment about 50% or higher, and in one embodiment from about 50% to about 99%.

The selectivity to styrene may be at least about 50%, and in one embodiment at least about 80%, and in one embodiment at least about 90%, and in one embodiment at least about 95%, and in one embodiment in the range from about 50% to about 99%, and in one embodiment in the range from about 80% to about 99%, and in one embodiment from about 95% to about 99%.

It may be possible to achieve a yield of styrene that is at least about 20% with less than about 20% change in the yield of styrene for a period of at least about 24 hours with a contact time of less than about 10 seconds and a feed composition containing less than about 50% by volume diluent (e.g., nitrogen gas). It may be possible to achieve a yield of styrene that is at least about 35%, and in one embodiment at least about 50%, and in one embodiment at least about 75% with less than about 20% change in the yield of styrene for at least about 24 hours with a contact time of less than about 10 seconds and a feed composition containing less than about 50% by volume diluent (e.g., nitrogen gas). In one of these embodiments, the contact time may be less than about 5 seconds, and in one embodiment less than about 2 seconds, and in one embodiment less than about 1 second. In one of these embodiments, the feed composition may contain less than about 25% by volume diluent, and in one embodiment less than about 10% by volume diluent.

It may be possible to produce styrene at a rate of at least about 500 ml per gram of catalyst per hour using the inventive process, and in one embodiment at least about 750 ml per gram of catalyst per hour, and in one embodiment at least about 900 ml per gram of catalyst per hour, and in one embodiment at least about 1000 ml per gram of catalyst per hour.

It may be possible to achieve a styrene yield that is at least about 20% with less than about 20% change in the styrene yield for at least about 24 hours wherein the styrene is produced at a rate of at least about 500 ml per gram of catalyst per hour. In one of these embodiments, the styrene yield may be at least about 35%, and in one embodiment at least about 50%, and in one embodiment at least about 75%. In one of these embodiments, the styrene may be produced at a rate of at least about 750 ml per gram of catalyst per hour, and in one embodiment at least about 900 ml per gram of catalyst per hour, and in one embodiment at least about 1000 ml per gram of catalyst per hour.

EXAMPLE 1

0.7% $K_2O$-15% $MoO_3/SiO_2$—$TiO_2$ catalyst is prepared by the sol-gel method. 20.0 g tetraethylorthosilicate and 27.29 g titanium isopropoxide are dissolved in 200 ml isopropyl alcohol solution with stirring. In another beaker, 2.93 g ammonium paramolybdate are dissolved in 13.65 g $H_2O$ and then 0.30 g 45% KOH solution are added. The aqueous solution is added dropwise to the alcohol solution (1 ml/min). After all of the aqueous solution is added, the resulting gel is stirred for additional 15 min. The gel is dried at 110° C. overnight and calcined at 550° C. for 5 hours. The catalyst is crushed and sieved to 60-100 mesh.

The catalyst (0.4 g) is loaded in a quartz tube reactor having a 0.2 inch O.D. (0.635 cm). The reactor volume is 0.3 ml. A feed gas composition containing 9.9% by volume ethylbenzene, 5% by volume $O_2$ and 85.1% by volume $N_2$ flows into the reactor. The feed gas flow rate is 180 ml/min. The contact time based on reactor volume is 0.1 second. The process operates for 3 hours with no evidence of catalyst deactivation. The process is operated at atmospheric pressure. The GHSV based on reactor volume is 36000 $hr^{-1}$. The GHSV based on the catalyst is 27000 ml/g-cat/hour. The GHSV for ethylbenzene based on catalyst is 2670 ml/g-cat/hour. The products are analyzed by GC. At 500° C., 43% ethylbenzene conversion and 91% styrene selectivity are achieved. The styrene yield is 39%. The styrene yield is 1041 ml/g-cat/hour. $O_2$ conversion is 98%.

EXAMPLE 2

0.7% $K_2O$-18% $V_2O_5/SiO_2$—$ZrO_2$ catalyst is prepared by the sol-gel method. 7.05 g vanadium (III) 2,4-pentanedionate are dissolved in 200 ml iso-butanol with stirring at 60° C. After cooling, 19.97 g zirconium n-butoxide are added at room temperature with stirring, followed by 15.0 g n-butoxysilane. In another beaker, 0.19 g 45% KOH solution are mixed with 6.63 g $H_2O$. The aqueous solution is added dropwise to the alcohol solution (1 ml./min). After all of the aqueous solution is added, the resulting mixture is stirred for an additional 15 min. The gel is then dried at 110° C. overnight and calcined at 550° C. for 5 hours. The catalyst is crushed and sieved to 60-100 mesh.

The catalyst (0.5 g) is loaded in the quartz tube reactor identified in Example 1. The feed gas composition contains 9.9% by volume ethylbenzene, 5% by volume $O_2$ and 85.1% by volume $N_2$. The contact time is 0.1 second. The process operates for 3 hours with no evidence of catalyst deactivation. The process is operated at atmospheric pressure. The products are analyzed by GC. At 450° C., 36% ethylbenzene conversion and 89% styrene selectivity are achieved. The styrene yield is 32%. $O_2$ conversion is 96%.

EXAMPLE 3

$Mg_{0.99}MoO_{3.99}$ catalyst is prepared by the sol-gel method. 16.00 g molybdenum (VI) oxide bis(2,4-pentanedionate) is dissolved in 200 ml methoxyethanol. 5.56 g magnesium ethoxide are then added with stirring. Subsequently, 14.13 g 2.5 mol/L $NH_4OH$ solution are added dropwise to the mixture. The resulting gel is dried at 110° C. for 5 hours and then calcined at 550° C. for 12 hours. The catalyst is crushed and sieved to 60-100 mesh.

The catalyst (0.3 g) is loaded in the quartz tube reactor identified in Example 1. The feed gas composition contains 9.9% by volume ethylbenzene, 5% by volume $O_2$ and 85.1% by volume $N_2$. The contact time is 0.1 second. The process operates for 4 hours with no evidence of catalyst deactivation. The process is conducted at atmospheric pressure. The products are analyzed by GC. At 500° C., 29% ethylbenzene conversion and 88% styrene selectivity are achieved. The styrene yield is 26%. $O_2$ conversion is 78%.

EXAMPLE 4

Mesoporous V—Mg—Ox (18% $V_2O_5$) catalyst is prepared by the co-precipitation method. 6.97 g vanadium (III) 2,4-pentanedionate are dissolved in 200 ml ethanol solution with stirring at 70° C. In another beaker, 19.59 g $MgCl_2$ and 9.03 g hexadecyltrimethylammonium chloride are dissolved in 200 ml $H_2O$. The vanadium solution is added into the $MgCl_2$ solution. The mixture is heated to 92-95° C. The pH is adjusted to 9 by 5 mol/L $NH_3.H_2O$ and then to 10 by 45 wt % KOH solution. The temperature is kept at 92-95° C. for 2 h. Subsequently, the slurry is cooled to room temperature and aged overnight. The mixture is filtered and the solid is washed with $H_2O$ three times. After drying at 110° C. overnight, the sample is calcined at 550° C. for 4 hours. The catalyst is crushed and sieved to 60-100 mesh.

The catalyst (0.2 g) is loaded in the quartz tube reactor identified in Example 1. The feed gas composition contains 9.9% by volume ethylbenzene, 5% by volume $O_2$ and 85.1% by volume $N_2$. The contact time is 0.1 second. The process operates for 4 hours with no evidence of catalyst deactivation. The process is conducted at atmospheric pressure. The products are analyzed by GC. At 550° C., 36% ethylbenzene conversion and 89% styrene selectivity are achieved. The styrene yield is 32%. $O_2$ conversion is 98%.

EXAMPLE 5

$V_2Mo_6O_{26}/MgO$ catalyst is prepared by the ion-exchange method. 1.66 g $KVO_3$ and 8.57 g $K_2MoO_4$ are dissolved in 300 ml $H_2O$. The pH of the solution is adjusted to 5.5 by HCl solution. After storing for 5 days, 1.45 g MgO powder are added into the solution and stirred for one day at room temperature. The mixture is filtered and the solid is washed with $H_2O$ three times. After drying at 110° C. overnight, the sample is calcined at 500° C. for 5 hours. The catalyst is sieved to 60-100 mesh.

The catalyst (0.16 g) is loaded in the quartz tube reactor identified in Example 1. The feed gas composition contains 9.9% by volume ethylbenzene, 5% by volume $O_2$ and 85.1% by volume $N_2$. The contact time is 0.1 second. The process operates for 5 hours with no evidence of catalyst deactivation. The process is conducted at atmospheric pressure. The products are analyzed by GC. At 550° C., 25% ethylbenzene conversion and 82% styrene selectivity are achieved. The styrene yield is 21%. $O_2$ conversion is 97%.

EXAMPLE 6

0.7% $K_2O$-15% $MoO_3/SiO_2$—$TiO_2$ catalyst is prepared by the sol-gel method. 20.0 g tetraethylorthosilicate and 27.29 g titanium isopropoxide are dissolved in 200 ml isopropyl alcohol solution with stirring. In another beaker, 2.93 g ammonium paramolybdate are dissolved in 13.65 g $H_2O$ and then 0.30 g 45% KOH solution are added. The aqueous solution is dropped slowly into the alcohol solution (1 ml/min). After all of the aqueous solution is added, the resulting gel is stirred for additional 15 min. The gel is dried at 110° C. overnight and calcined at 550° C. for 5 hours. The catalyst is crushed and sieved to 60-100 mesh.

Figure 37:
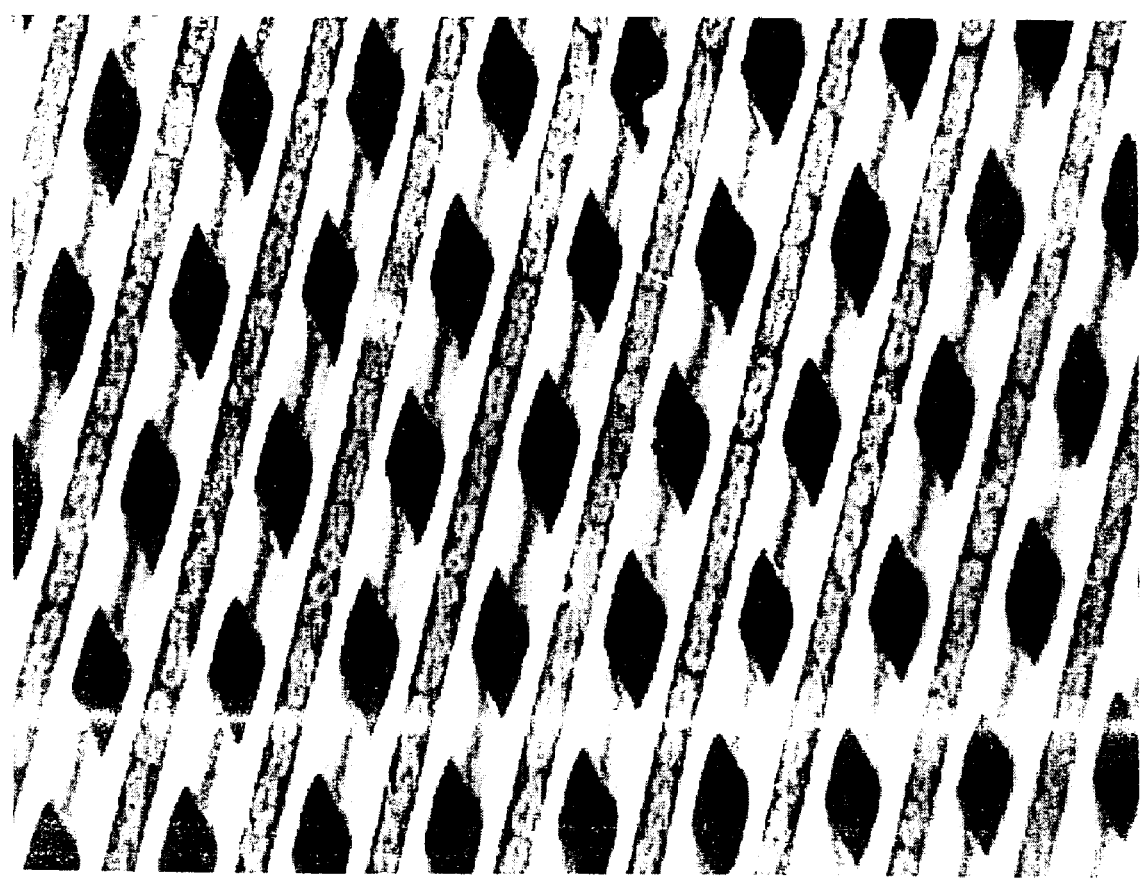
FIG. 37 is a microphotograph enlarged 50× showing a microgrooved support structure with catalyst particles deposited in the microgrooves of the microgrooved support structure, the microgrooved support structure being made of stainless steel 304, the catalyst comprising 0.7% $K_2O$-15% $MoO_3$/$SiO_2$—$TiO_2$.

The catalyst (5 g) is mixed with 45 g $H_2O$ and 95 g 6-mm $ZrO_2$ beads in a jar. The mixture is ball-milled for three days. The resulting slurry (10 wt %) is then diluted to 2.5 wt % by $H_2O$. The average particle size in the slurry is about 1 micron. The slurry is dropped onto the microgrooved support strip illustrated in FIG. 36 by pipette and then dried at 120° C. for 1 hour. The microgrooved support strip is made of stainless steel 304. The microgrooved support strip has a length of 2.500 inches (6.350 cm), a width of 0.500 inch (1.27 cm), and a thickness of 0.002 inch (50.8 microns). The microgrooves in the microgrooved support have a width of 0.007 inch (178 microns). The spacing between the microgrooves is 0.007 inch (178 microns). This washcoating procedure is repeated twelve times. The catalyst-coated microgrooved support strip is then calcined at 500° C. for 1 hour. The catalyst loading is 28.8 mg. A microphotograph (50×) of the catalyst coated microgrooved support strip is shown in FIG. 37.

The catalyst coated microgrooved support strip is welded in the microchannel device shown in FIG. 38. The microchannel device, which is fabricated with FeCrAlY, has internal volume of 0.039 ml.

A feed gas composition, which contains 18.8% ethylbenzene and 81.2% air, flows into the microchannel device. The feed gas flow rate is 2.93 ml/min. The ethylbenzene to oxygen molar ratio is 1.1. The contact time based on reactor volume is 0.8 second. The process is operated for 96 hours with no evidence of catalyst deactivation. The process is conducted at atmospheric pressure. The GHSV based on reactor volume is 4508 $hr^{-1}$. The GHSV based on the catalyst is 6104 ml/g-cat/hour. The GHSV for the ethylbenzene is 1148 ml/g-cat/hour. The products are analyzed by GC. At an average temperature of 412° C., 86% ethylbenzene conversion and 94% styrene selectivity are achieved. The styrene yield is 81%. The styrene yield is 930 ml/g-cat/hour. $O_2$ conversion is 98%.

The results of Examples 1-6 are summarized in Table I. For each of Examples 1-5, the feed stream contains 9.9% by volume ethylbenzene, 5% by volume oxygen, and 85.1% by volume nitrogen. For Example 6, the feed stream contains 18.8% by volume ethylbenzene, 17.1% by volume oxygen, and 64.1% by volume nitrogen.

TABLE 1

| Example | Catalyst | T(° C.) | EB conv. (%) | $O_2$ conv. (%) | Styrene Sel. (%) | Styrene Yield (%) | Time on steam (h) |
|---|---|---|---|---|---|---|---|
| 1 | 0.7% $K_2O$-15% $MoO_3/SiO_2$—$TiO_2$ | 450 | 38 | 91 | 90 | 34 | 3 |
|  |  | 500 | 43 | 98 | 91 | 39 |  |
| 2 | 0.7% $K_2O$-18% $V_2O_5/SiO_2$—$ZrO_2$ | 450 | 36 | 96 | 89 | 32 | 3 |
| 3 | $Mg_{0.99}MoO_{3.99}$ | 500 | 29 | 78 | 88 | 26 | 4 |
| 4 | Mesoporous V—Mg—O$x$ (18% $V_2O_5$) | 550 | 36 | 98 | 89 | 32 | 4 |
| 5 | $V_2Mo_6O_{26}$/MgO | 550 | 25 | 97 | 82 | 21 | 5 |
| 6. | 0.7% $K_2O$-15% $MoO_3/SiO_2$—$TiO_2$ coated on microgrooved support | 412 | 86 | 98 | 94 | 81 | 96 |

A comparison between the results for Examples 1 and 6 is provided in Table II:

TABLE II

|  | Example 1 | Example 6 |
|---|---|---|
| Catalyst weight (g) | 0.4 | 0.0288 |
| Reactor volume (ml) | 0.3 | 0.039 |
| Total feed gas flow rate (ml/min) | 180 | 2.93 |
| EB concentration (%) | 9.89 | 18.80 |
| Contact time based on reactor volume(s) | 0.10 | 0.80 |
| GHSV based on reactor volume (1/h) | 36000 | 4508 |
| GHSV based on catalyst amount (ml,/g-cat/h) | 27000 | 6104 |
| EB GHSV based on catalyst amount (ml/g-cat/hour) | 2670 | 1148 |
| Styrene yield (%) | 39 | 81 |
| Styrene yield (ml/g-cat/hour) | 1041 | 930 |
| Ratio (microgrooved catalyst/powder catalyst) |  | 0.9 |

Examples 1 and 6 suggest that at a lower temperature (412° C. versus 450-500° C.) higher conversions of ethylbenzene may be achieved. A comparison between Examples 1 and 6 suggests that a higher single pass yield of styrene (81% versus 39%) may be achieved when the catalyst supported microgrooved support strip of Example 6 is used.

EXAMPLE 7

Microgrooved Test Reactors #1 and #2 are fabricated. The reactors contain inlet and outlet tubing, headers and footers, a body cover plate, a body backing plate and a microgrooved assembly. The inlet and outlet tubing is welded to the header and footer of each device. Each is a 3 inch (7.62 cm) length of ⅛ inch (0.318 cm) OD SS316 tube with a tubular wall thickness of 0.035 inch (0.089 cm). The headers and footers are fabricated from SS316 bar stock via conventional machining and have outer dimensions of 0.820 inch×0.375 inch×0.375 inch (2.08×0.953×0.953 cm). One of the 0.375 inch×0.820 inch (0.953×2.08 cm) faces is given a 45° 0.020 inch (0.0508 cm) chamfer on each of the 0.375 inch (0.953 cm) long edges. This face is the "top" of the piece. A 0.180 inch (0.457 cm) deep by 0.520 inch (1.32 cm) long by 0.069 inch (0.175 cm) wide slot is cut in one of the 0.820 inch×0.375 inch (2.08×

0.953 cm) faces (orthogonal to the top face) such that the long axis of the slot is located 0.227 inch (0.577 cm) from the bottom face of the piece and the short axis of the slot is located 0.410 inch (1.04 cm) from the 0.375 inch (0.953 cm) long edge of the face. The slot is flat bottomed and terminated in a full round. On the face opposite the slot is drilled a 0.069 inch (0.175 cm) through hole with a 0.125 inch (0.318) counter bore to a depth of 0.125 inch (0.318 cm). The through hole is centered on the location of the slot.

The process microchannel is in the form depicted in FIG. 38 and is assembled using a body cover plate (right side of FIG. 38), a body backing plate and a microgrooved assembly. The microgrooved assembly contains two microgrooved support strips depicted in FIGS. 35-38. The microgrooved support strips are stacked one on top of the other. The microgrooved assembly is attached to the body backing plate. The body cover plate and body backing plate are fabricated from FeCrAlY plate. The body backing plate has overall dimensions of 3.900 inches (9.91 cm) by 0.750 inch (1.91 cm) and is 0.190 inch (0.483 cm) thick. In cross section the part has a raised central tenon 0.502 inch (1.275 cm) wide that runs the length of the device.

Figure 56:
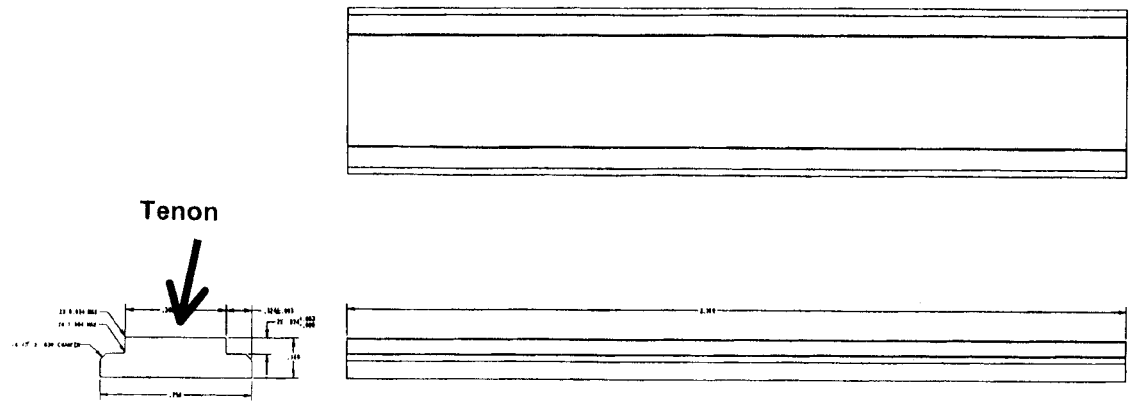
FIG. 56 consists of drawings of the body backing plate used in the microchannel reactor disclosed in Example 7.
Figure 57:
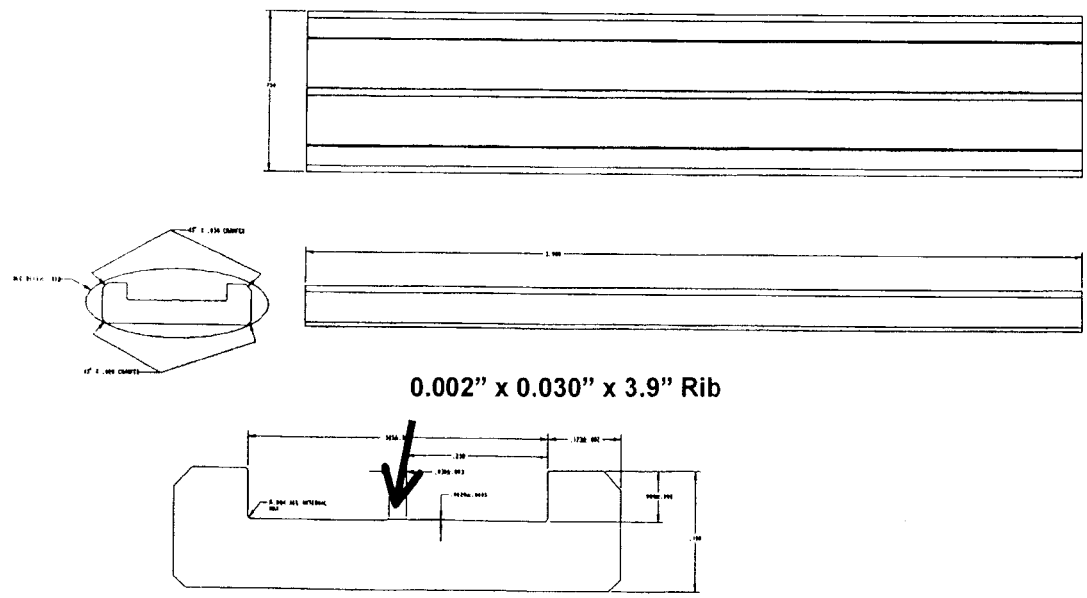
FIG. 57 consists of drawings of the body cover plate used in the microchannel reactor disclosed in Example 7.

The tenon is formed by removing material 0.124 inch (0.315 cm) from either side of the tenon to a depth of 0.074 inch (0.188 cm). The lip of the step so formed is given a 0.030 inch (0.076 cm) 45° chamfer on either side as shown in the lower left of FIG. 56. The body cover plate has overall dimensions of 3.900 inches (9.91 cm) by 0.750 inch (1.91 cm) and is 0.190 inch (0.483 cm) thick. A deep slot is cut down the center of the part 0.505 inch (1.283 cm) wide and 0.080 inch (0.203 cm) deep extending the entire length of the part as shown in FIG. 57. A 0.030 inch (0.076 cm) wide 0.002 inch (50.8 microns) rib of material is left running down the center of the deep slot as shown in FIG. 38. The outside edges of the part adjacent to the slot is given a 0.030 inch (0.076 cm) 45° chamfer. The chamfers on the body cover plate and body backing plate mate after assembling to provide a groove suitable for seal welding. The body backing plate and body cover plate are toleranced and fabricated to provide a friction fit to minimize by pass.

The microgrooved support strips are fabricated via photochemical machining from 0.002 inch (50.8 microns) thick stainless steel 304. Each strip is 2.500 inches (6.35 cm) long and 0.500 inch (1.27 cm) wide. The microgrooves are parallel to each other, 0.007 inch (178 microns) wide and separated from adjacent grooves by 0.007 inch (178 microns) of the base material. The microgrooves form a 20° angle from the center line (long axis of the microgrooved support strip). The microgrooves start approximately 0.030 inch (0.076 cm) from the edge of the strip measuring 0.500 inch (1.27 cm) and each individual microgroove stops approximately 0.007 inch (178 microns) from the long (2.5 inches, 6.35 cm) edge of the strip (see FIGS. 35 and 36). A large central rib (0.064 inch, 1.63 cm wide) is located half way down the length of the microgrooved support strip. The microgrooved assembly is made by stacking two microgrooved support strips, one on top of the other. The angled direction of the microgrooves is alternated to produce a lattice like structure as shown in FIGS. 30 and 31. The microgrooved assembly is then saturated with isopropyl alcohol (to aid in positioning and to maintain flatness) and tack welded to the body backing plate tack welds being placed at the front and back edges and on the middle of the large central rib to produce an assembly as depicted on the left hand side in FIG. 38. The microgrooved assembly is centered on the body backing plate in both the axial and side to side dimensions. Any overhang of the microgrooved support strips is removed with a fine diamond hone. Once completely assembled, the device is in the form of a microchannel with an inlet and outlet gap of 0.006 inch (152 microns) that is approximately 0.503 inch (1.28 cm) wide and 3.900 inches (9.91 cm) long. In the portion of the channel containing the microgrooved support strips the gap is reduced to 0.002 inch (50.8 microns) the balance of the channel being occupied by the microgrooved support strips. The main flow path is through the 0.002 inch (50.8 microns) channel that sits above the 0.004 inch (102 microns) assembly of two microgrooved support strips.

The microgrooved assembly and the body cover plates are cleaned first in an ultrasonic bath containing isopropanol, then a 20% nitric acid solution, and then deionized water. Each cleaning step has a duration of 30 minutes at 90% power output. The bath temperature is 25° C. The cleaned parts are then heated in stagnant air while increasing the temperature at a rate of 3.5° C. per minute to 650° C. and held at that temperature for 10 hours.

The catalyst described in Example 6 is prepared and washcoated on the microgrooved assembly using the procedure described in Example 6. The resulting microchannel reactor is designated as Microgroove Test Reactor #2.

Figure 58:
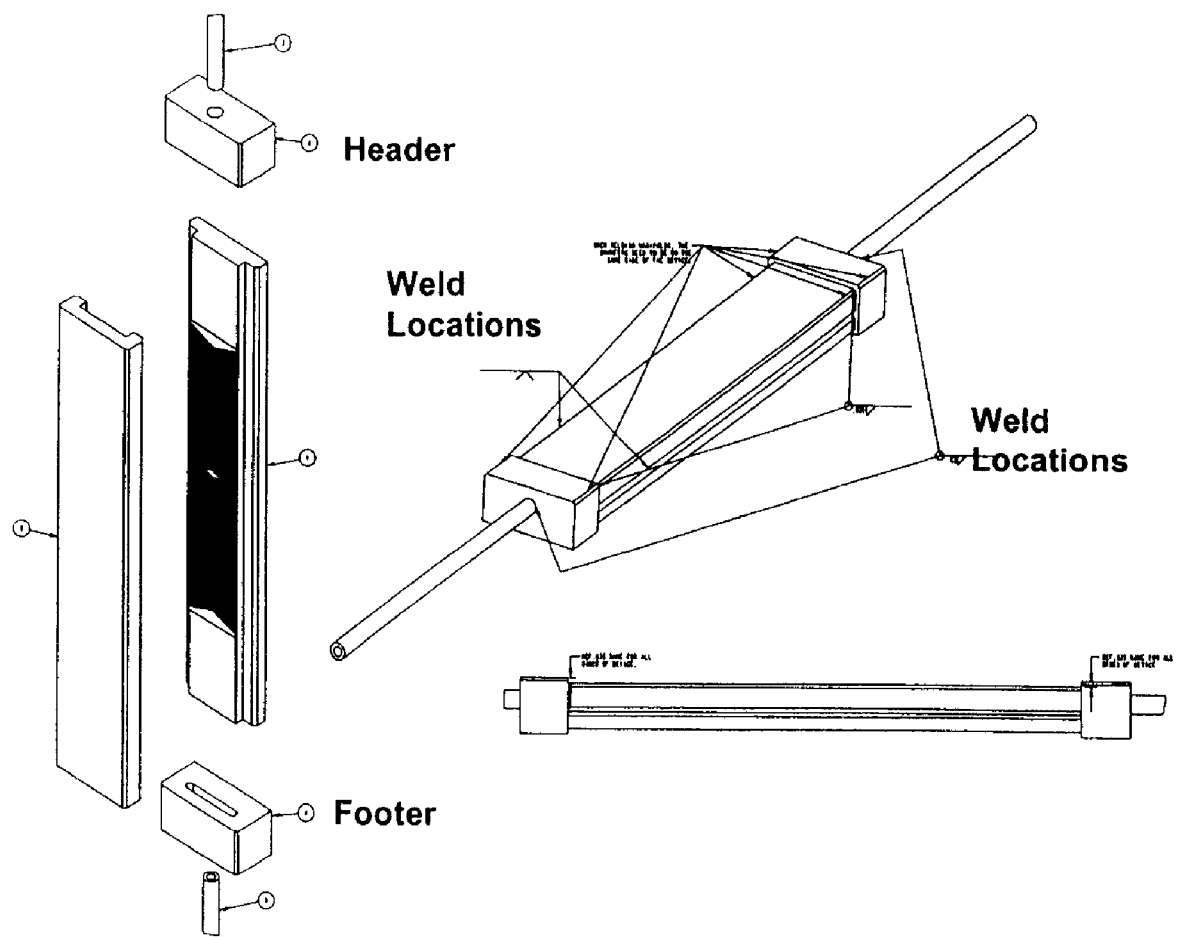
FIG. 58 is a schematic illustration of the microchannel reactor disclosed in Example 7.

The body cover plate is placed on the body backing plate and a seam weld is applied to close the device forming the microchannel reactor body assembly. The header and footer, after having their respective inlet and outlet tubing welded to them are also welded to the body assembly such that the slot on the header or footer is aligned with the channel formed by the body assembly which is shown in FIG. 58. A test set-up for the microchannel reactor is shown in FIG. 54.

Figure 54:
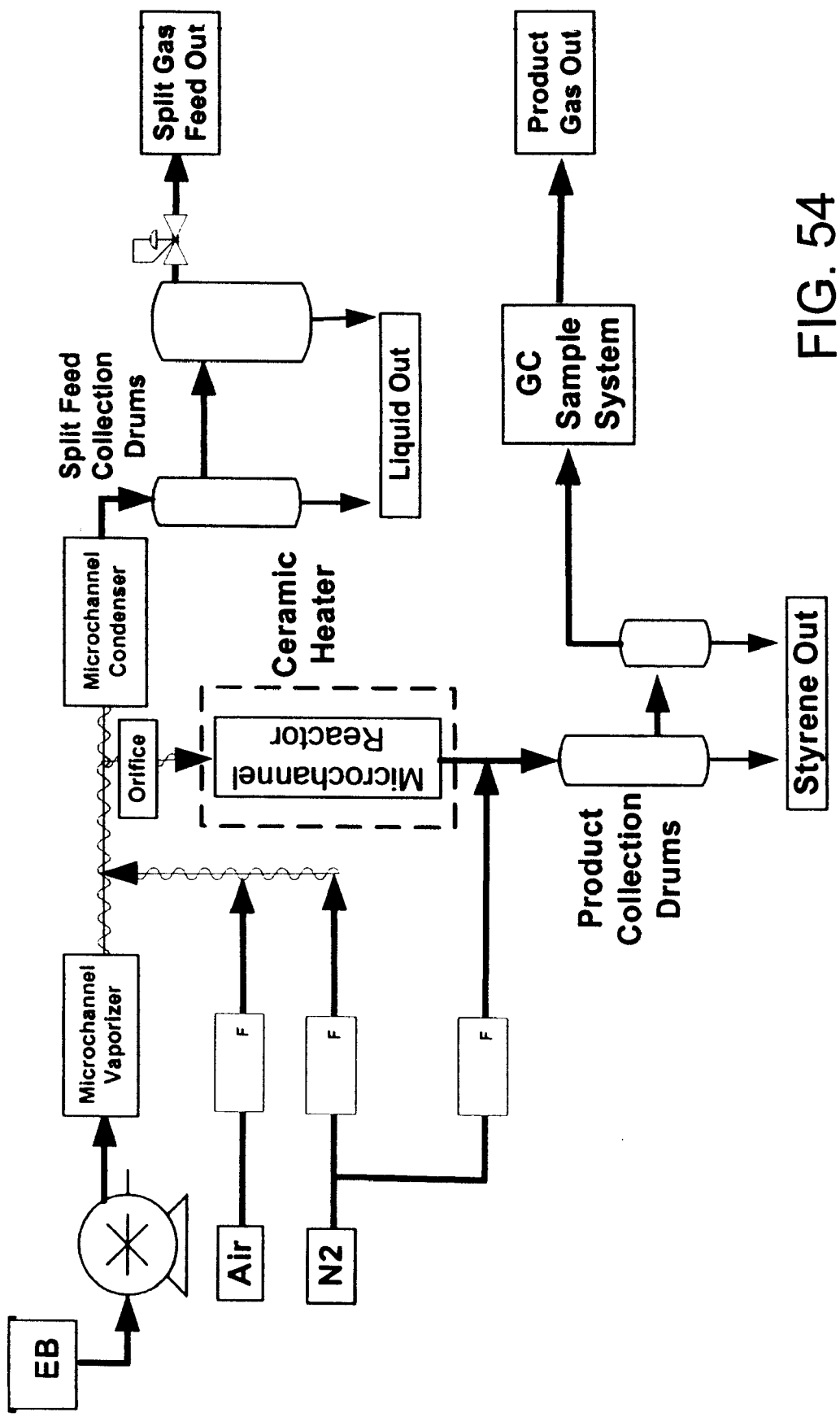
FIG. 54 is a schematic illustration of a test set up for the test runs reported in Examples 7 and 8.

Referring to FIG. 54, ethylbenzene (EB) is pumped into a microchannel vaporizer at a rate of 0.10 ml/min via a HPLC piston pump outfitted with pulse dampeners. The ethylbenzene is heated, vaporized, and superheated to 200° C. before mixing with an air stream. The air is fed into the system with a mass flow controller. The air is preheated before mixing with the ethylbenzene stream by an electrical heating tape that is wrapped around the outside of the feed tube. The surface of the tube is held at held at 200° C. The total feed rate of the air stream ranges from 42-87 SCCM giving an ethylbenzene: oxygen mole ratio ranging from 2.1 to 1.0.

The mixed feed stream of ethylbenzene and oxygen flows through a 200 mesh screen before reaching the orifice and split section. All of the lines and the orifice are heated with and electrical heating tape holding the outside surface of the tubing at 200° C. An orifice with a diameter of 0.0007 inch (17.8 microns) is placed immediately upstream of the reactor. The orifice has a pressure drop that is significantly larger than the pressure drop across the reactor. The feed rate to the reactor is controlled by varying the back pressure of the split stream. The pressures upstream and downstream of the orifice are controlled in order to maintain the total flow to the reactor from 2 to 6 SCCM. The split stream is condensed via a microchannel heat exchanger and collected in two chilled product collection drums. The gasses exit through the back pressure regulator, septa sampling point, and bubble flow meter, before going to a vent. Samples of this exit gas stream are collected by a gas tight syringe and the liquid is collected and analyzed.

The microchannel reactor is installed inside an electrically powered ceramic heating element. This heater provides a temperature ranging from 350° C. to 500° C.

The product of the reactor is mixed with room temperature nitrogen flow of 15 SCCM from a second mass flow controller to help increase the total flow rate through the downstream components. The diluted product is condensed in a chilled, 2 mm glass bead packed sample collection drum. The product is collected in a chilled, open volume knock-out drum before the gas stream is sent through a bubble flow meter and to the on-line GC system. The flow rates of both the split and product gas streams are recorded.

There are two GCs that provide the analysis for the system. The product gas stream is analyzed by an Agilent 5890 GC equipped with two TCD detectors, three sample valves, and a sample pump. $H_2$, $O_2$, $N_2$, $CH_4$, CO, $CO_2$, ethane and ethylene are quantified in the 5890GC with an analysis time of approximately 20 min. The liquid feed, liquid collected from the split stream knockout drum, split stream gas, liquid product and product stream gas are analyzed by an Agilent 6890GC with a FID detector. Benzene, toluene, ethylbenzene and styrene are quantified in approximately 20 min.

The system is started-up as follows. $N_2$ flow at 200 SCCM purges the system as the devices begin to heat. The back pressure is increased on the split stream in order to push flow through the reactor. The reactor flow is established at 5 SCCM. The vaporizer is heated to 200° C. while the heat tracing is heated to 200° C. The reactor is heated to an average temperature of 380° C. at a rate of 3° C./min in the ceramic heater (clam shell furnace). Once the temperatures are steady ethylbenzene and air flows are stepped in, while the $N_2$ flow is stepped out until an ethylbenzene:oxygen mole ratio of 2:1 and reactor inlet flow 4 SCCM is reached. The system is left until steady state and a full sample is recorded. The temperature is then increased at a rate of 2° C./min in 10° C. increments while taking product GC samples. The temperature ramp stops once full oxygen conversion has been reached. The temperature is held constant and a sample is taken at 412° C. average temperature. Next the ethylbenzene:oxygen mole ratio is decreased to 1.8:1, 1.5:1, and 1.1:1 consecutively. This increases conversion of the ethylbenzene and selectivity to styrene.

Conversion of the ethylbenzene and selectivity to styrene is determined using a methodology based on oxygen balance. This method involves determining the conversion of ethylbenzene based on performing an oxygen balance and assumes the following stoichiometry to dominate.

$$C_8H_{10} + 0.5O_2 \rightarrow C_8H_8 + H_2O \quad \text{Equation 1}$$

$$C_8H_{10} + 6.5O_2 \rightarrow 8CO + 5H_2O \quad \text{Equation 2}$$

$$C_8H_{10} + 10.5O_2 \rightarrow 8CO_2 + 5H_2O \quad \text{Equation 3}$$

The conversion of ethylbenzene is approximated as shown in the equations below:

$$x_{EB} = 1 - \frac{n_{ST,out} + \frac{1}{8}(n_{CO,out} + n_{CO_2,out})}{n_{EB,in}} \quad \text{Equation 4}$$

where $n_{CO,out}$, $n_{CO2,out}$, and $n_{ST,out}$ are calculated as follows:

$$n_{CO,out} = n_{dry\,gas,out} \cdot f_{CO,out,dry} \quad \text{Equation 5}$$

$$n_{CO_2,out} = n_{dry\,gas,out} \cdot f_{CO_2,out,dry} \quad \text{Equation 6}$$

$$n_{ST,out} = n_{O,in} - n_{O,out} - \frac{5}{8} \cdot (n_{CO,out} + n_{CO_2,out}) \quad \text{Equation 7}$$

In the above equations, $n_{dry\,gas,out}$ is the measured molar outlet dry flow rate, $f_{i,out,dry}$ is the mole fraction of component i (CO, $CO_2$, or $O_2$) in the dry outlet flow as measured by gas chromatograph, 5/8 is the assumed stoichiometric ratio of $H_2O$ to CO or $CO_2$ formed during combustion, and $$n_{O,in} = 2 \cdot n_{O_2,in} + 2 \cdot 0.21 \cdot n_{air,in} \quad \text{Equation 8}$$

$$n_{O,out} = n_{dry\,gas,out} \cdot (f_{CO,out,dry} + 2 \cdot f_{CO_2,out,dry} + 2 \cdot f_{O_2,out,dry}) \quad \text{Equation 9}$$

where $n_{i,in}$ is the inlet molar flow rate of component i ($O_2$ or air). The above calculations assume a perfect oxygen balance wherein the molar flow rate of water out of the system is equal to the molar flow rate of missing oxygen atoms. It is further assumed that one mole of water is formed for every mole of styrene produced, and five moles of water are formed for every eight moles of CO or $CO_2$ produced.

The weight selectivity to styrene is calculated as follows:

$$Sel_{ST} = \frac{n_{ST,out} \cdot MW_{ST}}{n_{EB,in} \cdot x_{EB} \cdot MW_{EB}} \quad \text{Equation 10}$$

Furthermore, the carbon selectivity to CO, and $CO_2$ is calculated as shown below.

$$Sel_{CO} = \frac{n_{CO,out}}{(n_{CO,out} + n_{CO_2,out} + 8 \cdot n_{ST,out})} \quad \text{Equation 11}$$

$$Sel_{CO_2} = \frac{n_{CO_2,out}}{(n_{CO,out} + n_{CO_2,out} + 8 \cdot n_{ST,out})} \quad \text{Equation 12}$$

The selectivity to non-COx (taken to approximate the carbon selectivity to styrene) is calculated by subtracting the sum of the selectivity to CO and the selectivity to $CO_2$ from 100%.

The results of testing the device are summarized in Table III where comparison is given between similar catalysts tested in a powdered state using a quartz tube reactor (inner diameter 4 mm). The catalyst is online under reactive conditions for 96.5 hours in the Microgroove Test Reactor #2 (see, Table IV).

TABLE III

Test conditions and reactor performance for Microgroove Test Reactor #2. Contact time is based on reactor volume including volume within microgrooved support strips.
Catalyst 0.7% $K_2O$-15% $MoO_3/SiO_2$—$TiO_2$
Oxygen Source Air

| Device | (Type) | Quartz Tube | | | | | | | | | |
|---|---|---|---|---|---|---|---|---|---|---|---|
| Condition | (#) | 1 | 2 | 3 | 4 | 5 | 6 | 7 | 8 | 9 | 10 |
| | | | | Microgroove Test Reactor #2 | | | | | | | |
| $M_{cat}$ | (mg) | 400 | 400 | 28.8 | 28.8 | 28.8 | 28.8 | 28.8 | 28.8 | 28.8 | 28.8 |
| WHSV | ($hr^{-1}$) | 13 | 13 | 8.8 | 7.8 | 9 | 7.4 | 5.5 | 6.4 | 6.2 | 6.3 |
| CT | (ms) | 100 | 100 | 2228 | 2514 | 1902 | 2071 | 2439 | 2096 | 2163 | 2433 |
| GHSV | ($I_{feed}$/(hr $I_{channel}$)) | 36000 | 36000 | 1616 | 1432 | 1892 | 1738 | 1476 | 1718 | 1664 | 1480 |
| T | (° C.) | 450 | 495 | 401 | 415 | 417 | 416 | 418 | 420 | 410 | 416 |
| $EB:O_2$ | (mol/mol) | 2 | 2 | 1.8 | 1.8 | 1.5 | 1.3 | 1.1 | 1.1 | 1.1 | 1.3 |
| Dilution | ($N_2$:Reactants) | 2 | 2 | 0 | 0 | 0 | 0 | 0 | 0 | 0 | 0 |
| | | | | Conversion | | | | | | | |
| EB | (%) | 37.6 | 43.1 | 42.1 | 40.9 | 59.0 | 74.8 | 86.7 | 77.7 | 74.0 | 76.2 |
| $O_2$ | (%) | 91.3 | 98.8 | 83.6 | 97 | 95.4 | 97.8 | 99.1 | 96.9 | 90.2 | 99.7 |
| | | | | Selectivity | | | | | | | |
| Styrene | (mol %) | 91.8 | 92.5 | 93.3 | 90.6 | 93.7 | 94.4 | 94 | 92.9 | 93.3 | 94.4 |
| CO | (mol %) | 2.7 | 2.5 | 1.7 | 2.3 | 1.4 | 1.5 | 1.5 | 1.9 | 1.5 | 1.2 |
| CO2 | (mol %) | 5.5 | 4.9 | 5.1 | 7.1 | 4.9 | 4.2 | 4.5 | 5.2 | 5.2 | 4.4 |
| | | | | Yield | | | | | | | |
| Styrene Yield mol (%) | | 34.5 | 39.9 | 39.3 | 37.1 | 55.3 | 70.6 | 81.5 | 72.2 | 69.0 | 71.9 |

TABLE IV

Time on stream under reactive conditions for Microgroove Test Reactor #2

| | Condition (#) | | | | |
|---|---|---|---|---|---|
| | 3 MG Test Reactor #2 | 5 MG Test Reactor #2 | 8 MG Test Reactor #2 | 9 MG Test Reactor #2 | 10 MG Test Reactor #2 |
| Time on stream (h:m) | 1:45 | 6:15 | 13:20 | 15:00 | 22:30 |

TABLE V

Temperature profiles for Microgroove Test Reactor #2

| | | Data Point | | | | |
|---|---|---|---|---|---|---|
| Reactor Type | | 1 Quartz Tube | 2 Quart Tube | 4 MG Test Reactor #2 | 6 MG Test Reactor #2 | 7 MG Test Reactor #2 |
| WHSV | ($hr^{-1}$) | 13 | 13 | 7.8 | 7.4 | 5.5 |
| T | (° C.) | 450 | 495 | 415 | 416 | 418 |
| EB:O2 | (mol/mol) | 2 | 2 | 1.8 | 1.3 | 1.1 |
| Time on stream | (h:m) | 1:40 | 3:40 | 3:49 | 26:09 | 47:49 |
| pressure drop | (psid) | 3.95 | 6.71 | 0.03 | 0.1* | 0.06 |
| Top of catalyst bed | (° C.) | 450 | 495 | N/A | N/A | N/A |
| ¾" from top of cat bed | (° C.) | 385 | 399 | N/A | N/A | N/A |
| 0.3 inchs from start of coupon | (° C.) | N/A | N/A | 415 | 416 | 418 |
| 0.8 inches from start of coupon | (° C.) | N/A | N/A | 418 | 418 | 419 |
| 1.3 inches from start of coupon | (° C.) | N/A | N/A | 414 | 415 | 413 |
| 1.8 inches from start of coupon | (° C.) | N/A | N/A | 408 | 408 | 403 |
| 2.3 inches from start of coupon | (° C.) | N/A | N/A | 397 | 398 | 388 |

The yield increases are achieved at lower WHSV in the Microgroove Test Reactor #2 but also at significantly reduced temperatures thus productivity may be increased markedly by increasing temperature. As the selectivity is not dramatically reduced by operation at 495° C. (condition 2 in Table III) it is anticipated that the WHSV may be increased in the microchannel reactor employing the microgrooved catalyst support.

EXAMPLE 8

Microgroove Test Reactor #1 is prepared in a manner similar to that described in Example 7 using the catalyst described in Examples 1, 6 and 7. Testing is conducted in a manner analogous to that described in Example 7 with several exceptions. One of these is that the flow of nitrogen used to aid in the down stream purge is 25 SCCM for conditions 3 through 7 and 0 SCCM for conditions 8 through 13. In addition the microgroove test device described in Example 7 is placed in a clam shell furnace such that the bottom (outlet of the microchannel) of the body assembly even with the bottom of the 3 inches long heating zone of the clam shell furnace thus approximately 0.9 inch (2.29 cm) sticks out above the heated zone. In this example the device is placed in the clam shell furnace such that the top (inlet of the microchannel) is even with the top of the heating zone thus approximately 0.9 inch (2.29 cm) sticks out below the heated zone. This leads to a more pronounced temperature profile (15° C. from inlet to outlet for Example 7 vs. 50° C. for Example 8) as can be seen by comparing Tables VII and V.

TABLE VI

Test conditions and reactor performance for Microgroove Test Reactor #1. Contact time is based on reactor volume including volume within microgrooved support strips.
Catalyst 0.7% $K_2O$-15% $MoO_3/SiO_2$—$TiO_2$
Oxygen Source Air

| Device Condition | (Type) (#) | Quartz Tube 1 | 2 | 3 | 4 | 5 | 6 | 7 | 8 | 9 | 10 | 11 | 12 | 13 |
|---|---|---|---|---|---|---|---|---|---|---|---|---|---|---|
| | | | | Microgroove Test Reactor #1 | | | | | | | | | | |
| $M_{cat}$ | (mg) | 400 | 400 | 24.3 | 24.3 | 24.3 | 24.3 | 24.3 | 24.3 | 24.3 | 24.3 | 24.3 | 24.3 | 24.3 |
| WHSV | (hr$^{-1}$) | 13 | 13 | 16 | 14 | 18 | 13 | 13 | 14 | 11 | 11 | 11 | 10 | 6 |
| CT | (ms) | 100 | 100 | 1620 | 1852 | 1440 | 1994 | 1787 | 1660 | 2112 | 2112 | 2112 | 2324 | 2450 |
| GHSV | ($l_{feed}$/(hr $l_{channel}$)) | 36000 | 36000 | 2222 | 1944 | 2500 | 1805 | 2014 | 2169 | 1704 | 1704 | 1704 | 1549 | 1469 |
| T | (° C.) | 450 | 495 | 395 | 454 | 415 | 423 | 423 | 416 | 415 | 425 | 426 | 426 | 426 |
| EB:$O_2$ | (mol/mol) | 2 | 2 | 2.1 | 2.1 | 2.1 | 2.1 | 1.8 | 1.8 | 1.8 | 1.8 | 1.8 | 1.8 | 1 |
| Dilution | ($N_2$:Reactants) | 2 | 2 | 0 | 0 | 0 | 0 | 0 | 0 | 0 | 0 | 0 | 0 | 0 |
| | | | | Conversion | | | | | | | | | | |
| EB | (%) | 37.6 | 43.1 | 30.9 | 32.1 | 39.1 | 52.7 | 73.2 | 43.1 | 42.9 | 40.4 | 37.0 | 37.6 | 53.7 |
| $O_2$ | (%) | 91.3 | 98.8 | 59.2 | 95.7 | 82.8 | 95.1 | 97.4 | 79.9 | 84.9 | 88.1 | 92.1 | 91.4 | 89 |
| | | | | Selectivity | | | | | | | | | | |
| Styrene | (mol %) | 91.8 | 92.5 | 95.7 | 89.2 | 94.2 | 96.0 | 97.4 | 93.9 | 93.2 | 91.7 | 87.4 | 90.3 | 85.1 |
| CO | (mol %) | 2.7 | 2.5 | 0.0 | 2.8 | 1.0 | 0.6 | 0.4 | 1.8 | 2.1 | 2.5 | 3.4 | 2.7 | 4.1 |
| CO2 | (mol %) | 5.5 | 4.9 | 4.3 | 7.9 | 4.7 | 3.4 | 2.1 | 4.3 | 4.8 | 5.7 | 9.2 | 7.0 | 10.9 |
| | | | | Yield | | | | | | | | | | |
| Styrene Yield mol (%) | | 34.5 | 39.9 | 29.6 | 28.6 | 36.8 | 50.6 | 71.3 | 40.5 | 40.0 | 37.0 | 32.3 | 34.0 | 45.7 |

TABLE VII

Temperature profiles for Microgroove Test Reactor #1

| | | Condition # | | | | |
|---|---|---|---|---|---|---|
| Reactor Type | | 1 Quartz Tube | 2 Quart Tube | 4 MG Test Reactor #1 | 6 MG Test Reactor #1 | 7 MG Test Reactor #1 |
| WHSV | (hr$^{-7}$) | 13 | 13 | 14 | 13 | 13 |
| T | (° C.) | 450 | 495 | 454 | 423 | 423 |
| EB:O2 | (mol/mol) | 2 | 2 | 2.1 | 2.1 | 1.8 |
| Time on stream | (h:m) | 1:40 | 3:40 | 3:30 | 25:10 | 26:30 |
| pressure drop | (psid) | 3.95 | 6.71 | 2.06 | 1.25 | 0.99 |
| Top of catalyst bed | (° C.) | 450 | 495 | N/A | N/A | N/A |
| ¾" from top of cat bed | (° C.) | 385 | 399 | N/A | N/A | N/A |
| 0.3 inchs from start of coupon | (° C.) | N/A | N/A | 454 | 423 | 423 |
| 0.8 inches from start of coupon | (° C.) | N/A | N/A | N/A | N/A | N/A |
| 1.3 inches from start of coupon | (° C.) | N/A | N/A | 437 | 405 | 406 |
| 1.8 inches from start of coupon | (° C.) | N/A | N/A | N/A | N/A | N/A |
| 2.3 inches from start of coupon | (° C.) | N/A | N/A | 404 | 374 | 375 |

TABLE VIII

Time on stream under reactive conditions for Microgroove Test Reactor #1

| | Conditon (#) | | | | | | | |
|---|---|---|---|---|---|---|---|---|
| | 3<br>MG Test<br>Reacor #1 | 5<br>MG Test<br>Reacor #1 | 8<br>MG Test<br>Reacor #1 | 9<br>MG Test<br>Reacor #1 | 10<br>MG Test<br>Reacor #1 | 11<br>MG Test<br>Reacor #1 | 12<br>MG Test<br>Reacor #1 | 13<br>MG Test<br>Reacor #1 |
| Time on stream (h:m) | 1:30 | 6:20 | 18:20 | 20:35 | 22:15 | 41:20 | 65:35 | 73:00 |

In Example 8 the advantages of the microgrooved support structure are apparent when the same catalyst is run in both a packed bed in a quartz tube (4 mm inner diameter) and the microgrooved reactor. In this case when condition 2 and condition 7 in Table VI are compared the microgrooved reactor allows for improve conversion and selectivity at a similar weight hourly space velocity (WHSV) and lower temperature. The term WHSV is used herein to refer to the mass of reactant (for example, ethylbenzene) per unit of time contacting a given mass of catalyst. The enhanced productivity of Microgroove Test Reactor #1 vs. Microgroove Test Reactor #2, where Microgroove Test Reactor #1 has a higher conversion at greater WHSV, may be due to the larger pressure drop experienced by Microgroove Test Reactor #1, a on possible outcome of which may be that part of the bulk flow is diverted from the flow by channel into the microgrooved structure.

Figure 55:
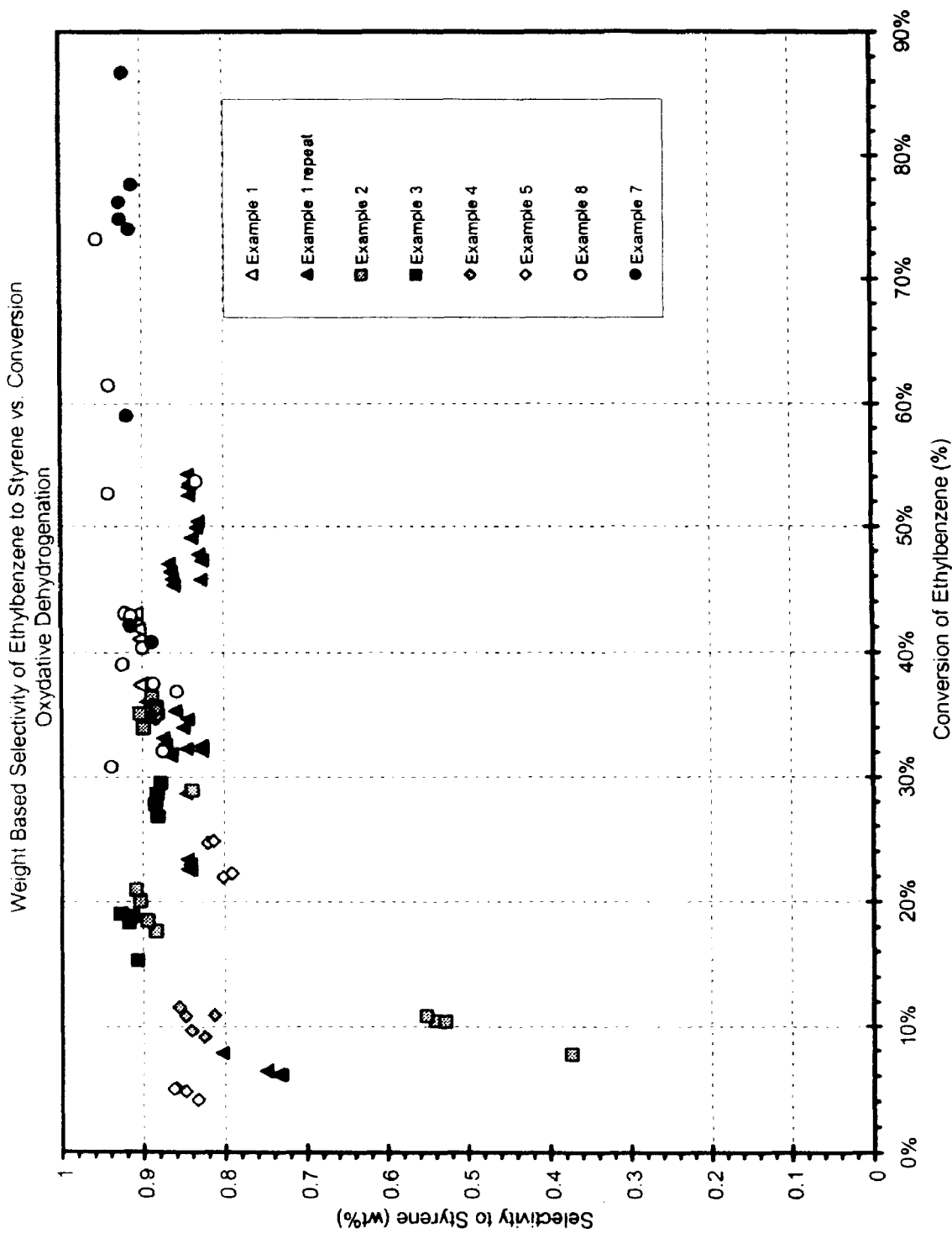
FIG. 55 is a chart showing conversion of ethylbenzene and selectivity to styrene for tests reported in Examples 1-5, 7 and 8.

The results for two microgrooved test reactors (Examples 7 and 8) are compared to results collected for the catalysts reported in Examples 1 through 5. The comparison is shown in FIG. 55. These results show that beyond approximately 40% conversion in the quartz tube reactor selectivity falls off step wise while the enhanced ability of the microgrooved reactor to remove heat allows for conversion to be increased beyond 40% while at the same time maintaining high selectivity.

EXAMPLE 9

A computational fluid dynamics (CFD) study on thermal management for the formation of styrene via oxidative dehydrogenation of ethylbenzene is conducted. The production of styrene in a microchannel reactor may be particularly advantaged by the incorporation of a structured wall to increase the surface area for coating a highly active and selective ethylbenzene oxidative dehydrogenation (ODH) catalyst. The reactor may be further advantaged by incorporating a thermal resistance layer in the heat transfer wall between the heat exchange transfer channel and the process microchannel to create a controlled temperature gradient such that a lower temperature heat exchange fluid, such as an oil, may be used to remove heat for higher temperature oxidation reactions. Typical hot oils may be rated to a maximum of about 400° C. A desirable operating temperature window for styrene production via oxidative dehydrogenation of ethylbenzene may be in the range from about 300° to about 500° C., and in one embodiment from about 400° to about 450°. In one embodiment, the oxidant may be added by staged into the process microchannel to reduce the local partial pressure of oxygen and enhance the resulting reaction selectivity to styrene.

A microchannel reactor may be designed to maintain a heat exchange fluid temperature at 380° while running the process microchannel at 420° C. by positioning a thermal resistance layer between the process microchannel and heat exchange channel. The thermal resistance layer may not be open to flow of heat exchange fluid or process reactants. The thermal resistance layer may be formed using techniques and constructions similar to those used for making structured walls. The pattern selected for the thermal resistance layer may be the same as or different than the structured wall in the process microchannel for supporting the catalyst.

The temperature rise in the catalyst may be controlled by varying the thermal resistance in thermal resistance layer. The thermal resistance may be varied along the length of the process microchannel. It may be desirable to have a higher thermal lag at one end of the process microchannel or a varying function down the process microchannel length either digitally or in an analog fashion.

The structured walls that support the catalyst may vary along the length of the process microchannel to reduce or enhance the heat release such that isothermal or an axially varying temperature profile may be obtained.

Transient simulation shows that the thermal resistance layer may not create an unpredictable thermal response or thermal lag to the change of flow variables. Temperature overshoot may not occur at high temperature locations. This may be an important consideration to keep the catalyst temperature under control to avoid hot spots, sintering, deactivation, or otherwise unwanted thermal excursions.

Microchannel apparatus 600 illustrated in FIG. 61 is used to convert ethylbenzene (EB) to styrene in the presence of an oxidative dehydrogenation (ODH) catalyst. The apparatus includes process microchannel 602 and heat exchange channel 604. Heat transfer wall 605 is positioned between the process microchannel 602 and heat exchange channel 604. The process microchannel 602 includes bulk flow region 603 and structured wall 606 which is used to support the ODH catalyst. Thermal resistance layer 608 is positioned between the process microchannel 602 and heat exchange channel 604. In FIG. 61 only half the process microchannel 602 is shown. The other half of the process microchannel has a second structured wall for supporting the ODH catalyst opposite the structured wall 606, and a second thermal resistance layer 608. The structured wall 606 and the thermal resistance layer 608 are constructed by stacking a plurality of the microgrooved shims illustrated in FIGS. 59 and 60 one above another. Each of the microgrooved shims has a thickness of 50 microns.

The shims have alternating patterns such that a porous structure having a thickness of 1.5 mm is created when 30 shims are stacked together to form the structured wall 606. The openings in the alternating shims are arranged to create solid metal connections through the stack of 30 shims along with completely open large pores through the stack to facilitate rapid diffusion. There are cross members that extend from the solid metal connections through some of the open porous area to further increase the internal surface area. The mass of reactants diffuse and to some extent slightly flow within the open porous structure. The openings of the structured wall vary from about 25 microns to about 500 microns. The ODH catalyst may coat the entire surface area of the structured wall 606.

The bulk flow region 603 in the process microchannel 602 has a height of 0.75 mm. The bulk flow region 603 reduces the impediment to flow resistance and allows the reactants to diffuse into the open structured walls 606 to access the catalyst. The length of the process microchannel 602 is 56 inches (142.2 cm). The channel width is 0.25 inches (0.64 cm).

The thermal resistance layer 608 has the same construction as the structured wall 606 (except that no catalyst is present). The thermal resistance layer 608 has a thickness of is 0.5 mm thick and is separated by wall 609 from the structured wall 606 and by wall 610 from the heat exchange channel 604.

The following chemical reactions are conducted:

$$C_6H_5CH_2CH_3 + 0.5O_2 \rightarrow C_6H_5CH=CH_2 + H_2O \quad 1.$$

$$C_6H_5CH=CH_2 + 6O_2 \rightarrow 8CO + 4H_2O \quad 2.$$

$$C_6H_5CH=CH_2 + 10O_2 \rightarrow 8CO_2 + 4H_2O \quad 3.$$

Reaction 1 is the main reaction.
The catalyst kinetics are shown below:

1: $r_{EB} = k_{o1} \exp\left[\frac{-E_{a1}}{RT}\right] C_{EB} C_{O_2}^{0.5}$

2: $r_{ST} = k_{o2} \exp\left[\frac{-E_{a2}}{RT}\right] C_{ST} C_{O_2}$

3: $r_{st} = k_{o3} \exp\left[\frac{-E_{a3}}{RT}\right] C_{ST} C_{O_2}$

The parameters are given in the following Table.

| Reaction | Parameter | Value | Units |
|---|---|---|---|
| 1 | $k_{o1}$ | 8.66E−02 | ($m^{9/2}$ a−1 $Kmol^{−1/2}mg^{−1}$) |
|  | $E_{a1}$ | 71063 | (J/mol) |
| 2 | $k_{o2}$ | 2.38E+05 | ($m^6 kgmol^{−1}s^{−1}mg^{−1}$) |
|  | $E_{a2}$ | 165542 | (J/mol) |
| 3 | $k_{o3}$ | 2.48E+03 | ($m^6 kgmol^{−1}s^{−1}mg^{−1}$) |
|  | $E_{a3}$ | 130195 | (J/mol) |

The reaction rates are in kmol/mg-cat. The catalyst loading in the structured wall 606 is 1.365E+05 g-cat/$m^3$ as experimentally demonstrated.

Simulations to evaluate the impact of the thermal resistance layer 608 are based on the following assumptions:

The reaction contact time is based on the volume defined by the total internal reactor volume inclusive of the structured walls 606 and bulk flow region 603 for process flow.

Wall temperature 380° C.—as maintained by the boiling of a hot oil such as Therminol or Dowtherm, or the convective heat transfer of a fluid Reaction nominal temperature of 420° C.
Ethylbenzene (EB) to $O_2$ ratio=1.8 ($O_2$ fed as air)
Outlet pressure set to 1 atm
The concentration of the feed is given in the table below:

|  | mole fraction | mass fraction |
|---|---|---|
| EB | 0.2743 | 0.5819 |
| $O_2$ | 0.1524 | 0.0974 |
| $N_2$ | 0.5733 | 0.3207 |

Figure 62:
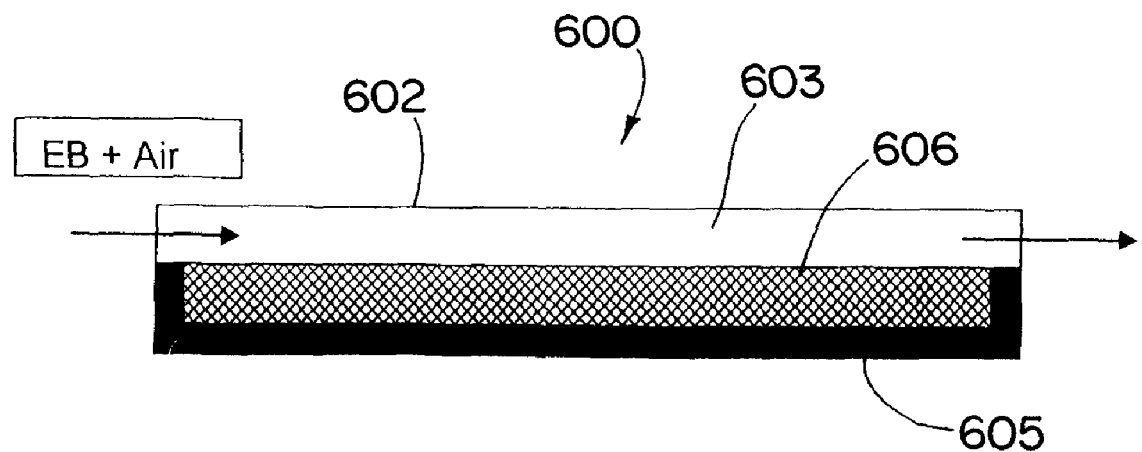
FIG. 62 is a schematic illustration of the process microchannel illustrated in FIG. 61.

The heat removal rate is first estimated using a two-dimensional model of the process microchannel only. The structured wall catalyst has an effective thermal conductivity of 4 W/m-K. The wall temperature is maintained at a constant 420° C. and the feed inlet is also 420° C. The channel geometry is shown in FIG. 62. The table below shows the reactor performance when the catalyst activity is at the reported level (1×). The impact of increasing and decreasing the catalyst activity is also shown in the table below.

| Reactor Performance Summary Contact time: 200 ms |  |  |  |  |
|---|---|---|---|---|
|  |  | 0.5X Kinetics | 1X Kinetics | 2X Kinetics |
| Conversion | EB | 33.7% | 47.4% | 51.2% |
| Conversion | $O_2$ | 30.9% | 93.5% | 92.9% |
| Selectivity | Styrene | 99.2% | 94.5% | 91.7% |
| Selectivity | CO | 0.1% | 5.4% | 4.8% |
| Selectivity | $CO_2$ | 0.7% | 3.9% | 3.6% |
| T, max | C | 437 | 444 | 761 |

Figure 63:
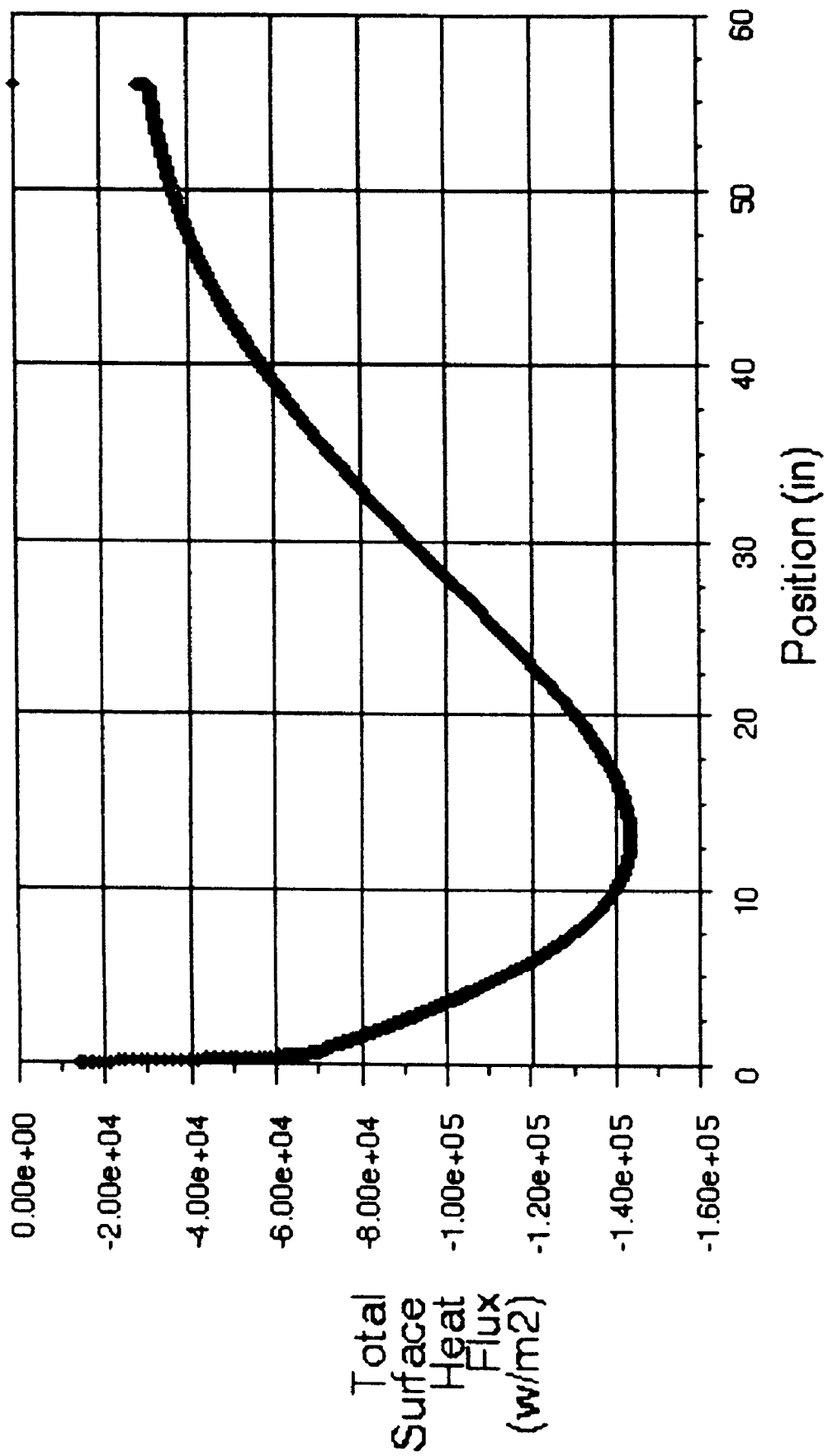
FIG. 63 is a plot of heat flux for the flow of heat through the heat transfer wall for the process reported in Example 9.

The heat flux profile for the flow of heat through the heat transfer wall wherein the catalyst structure is for a catalyst with 1× kinetics and a contact time of 200 ms is shown in FIG. 63. The negative sign means the heat is removed from the domain through the wall. The heat flux reaches peak value at about 13 inches (33.0 cm) into the reactor length (of the total 56 inch (142.2 cm) reactor length) and the peak value is about 14 W/$cm^2$.

Figure 64:
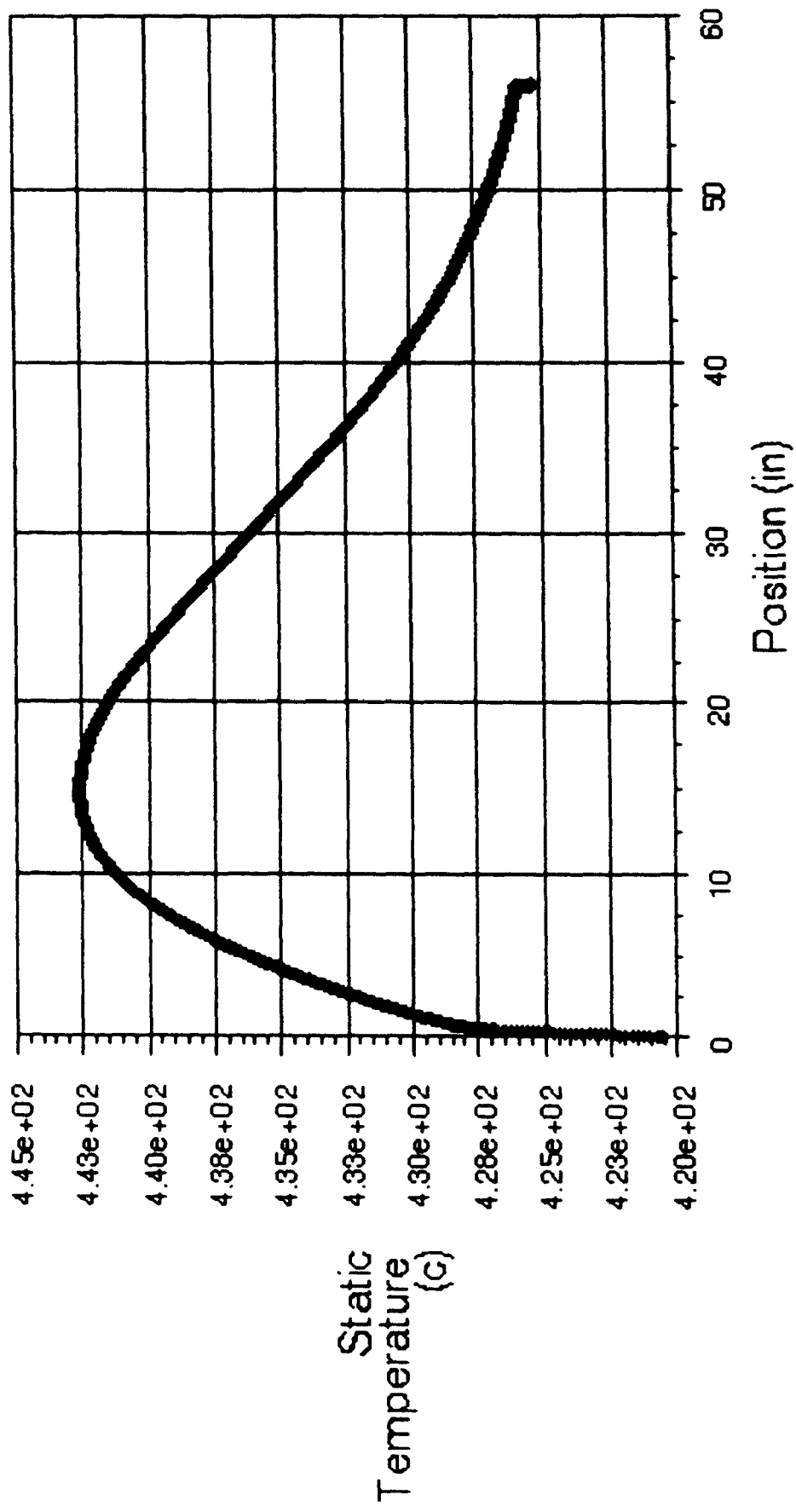
FIG. 64 is a plot of temperature profile for the process reported in Example 9.

FIG. 64 shows the temperature profile in the catalyst structure at a location of 0.01 inch (0.254 mm) deep in the structure at 1× kinetics and a contact time of 200 ms. The temperature reaches a peak value 15 inches (38.1 cm) from the front edge of the catalyst structure, roughly the same axial location of maximum heat flux. The maximum temperature for this case is 444° C., which is 24° C. above the targeted operating temperature.

Figure 65:
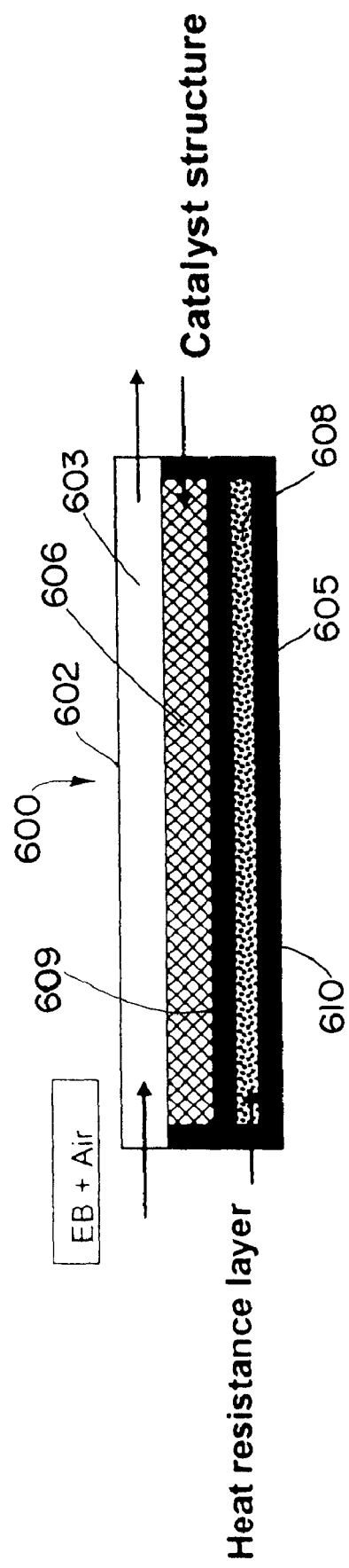
FIG. 65 is a schematic illustration of the process microchannel and heat transfer wall shown in FIG. 61.
Figure 66:
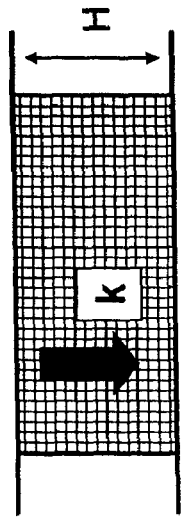
FIG. 66 is a schematic illustration of a thermal resistance layer and a formula for calculating heat flux.

In the next step of the design, the thermal resistance or heat resistance layer 608 is added between the process microchannel 602 and the heat exchange channel 604. This is shown in FIGS. 65 and 66. The thermal resistance layer is modeled as a porous medium with adjustable properties. The coolant wall is maintained at 380° C. with a reaction feed temperature of 420° C. as shown in FIG. 66.

The required features of the heat resistance layer are estimated by one-dimensional heat conduction calculations. It is assumed that the effective thermal conductivity of the heat resistance layer 608 is constant k. The actual value may be calculated if the structure of the layer is known. The thickness of heat resistance layer 608 is assigned as H. The heat flux is determined from the temperature difference using the equation in FIG. 66.

If the required heat flux Q is known, the value of the effective thermal conductivity of the heat resistance layer 608 can be determined given the thickness of the thermal resistance layer 608. The range of the heat flux may be from about 1.0E5 to about 1.0E6 W/$m^2$. The thickness of the heat resistance layer 608 may be in the range from about 0.02 to about 0.08 inches (about 0.508 to about 2.032 mm). The effective thermal conductivities of the thermal resistance layer are reported in the following table. This table shows that if higher level of heat removal is desired, the thermal resistance layer should be either more conductive or fabricated using a material with a higher thermal conductivity. This may be accomplished by creating fewer voids in the strips or shims that may be used to form the thermal resistance layer 608. If the desired heat removal rate is 1.0E5 W/$m^2$, the thermal conductivity may be from 1.27 to 5.08 W/m-K for a thermal resistance layer having a thickness from about 0.02 to about 0.08 inch (about 0.508 to about 2.032 mm). If the openness of the shim is 0.5 (that is 50% metal and 50% void), the effective thermal conductivity of the thermal resistance layer may be about one-fourth of that of the base material, which in this case is steel. The effective thermal conductivity may be about 4 W/m-K.

|  |  | Effective thermal conductivity, W/m-K | | | |
|---|---|---|---|---|---|
| Heat Flux, Q W/m² | k/H W/m²-K | 0.02 inch | 0.04 inch | 0.06 inch | 0.08 inch |
| 1.00E+05 | 2.50E+03 | 1.27 | 2.54 | 3.81 | 5.08 |
| 4.00E+05 | 1.00E+04 | 5.08 | 10.16 | 15.24 | 20.32 |
| 8.00E+05 | 2.00E+04 | 10.16 | 20.32 | 30.48 | 40.64 |
| 1.00E+06 | 2.50E+04 | 12.70 | 25.40 | 38.10 | 50.80 |
| 1.50E+06 | 3.75E+04 | 19.05 | 38.10 | 57.15 | 76.20 |

The table below shows reactor performance at four contact times. The catalyst activity in these models is 50% (or 0.5X) of the reported level. The thermal resistance layer is 0.02 inch (0.508 mm) thick and the thermal conductivity is 2.23 W/m-K.

| Reactor performance 0.5X kinetics over reported Thermal Resistance layer has a k of 2.23 W/m-K and is 0.02 inch thick | | | | | |
|---|---|---|---|---|---|
| Contact time | ms | 1000 | 500 | 2000 | 200 |
| Conversion | EB | 33.7% | 28.8% | 34.7% | 15.3% |
| Conversion | $O_2$ | 30.9% | 30.1% | 31.5% | 22.3% |
| Selectivity | Styrene | 99.2% | 98.8% | 99.2% | 98.1% |
| Selectivity | CO | 0.1% | 0.2% | 0.1% | 0.4% |
| Selectivity | $CO_2$ | 0.7% | 1.0% | 0.7% | 1.5% |
| T, max | °C. | 437 | 434 | 420 | 444 |

Trends identified from these results may include:
There exists a range of flow rates within which the reactor performance is stable.
The maximum temperate increases as the contact time gets shorter.
The location of maximum temperature shifts downstream as the contact time gets shorter.
Ethylene conversion is low at short contact time, but the maximum temperature remains high. This trend shows the importance of further increases to the effective thermal conductivity of the structured wall 606 for supporting the catalyst.

Figure 67:
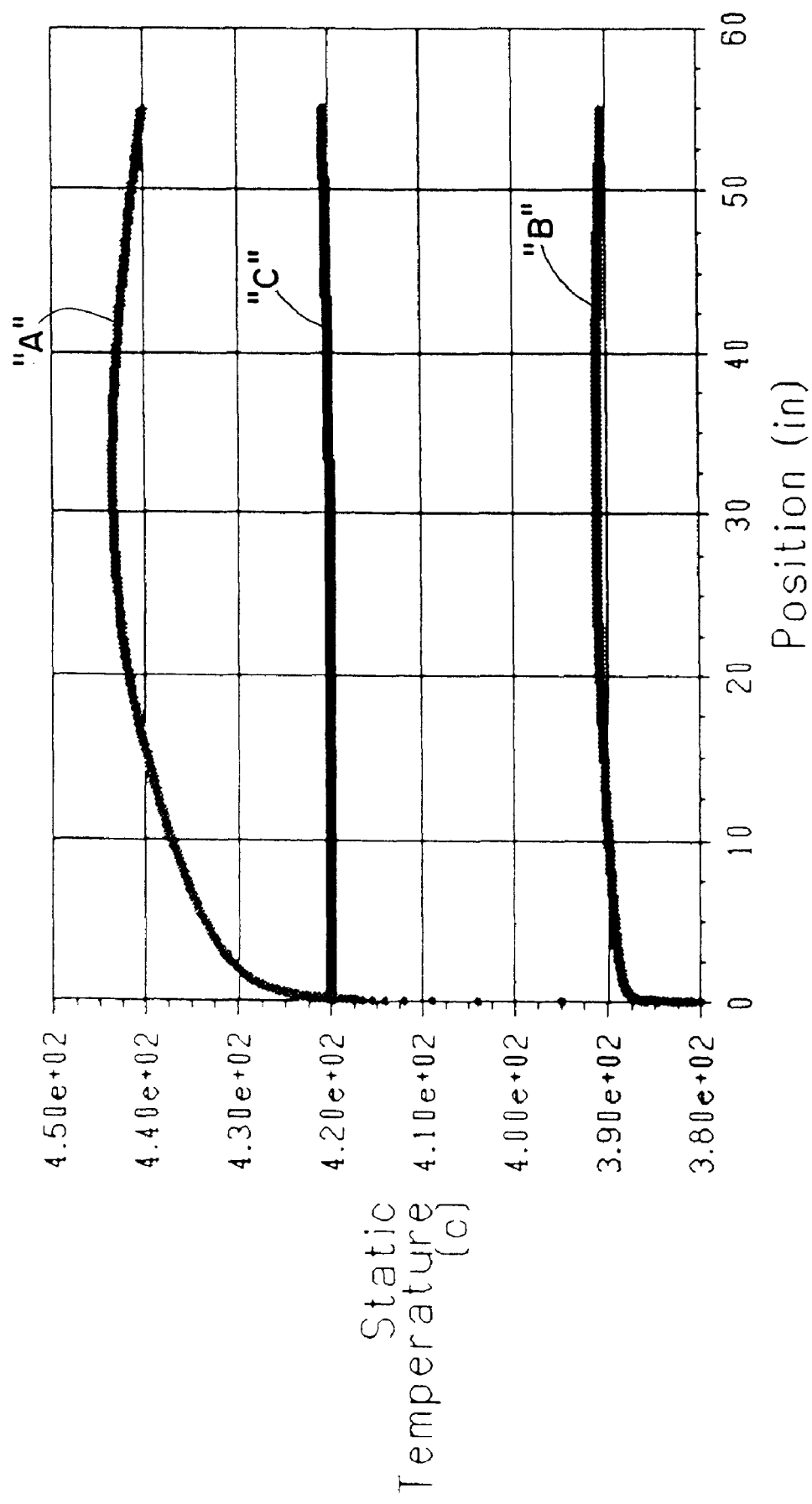
FIG. 67 is a plot showing temperature profiles at three locations within the microchannel reactor discussed in Example 9 wherein the contact time is 200 ms.

FIG. 67 shows the temperature profiles at three locations for a 200 ms contact time. The curve labeled "A" is for the profile in the catalyst structure at a depth 0.01 inch (0.254 mm) from the interface with the bulk flow region 603. The curve labeled "B" is for the profile at the middle of the thermal resistance layer 608, and the line labeled "C" is along the center open flow area of the bulk flow region 603. The fluid temperature is at almost a constant level. The temperature in the resistance layer is relatively flat. The only significant temperature variation along the reactor length is in the structured wall for supporting the catalyst. This temperature is above the target level. The maximum temperature rise is 24° C. This implies that the thermal resistance of the thermal resistance layer should be lowered to bring down the maximum temperature.

Figure 68:
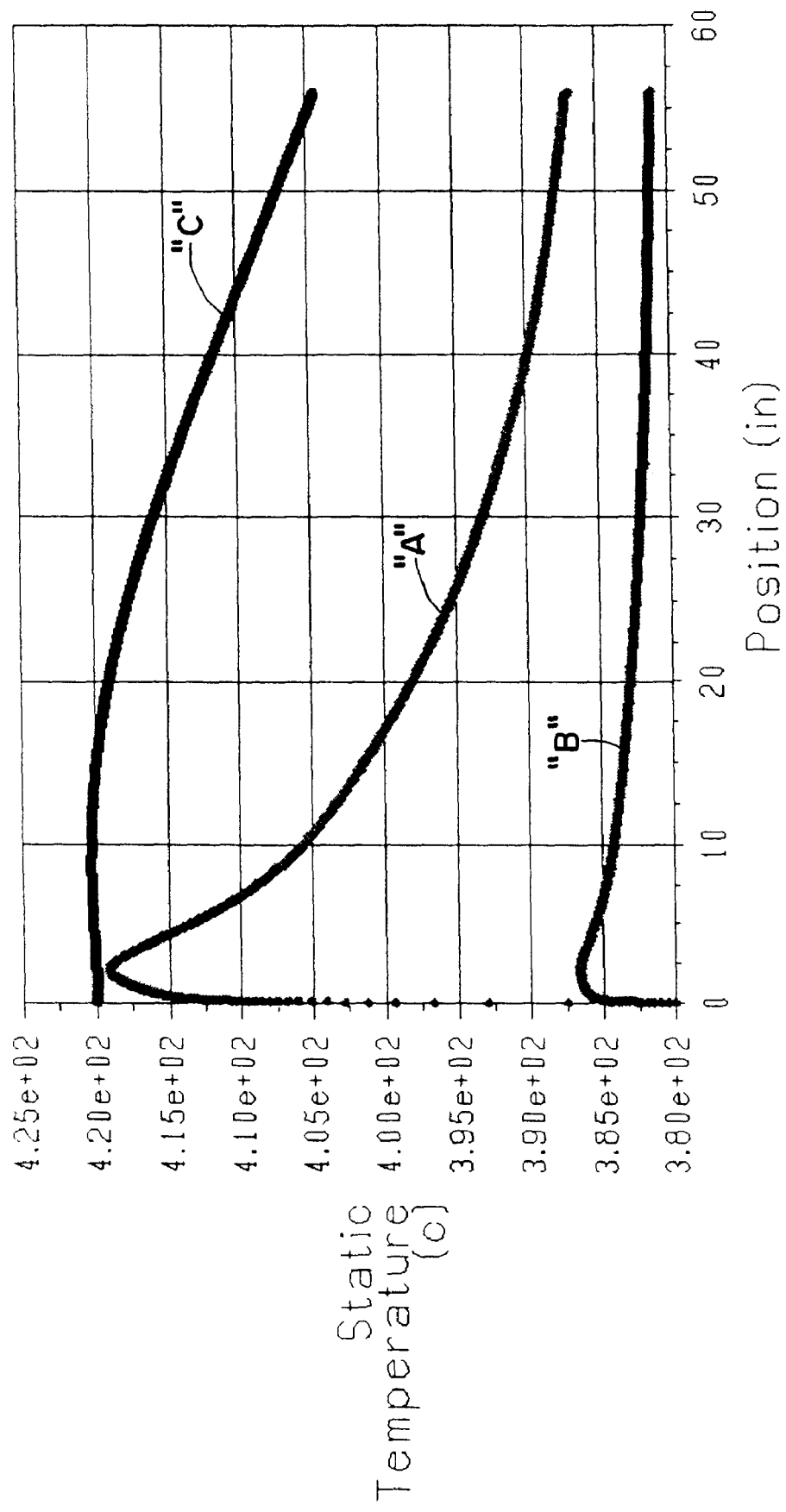
FIG. 68 is a plot showing temperature profiles at three locations within the microchannel reactor discussed in Example 9 wherein the contact time is 2,000 ms.

The temperature predictions for a 2000 ms contact time are plotted in FIG. 68. Temperatures at three locations are shown.

The curve labeled "A" is in the structured wall for supporting the catalyst as indicated above. The curve labeled "B" is in the thermal resistance layer. The curve labeled "C" is in the center of the bulk flow region 603. For this case, although the temperature is controlled below the target temperature near the inlet of the reactor, at other axial locations, the temperature is below the target level. This shows that the heat resistance layer for the reactor is overly conductive or that the thermal resistance is higher than it should be. This low average catalyst temperature contributes to a relatively low ethylbenzene conversion.

Figure 69:
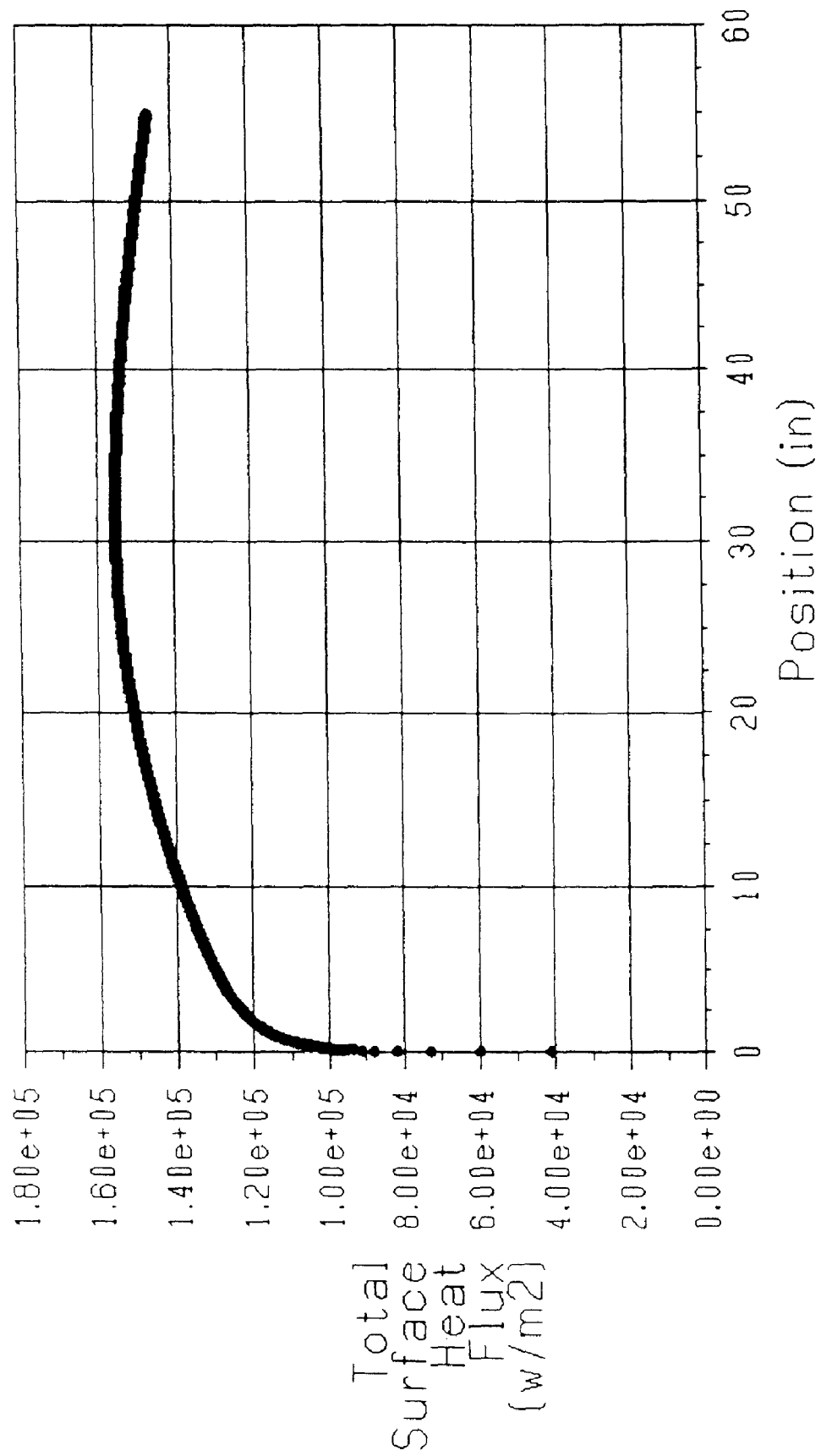
FIG. 69 is a plot showing heat flux through the heat transfer wall of the microchannel reactor discussed in Example 9 wherein the contact time is 2,000 ms.
Figure 70:
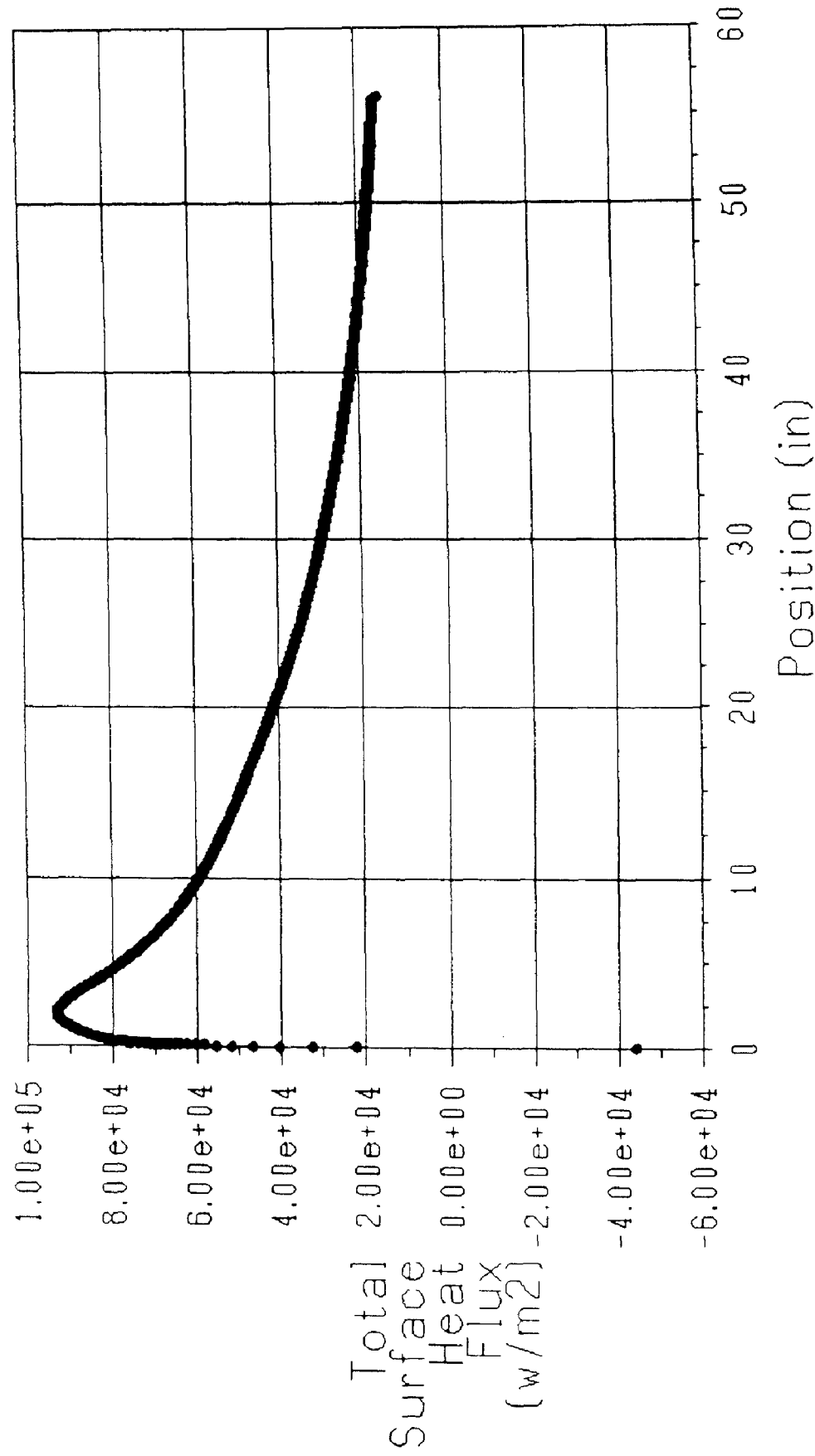
FIG. 70 is a plot showing heat flux through the heat transfer wall of the microchannel reactor discussed in Example 9 wherein the contact time is 200 ms.

The heat flux through the heat transfer wall at a contact time of 2000 ms is shown in FIG. 69. The heat flux through the heat transfer wall at a contact time of 200 ms is shown in FIG. 70.

Even at modest levels of ethylbenzene conversion, the temperature in catalyst structure is significant. The temperature rises with more active catalysts. As such it may be advantageous to tailor the catalyst loading density along the reactor length to reduce the temperature rise. This may be achieved by using different patterns of the structured walls at different axial positions so that the surface area to volume is lower in the front of the reactor and higher near the end of the reactor. Another way to boost the ethylbenzene conversion while controlling temperature rise may be to tailor the thermal resistance of the thermal resistance layer along the reactor length. Based on the temperature profile for the 1000 ms contact time case, the reaction temperature in most of the reactor may be lower than the target level. As such, the thermal resistance in the second half of the reactor may be lowered in order to raise the reaction temperature to a temperature near the desired level.

EXAMPLE 10

This example shows that reactor performance may be improved by varying thermal resistance along the length of the process microchannel. The catalyst structure is divided into several sections along the process microchannel. The thermal resistance layer is also divided into the same number of sections. The details of catalyst activity and thermal resistance in each section are given in the following table.

| Sectional catalyst activity and thermal resistance Baseline thermal conductivity: 2.23 W/m-K (1y) Thermal resistance layer thickness: 0.02 inch (0.508 mm) | | | |
|---|---|---|---|
| Section | Location (inches) | Kinetics scale factor (1x is reported) | Thermal conductivity scale factor |
| 1 | 0-18 | 0.8x | 1y |
| 2 | 18-22 | Linear from 0.8x to 1.2x | 1y |
| 3 | 22-40 | 1.2x | 1y |
| 4 | 40-44 | Linear from 1.2x to 1.5x | Linear from 1y to 0.5y |
| 5 | 44-56 | 1.5x | 0.5y |

| Reactor performance | | |
|---|---|---|
| Contact time | ms | 200 |
| Conversion | EB | 49.0% |
| Conversion | $O_2$ | 64.4% |
| Selectivity | Styrene | 97.2% |

-continued

| | Reactor performance | |
|---|---|---|
| Selectivity | CO | 1.0% |
| Selectivity | CO$_2$ | 1.7% |
| T, max | ° C. | 451 |

Figure 71:
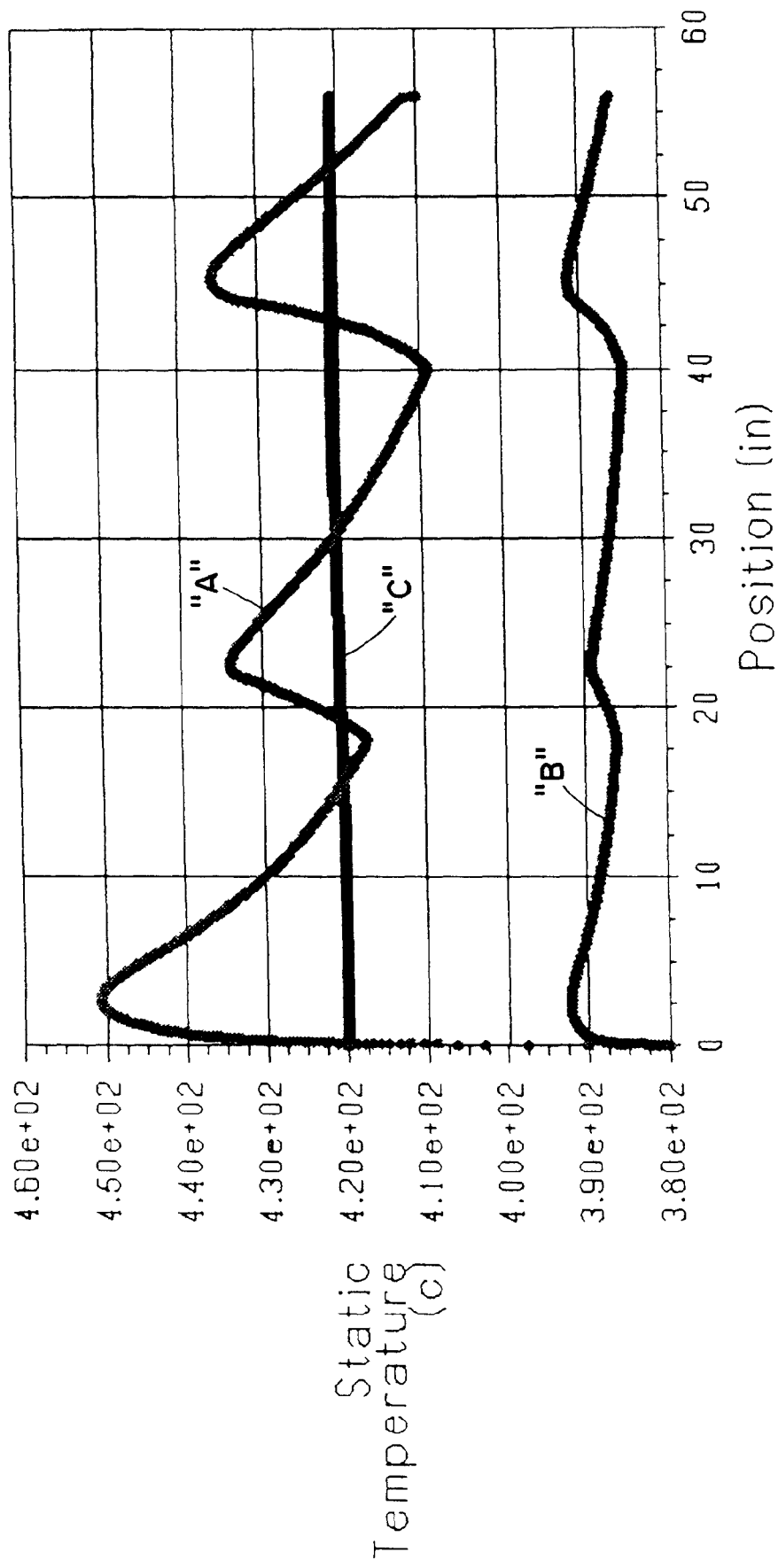
FIG. 71 is a plot showing three temperature profiles within a microchannel reactor for the process reported in Example 10.
Figure 72:
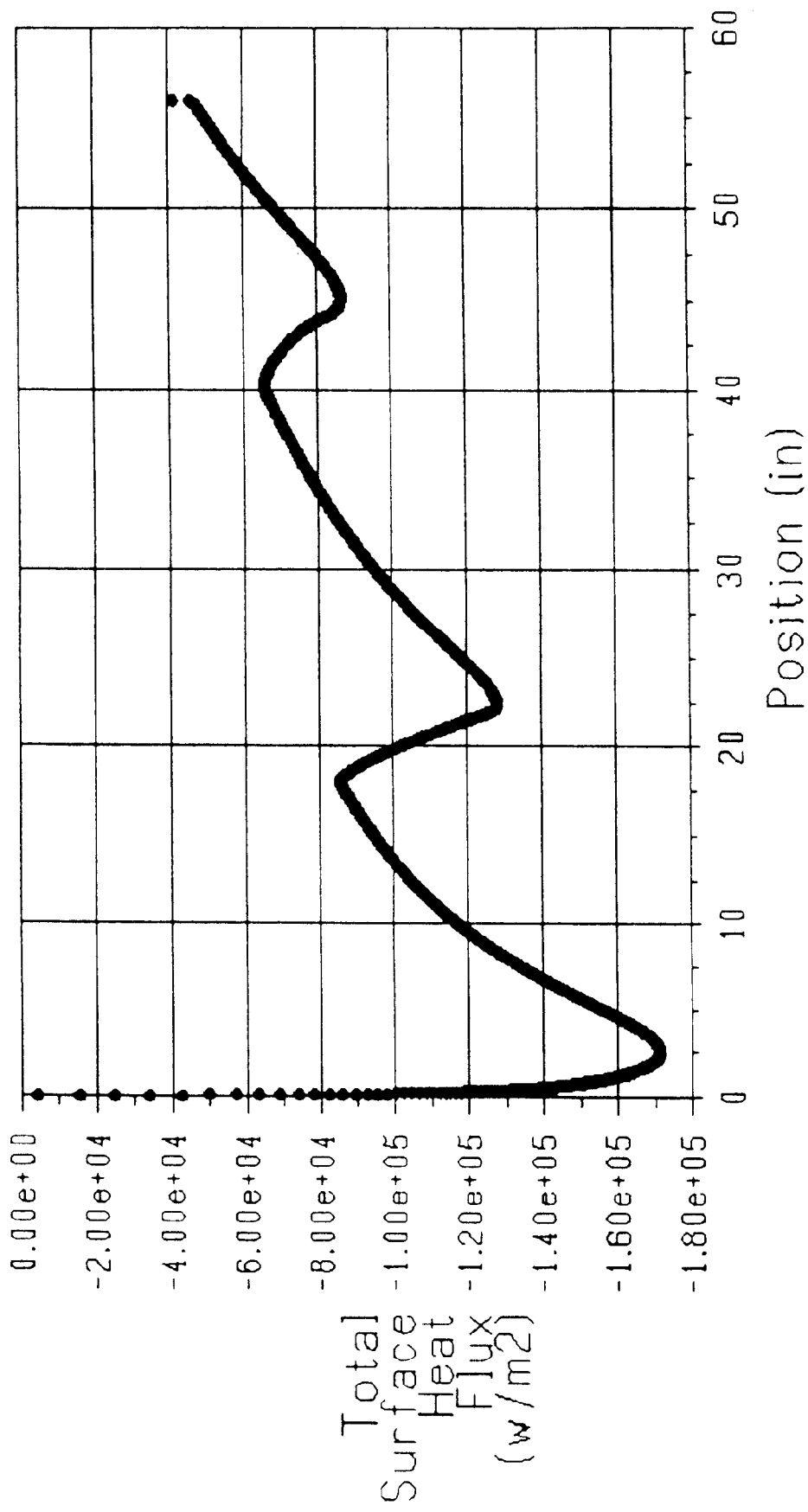
FIG. 72 is a plot showing heat flux for heat flowing through the heat transfer wall for the process reported in Example 10.

The results show improvement in reactor performance by grading both the catalyst to reduce the activity near the front and by increasing the amount of thermal resistance (i.e., reducing the thermal conductivity of the thermal resistance layer) in the thermal resistance layer near the end of the reactor. The conversion increases with only a modest reduction to selectivity and minor increase in the maximum temperature. The temperature profiles are shown in FIG. 71. The curve labeled "A" is for in the structured wall for supporting the catalyst. The curve labeled "B" is in the thermal resistance layer. The line labeled "C" is in the center of the open bulk flow region of the process microchannel. The heat flux at 200 ms through the heat transfer wall is shown in FIG. 72.

EXAMPLE 11

The catalyst structure is divided into several sections along the length of the process microchannel. The thermal resistance layer is also divided into the same number of sections. The details of catalyst activity and thermal resistance in each section are given in the following table.

| | Sectional catalyst activity and thermal resistance Baseline thermal conductivity: 2.23 W/m-K (1y) Thermal resistance layer thickness: 0.02 inch (0.508 mm) | | |
|---|---|---|---|
| Section | Location | Kinetics scale factor (1x is as reported previously) | Thermal conductivity scale factor |
| 1 | 0-18 | 0.5x | 1y |
| 2 | 18-22 | Linear from 0.5x to 1.2x | 1y |
| 3 | 22-40 | 1.2x | 1y |
| 4 | 40-44 | Linear from 1.2x to 1.5x | Linear from 1y to 0.5y |
| 5 | 44-56 | 1.5x | 0.5y |

| | Reactor performance | |
|---|---|---|
| Contact time | ms | 200 |
| Conversion | EB | 50.6% |
| Conversion | O$_2$ | 64.4% |
| Selectivity | ST | 97.5% |
| Selectivity | CO | 0.5% |
| Selectivity | CO2 | 2.0% |
| T, max | C | 462 |

Figure 73:
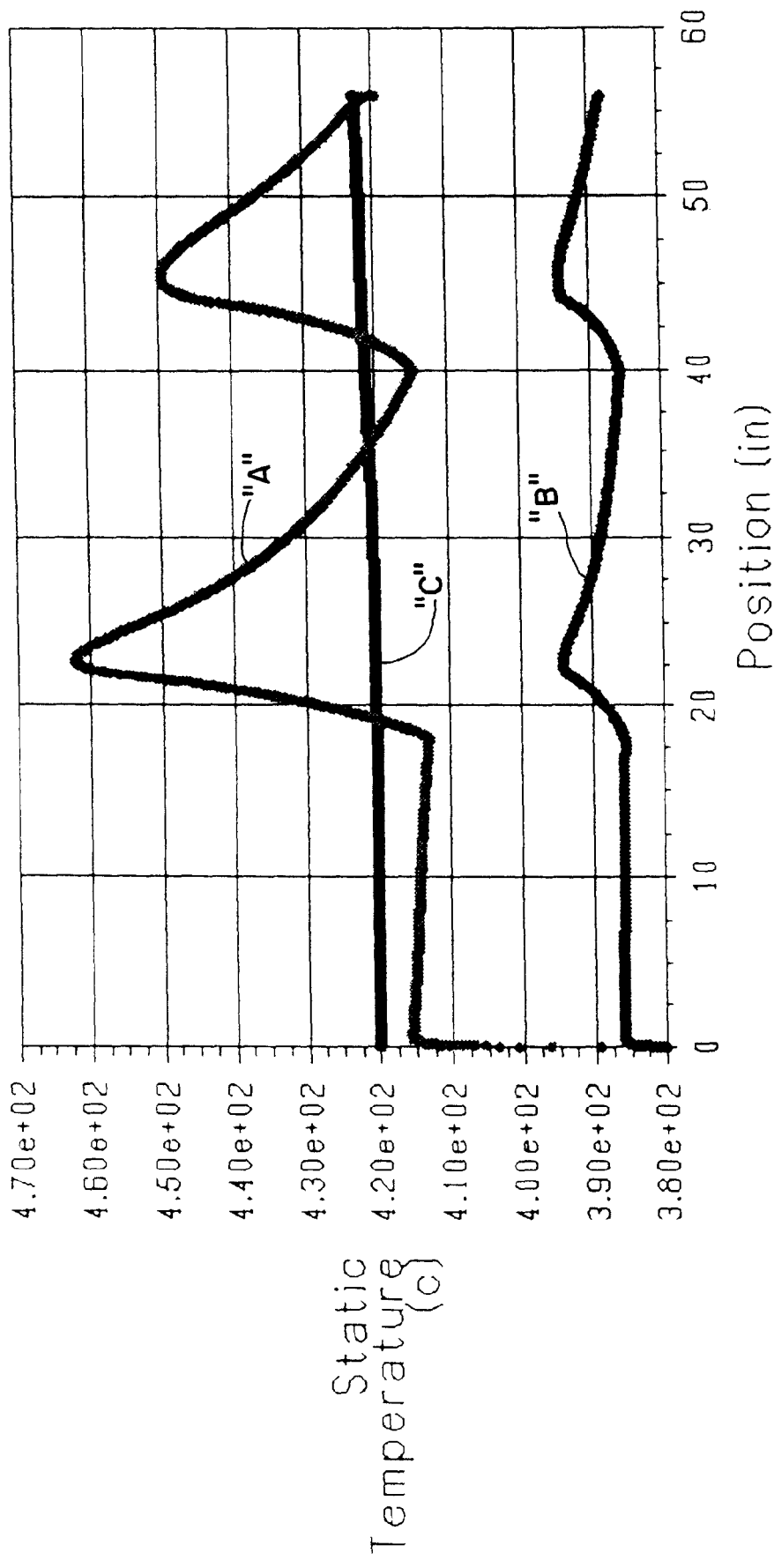
FIG. 73 is a plot showing three temperature profiles within a microchannel reactor for the process reported in Example 11.
Figure 74:
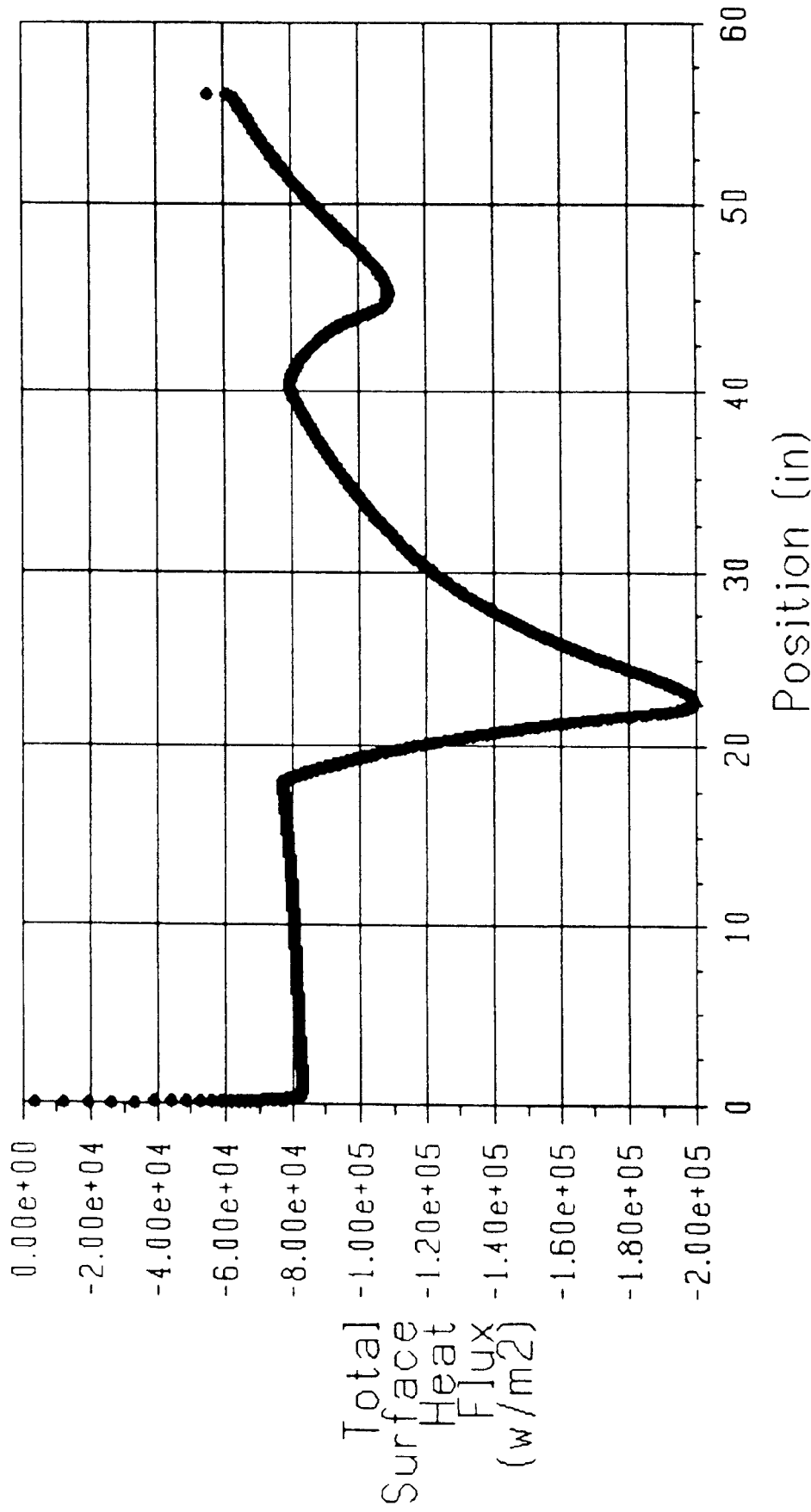
FIG. 74 is a plot showing heat flux for heat flowing through the heat transfer wall for the process reported in Example 11.

The modest change in the catalyst loading in the first section shifts the maximum hot spot downstream. The temperature profiles for the contact time of 200 ms are shown in FIG. 73. The curve labeled "A" is for the structured wall for supporting the catalyst as indicated above. The curve labeled "B" is for the thermal resistance layer. The line labeled "C" is for the center of the open bulk flow region of the process microchannel. The heat flux through the heat transfer wall at 200 ms contact time is shown in FIG. 74.

EXAMPLE 12

Figure 75:
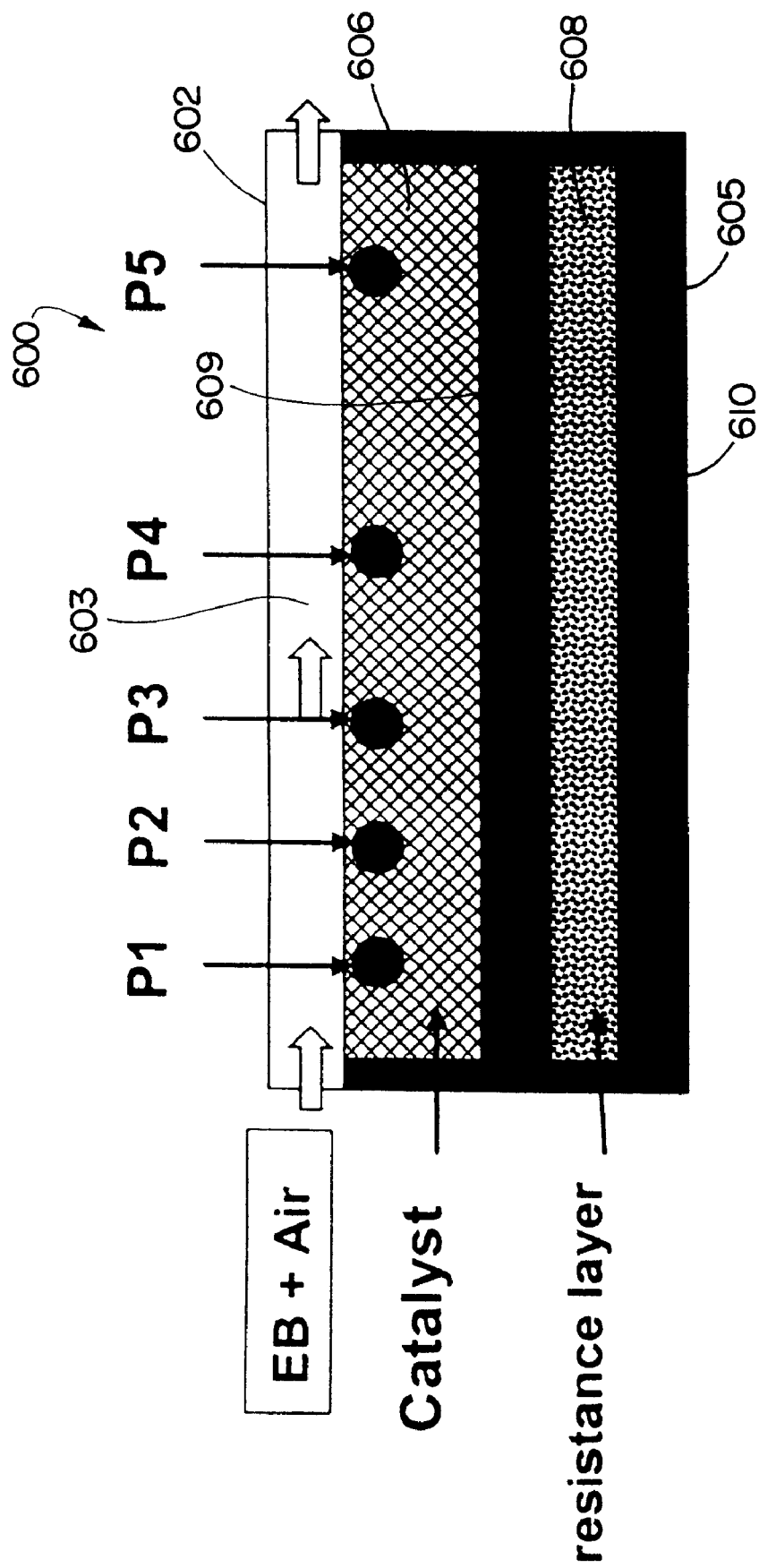
FIG. 75 is a schematic illustration of the process microchannel and heat transfer wall for the process reported in Example 12.

CFD simulations are carried out to examine how reactor temperature responds to changes of operating parameters. The operating parameter reviewed for this study is the feed temperature. At time zero, the reactor is at steady state with the process feed stream temperature at 410° C. Then, the feed temperature is raised to 420° C. This temperature change leads to subsequent changes in reactor performance, temperature and other variables until a new steady state, if any, is reached. In order to obtain details of how the reactor responds to this change, catalyst temperature is monitored at five locations as illustrated in the following FIG. 75. These five locations are distributed along the process microchannel length with more points in the first half of the process microchannel. P1 is 5 inches (12.7 cm) from the inlet. P2 is 8 inches (20.3 cm) from the inlet. P3 is 10 inches (25.4 cm) from the inlet. P4 is 15 inches (38.1 cm) from the inlet. P5 is 40 inches (101.6 cm) from the inlet. All locations are 0.01 inch (0.254 mm) from the surface of the structure facing the bulk flow region.

Figure 76:
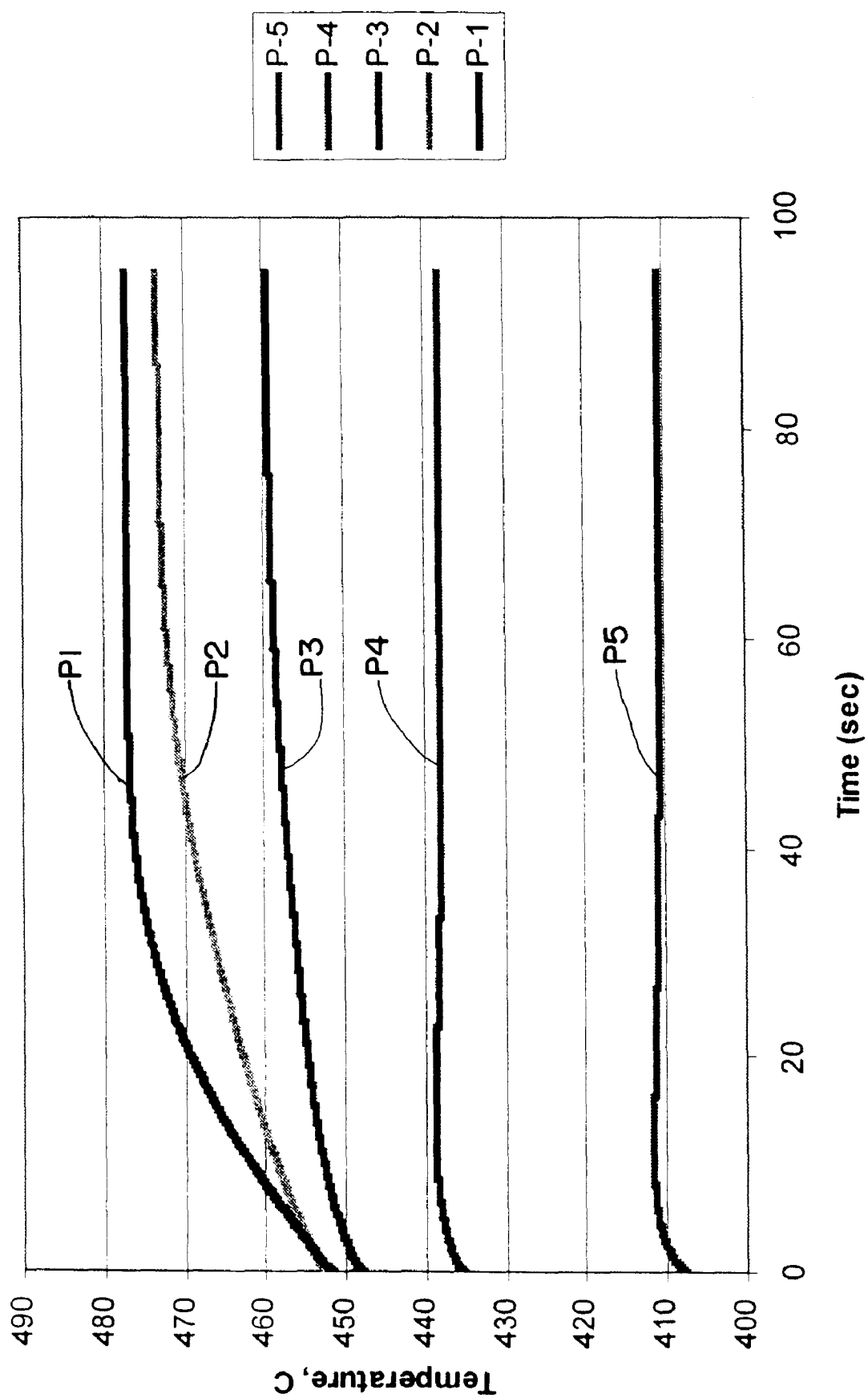
FIG. 76 is a plot of temperature profiles for the positions P1 through P5 in the microchannel reactor discussed in Example 12.

Other conditions include:
Catalyst activity is 50% of the original
Contact time: 1000 ms
Heat resistance layer thickness: 0.02 inch (0.508 mm)
Effective thermal conductivity of heat resistance layer: 1 W/m-K
Uniform catalyst activity and thermal resistance of the heat resistance layer along the reactor length The temperatures at the five locations on the catalyst are plotted in FIG. 76. The overall trends are temperature increase due to higher ethylbenzene conversion under 10 degree higher feed temperature condition. Temperature overshoot is observed only for point P-5 and P-4 at very small magnitude. This small transient effect away from the hot spot is not expected to create problems for reactor operation since the temperature levels are low at P5 and P4 locations. FIG. 76 also reveals that the elapsed time before the stable temperature is reached depends on the location. At 95 second after the temperature change in the feed, the temperature reaches stable values at all locations monitored. At 50 seconds, the temperature at P1 reaches a stable level, but not at P2 and P3 at where the temperatures still climbs higher.

The table below compares the performance of three CFD cases. First case is steady state model with feed temperature at 410° C., and the second case is also steady state case with feed temperature at 420° C. The third case is transient simulation wherein the feed temperature is changed from 410° C. to 420° C. at time zero at 95 seconds after the temperature change of the process feed stream. The reactor almost reaches steady state after 95 seconds. The maximum temperature overshoots one degree and the oxygen conversion is a few percent higher. The reactor operation is robust to the perturbation with the use of the thermal resistance layer to create a lower coolant temperature (380° C. for the reported simulations) and a warmer and stable reaction operating temperature.

| Reactor Performance Comparison | | | | |
|---|---|---|---|---|
| CFD cases | | Steady | Steady | Transient |
| T, C. feed | | 410 | 420 | 420 |
| Conversion | EB | 30.8% | 33.3% | 33.5% |
| Conversion | O$_2$ | 33.0% | 37.6% | 40.5% |
| Selectivity | Styrene | 98.5% | 98.3% | 98.1% |
| Selectivity | CO | 0.3% | 0.3% | 0.4% |

-continued

Reactor Performance Comparison

| CFD cases | | Steady | Steady | Transient |
|---|---|---|---|---|
| Selectivity | $CO_2$ | 1.2% | 1.4% | 1.5% |
| T, max | C. | 453 | 479 | 480 |

While the invention has been explained in relation to various embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for converting ethylbenzene to styrene, comprising:
   flowing a feed composition comprising ethylbenzene in at least one styrene-forming process microchannel in contact with at least one catalyst to dehydrogenate the ethylbenzene and form a product comprising styrene;
   exchanging heat between the process microchannel and at least one heat exchange channel in thermal contact with the process microchannel; and
   removing product from the process microchannel;
   wherein the ethylbenzene is formed by contacting benzene with ethylene in the presence of at least one alkylation catalyst; and
   the ethylbenzene is formed in at least one ethylbenzene-forming process microchannel, the styrene-forming process microchannel and the ethylbenzene-forming process microchannel being the same or different.

2. The process of claim 1 wherein the catalyst in the styrene-forming process microchannel comprises at least one dehydrogenation catalyst.

3. The process of claim 1 wherein the feed composition is combined with a fluid comprising oxygen and the catalyst in the styrene-forming process microchannel comprises at least one oxidative dehydrogenation catalyst.

4. The process of claim 1 wherein the ethylene is formed by dehydrogenating ethane in the presence of at least one dehydrogenation catalyst in at least one ethylene-forming process microchannel, the styrene-forming process microchannel and the ethylene-forming process microchannel being the same or different.

5. The process of claim 1 wherein the ethylene is formed by reacting ethane with oxygen in the presence of at least one oxidative dehydrogenation catalyst in at least one ethylene-forming process microchannel, the styrene-forming process microchannel and the ethylene-forming process microchannel being the same or different.

6. The process of claim 1 wherein the feed composition further comprises, ethane, oxygen and hydrogen, and the catalyst comprises at least one oxidative dehydrogenation catalyst.

7. The process of claim 6 wherein the product comprises styrene, ethylbenzene, ethylene, and hydrogen.

8. The process of claim 7 wherein the ethylbenzene in the product is recycled to the feed composition.

9. The process of claim 7 wherein the hydrogen in the product is recycled to the feed composition.

10. The process of claim 7 wherein the ethylene in the product is reacted with benzene in the presence of at least one alkylation catalyst to form ethylbenzene, the ethylbenzene being recycled to the feed composition.

11. The process of claim 10 wherein the ethylene is reacted with the benzene in at least one process microchannel containing the alkylation catalyst.

12. The process of claim 3 wherein the feed composition and the oxygen are mixed prior to entering the styrene-forming process microchannel.

13. The process of claim 3 wherein a staged addition feed stream comprising the oxygen flows in a staged addition channel, the staged addition channel being adjacent to the styrene-forming process microchannel, the styrene-forming process microchannel having an entrance for the feed composition, the feed composition entering the styrene-forming process microchannel through the entrance for the feed composition, the staged addition feed stream flowing from the staged addition channel into the styrene-forming process microchannel, the staged addition feed stream entering the styrene-forming process microchannel downstream of the entrance for the feed composition and contacting the feed composition in the styrene-forming process microchannel.

14. The process of claim 1 wherein the feed composition further comprises air and/or steam.

15. The process of claim 3 wherein the feed composition comprises ethylbenzene and oxygen.

16. The process of claim 15 wherein the feed composition further comprises nitrogen.

17. The process of claim 13 wherein the staged addition feed stream comprises air, oxygen or oxygen enriched air.

18. The process of claim 2 wherein the catalyst comprises at least one oxide of iron, chromium, platinum, iridium, rhodium, palladium, or a combination thereof.

19. The process of claim 2 wherein the catalyst comprises iron oxide and one or more of potassium oxide, molybdenum oxide, cerium oxide, and calcium carbonate.

20. The process of claim 3 wherein the catalyst comprises at least one oxide of vanadium, molybdenum, tungsten, or a combination of two or more thereof.

21. The process of claim 3 wherein the catalyst comprises $FeVO_4$, $CrVO_4$, $NaVO_3$, $BiVO_4$, $AlVO_4$, $CeVO_4$, $VOPO_4$, $LaVO_4$, $SmVO_4$, $NiMoO_4$, $MgMoO_4$, $CaMoO_4$, $FeMoO_4$, $Fe_2(MoO_4)_3$, $MgWO_4$, $CaWO_4$, $NiWO_4$, $FeWO_4$, $K_2O$, $MoO_3$, $SiO_2$, $TiO_2$, or a combination of two or more thereof.

22. The process of claim 1 wherein the catalyst in the styrene-forming process microchannel comprises a graded catalyst.

23. The process of claim 1 wherein the catalyst in the styrene-forming process microchannel is supported on a support, the support comprising a heat conductive material.

24. The process of claim 1 wherein the catalyst in the styrene-forming process microchannel is supported on a support, the support being in the form of a foam, felt, wad, fin, or a combination of two or more thereof.

25. The process of claim 1 wherein the catalyst in the styrene-forming process microchannel is supported on a support, the support comprising a microgrooved support strip with a support strip having a length with a center axis extending along the length, a first surface, a first side edge, a second side edge, a front edge extending from the first side edge to the second side edge, a back edge extending from the first side edge to the second side edge, a plurality of parallel microgrooves in the first surface extending between the first side edge and the second side edge at an angle relative to the center axis.

26. The process of claim 25 wherein the support strip further comprises a plurality of parallel microgrooves extending between the front edge of the support strip and the first side edge of the support strip, and a plurality of parallel microgrooves extending between the back edge of the support strip and the second side edge of the support strip.

27. The process of claim 25 wherein the support strip is made of a thermally conductive material.

28. The process of claim 1 wherein the styrene-forming process microchannel exchanges heat with a heat exchange fluid flowing in the heat exchange channel.

29. The process of claim 28 wherein the heat exchange fluid undergoes a phase change as it flows in the heat exchange channel.

30. The process of claim 1 wherein the heat flux between the heat exchange channel and the styrene-forming process microchannel is in the range from about 0.01 to about 250 watts per square centimeter of surface area of the process microchannel.

31. The process of claim 1 wherein an endothermic process is conducted in the heat exchange channel.

32. The process of claim 1 wherein an exothermic process is conducted in the heat exchange channel.

33. The process of claim 1 wherein the process is conducted in a microchannel reactor comprising a plurality of the styrene-forming process microchannels and a plurality of the heat exchange channels.

34. The process of claim 33 wherein the microchannel reactor further comprises at least one header providing for the flow of the reactant composition into the process microchannels and at least one footer providing for the flow of product out of the process microchannels.

35. The process of claim 33 wherein the microchannel reactor further comprises a preheat section for heating the feed composition prior to flowing the feed composition in the styrene-forming process microchannels and a cool down section for cooling product flowing out of the styrene-forming process microchannels.

36. The process of claim 35 wherein the product flows from the cool down section to a styrene knockout drum where the product is cooled.

37. The process of claim 35 wherein the microchannel reactor comprises a microchannel reactor core containing the process microchannels and heat exchange channels, the microchannel reactor core and the cool down section being in thermal contact with the preheat section.

38. The process of claim 37 wherein the microchannel reactor core and the cool down section are adjacent to the preheat section.

39. The process of claim 1 wherein the gas hourly space velocity for the flow of the feed composition in the at least one styrene-forming process microchannel is at least about 1000 normal liters of feed per hour per liter of volume within the process microchannel.

40. The process of claim 1 wherein the catalyst in the styrene-forming process microchannel is supported on a support, the support having a length with a center axis extending along the length, a first surface, a first side edge, a second side edge, a front edge extending from the first side edge to the second side edge, a back edge extending from the first side edge to the second side edge, and a plurality of parallel microgrooves in the first surface aligned at an angle of about 90° C. relative to the center axis.

41. The process of claim 1 wherein the catalyst in the styrene-forming process microchannel is supported on a support, the support having a length with a center axis extending along the length, a first surface, a first side edge, a second side edge, a front edge extending from the first side edge to the second side edge, a back edge extending from the first side edge to the second side edge, and a plurality of parallel microgrooves in the first surface aligned parallel to the center axis.

42. The process of claim 1 wherein the catalyst in the styrene-forming process microchannel is supported by a composite support structure, comprising:

at least one first support strip comprising a first surface, a second surface, a length with a center axis extending along the length, a front edge, a back edge, a first side edge, a second side edge, the front edge and the back edge extending from the first side edge and to the second side edge, and a plurality of parallel microgrooves in the first surface;

at least one second support strip comprising a first surface, a second surface, a length with a center axis extending along the length, a front edge, a back edge, a first side edge, a second side edge, the front edge and the back edge extending from the first side edge to the second side edge, and a plurality of parallel microgrooves in the first surface;

the first support strip being adjacent to the second support strip with the second surface of the first support strip contacting the first surface of the second support strip;

the microgrooves penetrating through the support strips sufficiently to permit fluid to flow through the support strips from one support strip to another;

microgrooves in the first surface of the first support strip intersecting microgrooves in the first surface of the second support strip to provide through holes extending through the first support strip and through the second support strip.

43. The process of claim 1 wherein a heat transfer wall is positioned between the styrene-forming process microchannel and the heat exchange channel, the heat transfer wall comprising at least one thermal resistance layer.

44. The process of claim 13 wherein a reaction zone is positioned within the styrene-forming process microchannel, the staged addition feed stream contacting the feed composition in the reaction zone.

45. The process of claim 13 wherein a mixing zone and a reaction zone are positioned within the styrene-forming process microchannel, the mixing zone being upstream of the reaction zone, the staged addition feed stream contacting the feed composition in the mixing zone.

46. The process of claim 13 wherein a mixing zone and a reaction zone are positioned within the styrene-forming process microchannel, the mixing zone being upstream of the reaction zone, part of the staged addition feed stream contacting the feed composition in the mixing zone, and part of the staged addition feed stream contacting the feed composition in the reaction zone.

47. The process of claim 1 wherein the styrene-forming process microchannel has an internal dimension of width or height of up to about 10 mm.

48. The process of claim 1 wherein the styrene-forming process microchannel has an internal dimension of width or height of up to about 2 mm.

49. The process of claim 1 wherein the styrene-forming process microchannel is made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

50. The process of claim 13 wherein the staged addition channel has an internal dimension of width or height of up to about 10 mm.

51. The process of claim 13 wherein the staged addition channel has an internal dimension of width or height of up to about 2 mm.

52. The process of claim 13 wherein the staged addition channel is made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

53. The process of claim 1 wherein the heat exchange channel is adjacent to the process microchannel.

54. The process of claim 1 wherein the heat exchange channel is in thermal contact with the process microchannel.

55. The process of claim 1 wherein the heat exchange channel comprises a microchannel.

56. The process of claim 1 wherein the heat exchange channel has an internal dimension of width or height of up to about 10 mm.

57. The process of claim 1 wherein the heat exchange channel has an internal dimension of width or height of up to about 2 mm.

58. The process of claim 1 wherein the heat exchange channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

59. The process of claim 13 wherein the styrene-forming process microchannel and the staged addition channel have a common wall, the common wall having a plurality of openings extending along at least part of the length of the process microchannel, the staged addition feed stream flowing through the openings in the common wall.

60. The process of claim 13 wherein the styrene-forming process microchannel and the staged addition microchannel have a common wall with an apertured section in the common wall, the staged addition feed stream flowing from the staged addition channel through the apertured section into the process microchannel.

61. The process of claim 60 wherein the apertured section comprises a relatively thin sheet overlying a relatively thick sheet or plate, the relatively thin sheet containing an array of relatively small apertures, and the relatively thick sheet or plate containing an array of relatively large apertures, at least some of the relatively small apertures being aligned with the relatively large apertures.

62. The process of claim 60 wherein the apertured section comprises apertures that are partially filled with a coating material.

63. The process of claim 60 wherein the apertured section is made from a porous material.

64. The process of claim 60 wherein the apertured section is made from a porous material that is heat treated.

65. The process of claim 60 wherein the apertured section is made from a porous material, the porous material being metallic, nonmetallic, oxidized, and/or coated with nickel or alumina.

66. The process of claim 60 wherein the apertured section is made from a porous material, the surface of the porous material being treated by filling the pores on the surface with a liquid filler, solidifying the filler, grinding or polishing the surface, and removing the filler.

67. The process of claim 3 wherein the catalyst comprises $V_2O_5$, $MoO_3$, $WO_3$, or a combination of two or more thereof.

68. The process of claim 3 wherein the catalyst comprises at least one vanadate, molybdate, tungstate, or a combination of two or more thereof.

69. The process of claim 1 wherein the catalyst in the styrene-forming process microchannel is in the form of particulate solids.

70. The process of claim 1 wherein the catalyst in the styrene-forming process microchannel is washcoated on interior walls of the process microchannel or grown on interior walls of the process microchannel from solution.

71. The process of claim 1 wherein the catalyst in the styrene-forming process microchannel comprises a support, an optional buffer layer overlying the support, an interfacial layer overlying the optional buffer layer or the support, and a catalyst material dispersed or deposited on the interfacial layer.

72. The process of claim 1 wherein the catalyst in the styrene-forming process microchannel is supported by a support, the support being made of a material comprising one or more of silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof.

73. The process of claim 1 wherein the catalyst in the styrene-forming process microchannel is supported on a support, the support comprising an alloy comprising Ni, Cr and Fe, or an alloy comprising Fe, Cr, Al and Y.

74. The process of claim 1 wherein the catalyst in the styrene-forming process microchannel is supported on a support having a flow-by configuration, a flow-through configuration, a honeycomb structure or a serpentine configuration.

75. The process of claim 1 wherein the catalyst in the styrene-forming process microchannel is supported on a support having a flow-by configuration with an adjacent gap, a foam configuration with an adjacent gap, a fin structure with gaps, a washcoat on a substrate, or a gauze configuration with a gap for flow.

76. The process of claim 1 wherein the catalyst in the styrene-forming process microchannel is supported on a support, the support comprising a fin assembly comprising at least one fin.

77. The process of claim 76 wherein the fin assembly comprises a plurality of parallel spaced fins.

78. The process of claim 76 wherein the fin has an exterior surface and a porous material overlies at least part of the exterior surface of the fin, the catalyst being supported by the porous material.

79. The process of claim 78 wherein the porous material comprises a coating, fibers, foam or felt.

80. The process of claim 76 wherein the fin has an exterior surface and a plurality fibers or protrusions extend from at least part of the exterior surface of the fin, the catalyst being supported by the protrusions.

81. The process of claim 76 wherein the fin has an exterior surface and the catalyst is: washcoated on at least part of the exterior surface of the fin; grown on at least part of the exterior surface of the fin from solution; or deposited on at least part of the exterior surface of the fin using vapor deposition.

82. The process of claim 76 wherein the fin assembly comprises a plurality of parallel spaced fins, at least one of the fins having a length that is different than the length of the other fins.

83. The process of claim 76 wherein the fin assembly comprises a plurality of parallel spaced fins, at least one of the fins having a height that is different than the height of the other fins.

84. The process of claim 76 wherein the fin has a cross section having the shape of a square, a rectangle, or a trapezoid.

85. The process of claim 76 wherein the fin is made of a material comprising: steel; aluminum; titanium; iron; nickel; platinum; rhodium; copper; chromium; brass; an alloy of any of the foregoing metals; a polymer; ceramics; glass; a composite comprising polymer and fiberglass; quartz; silicon; or a combination of two or more thereof.

86. The process of claim 76 wherein the fin is made of an alloy comprising Ni, Cr and Fe, or an alloy comprising Fe, Cr, Al and Y.

87. The process of claim 76 wherein the fin is made of an $Al_2O_3$ forming material or a $Cr_2O_3$ forming material.

88. The process of claim 25 wherein the support strip further comprises a plurality of parallel microgrooves extending between the front edge of the support strip and the second side edge of the support strip.

89. The process of claim 25 wherein the support strip further comprises a plurality of parallel microgrooves extending between the back edge of the support strip and the first side edge of the support strip.

90. The process strip of claim 25 wherein the support strip further comprises a plurality of parallel microgrooves extending between the front edge of the support strip and the first side edge of the support strip.

91. The process of claim 25 wherein the support strip further comprises a plurality of parallel microgrooves extending between the back edge of the support strip and the second side edge of the support strip.

92. The process of claim 25 wherein the support strip further comprises a plurality of parallel microgrooves extending between the front edge of the support strip and the second side edge of the support strip, and a plurality of parallel microgrooves extending between the back edge of the support strip and the first side edge of the support strip.

93. The process strip of claim 25 wherein the microgrooves are oriented toward the front edge and the first side edge at an angle with the center axis of more than about 0° and less than about 90°.

94. The process of claim 25 wherein the microgrooves are oriented toward the front edge and the first side edge at an angle with the center axis in the range from about 50° to about 80°.

95. The process of claim 25 wherein the microgrooves are oriented toward the front edge and the first side edge at an angle with the center axis of more than 90° and less than about 180°.

96. The process strip of claim 25 wherein the microgrooves are oriented toward the front edge and the first side edge at an angle with the center axis in the range from about 100° to about 150°.

97. The process of claim 25 wherein the front edge and the back edge are sufficiently closed to block the flow of fluid through the front edge and the back edge.

98. The process of claim 25 wherein the front edge and the back edge are sufficiently open to permit the flow of fluid through front edge and the back edge.

99. The process of claim 25 wherein the first side edge and the second side edge are sufficiently open to permit the flow of fluid through the first side edge and the second side edge.

100. The process of claim 25 wherein the first side edge and the second side edge are sufficiently closed to block the flow of fluid through the first side edge and the second side edge.

101. The process of claim 25 wherein the support strip has a thickness in the range from about 1 to about 1000 microns.

102. The process of claim 25 wherein the microgrooves have a depth in the range from about 0.1 to about 1000 microns.

103. The process of claim 25 wherein the microgrooves have widths in the range from about 0.1 to about 1000 microns.

104. The process of claim 25 wherein the spacing between the microgrooves is in the range up to about 1000 microns.

105. The process of claim 25 wherein the microgrooves have cross sections in the shape of a square, rectangle, vee, semi-circle, dovetail and/or trapezoid.

106. The process of claim 27 wherein the thermally conductive material comprises metal, silicon carbide, graphite, or a combination of two or more thereof.

107. The process of claim 27 wherein the thermally conductive material comprises stainless steel or an alloy comprising iron, chromium, aluminum and yttrium.

108. The process of claim 25 wherein the catalyst comprises particulates positioned in the microgrooves.

109. The process of claim 1 wherein the catalyst in the styrene-forming process microchannel is supported by a composite support structure, comprising:

at least one first support strip comprising a first surface, a second surface, a length with a center axis extending along the length, a front edge, a back edge, a first side edge, a second side edge, the front edge and the back edge extending from the first side edge and to the second side edge, a plurality of parallel microgrooves in the first surface extending from the front edge to the second side edge, and a plurality of parallel microgrooves in the first surface extending from first side edge to the back edge;

at least one second support strip comprising a first surface, a second surface, a length with a center axis extending along the length, a front edge, a back edge, a first side edge, a second side edge, the front edge and the back edge extending from the first side edge to the second side edge, a plurality of parallel microgrooves in the first surface extending from the front edge to the first side edge, and a plurality of parallel microgrooves in the first surface extending from second side edge to the back edge;

the first support strip being adjacent to the second support strip with the second surface of the first support strip contacting the first surface of the second support strip;

the front and back edges of each of the support strips being open to permit fluid to flow through the front and back edges;

the side edges of each of the support strips being closed to prevent fluid from flowing through the side edges;

each of the microgrooves penetrating through the support strips sufficiently to permit fluid to flow through the support strips from one support strip to another;

the microgrooves in the first surface of the first support strip being oriented toward the front edge and the first side edge of the first support strip and forming an angle with the center axis of more than about 0° and less than 90°; and the microgrooves in the first surface of the second support strip being oriented toward the front edge and the first side edge of the second support strip and forming an angle with the center axis of more than 90° and less than about 180°.

110. The process of claim 109 wherein the support structure further comprises end plates to prevent the flow of fluid out of the sides of the support structure.

111. The process of claim 109 wherein the support structure comprises a plurality of the first support strips and a plurality of the second support strips, the first and second support strips being stacked one above the other or positioned side by side one another in alternating sequence.

112. The process of claim 31 wherein the endothermic process comprises a steam reforming reaction or a dehydrogenation reaction.

113. The process of claim 32 wherein the exothermic process comprises a water-gas shift reaction, methanol synthesis reaction or ammonia synthesis reaction.

114. The process of claim 1 wherein fluid flows in the styrene-forming process microchannel in a first direction, and a heat exchange fluid flows in the heat exchange channel in a second direction, the second direction being cross current relative to the first direction.

115. The process of claim 1 wherein fluid flows in the styrene-forming process microchannel in a first direction, and a heat exchange fluid flows in the heat exchange channel in a second direction, the second direction being cocurrent or counter current relative to the first direction.

116. The process of claim 1 wherein a heat exchange fluid flows in the heat exchange channel, the heat exchange fluid comprising the feed composition or the product.

117. The process of claim 1 wherein a heat exchange fluid flows in the heat exchange channel, the heat exchange fluid comprising one or more of air, steam, liquid water, carbon monoxide, carbon dioxide, gaseous nitrogen, liquid nitrogen, inert gas, gaseous hydrocarbon, oil and/or liquid hydrocarbon.

118. The process of claim 1 wherein the conversion of ethylbenzene is at least about 25% per cycle.

119. The process of claim 1 wherein the conversion of ethylbenzene is at least about 70% per cycle.

120. The process of claim 1 wherein the selectivity to styrene is at least about 50% per cycle.

121. The process of claim 1 wherein the selectivity to styrene is at least about 80% per cycle.

122. The process of claim 1 wherein the selectivity to styrene is at least about 90% per cycle.

123. The process of claim 1 wherein the catalyst in the styrene-forming process microchannel is supported by a composite support structure, comprising:
    at least one first support strip comprising a first surface, a second surface, a length with a center axis extending along the length, a front edge, a back edge, a first side edge, a second side edge, the front edge and the back edge extending from the first side edge and to the second side edge, a plurality of parallel microgrooves in the first surface aligned at an angle of about 90° with the center axis; and
    at least one second support strip comprising a first surface, a second surface, a length with a center axis extending along the length, a front edge, a back edge, a first side edge, a second side edge, the front edge and the back edge extending from the first side edge to the second side edge, a plurality of parallel microgrooves in the first surface aligned parallel with the center axis;
    the first support strip being adjacent to the second support strip with the second surface of the first support strip contacting the first surface of the second support strip;
    the microgrooves penetrating through the support strips sufficiently to permit fluid to flow through the support strips from one support strip to another support strip.

124. The process of claim 123 wherein the through holes are of sufficient dimension to permit reactants and/or product to flow from the first surface of the first support strip to the first surface of the second support strip and/or from the first surface of the second support strip to the first surface of the first support strip.

125. The process of claim 123 wherein the first support strip and the second support strip are made of thermally conductive materials and the contacting between the second surface of the first support strip and the first surface of the second support strip is sufficient to permit heat to be conducted between the first support strip and the second support strip.

126. The process of claim 43 wherein the thermal resistance layer is positioned on the heat transfer wall and/or embedded within the heat transfer wall.

127. The process of claim 43 wherein the thermal resistance layer comprises a vacuum, a gaseous material, a liquid and/or a solid material.

128. The process of claim 43 wherein the thermal resistance layer comprises a solid material which contains void spaces, openings and/or through holes.

129. The process of claim 43 wherein the thermal resistance layer comprises one or more strips or shims which contain void spaces, openings and/or through holes.

130. The process of claim 43 wherein the thermal resistance layer comprises one or more strips or shims with grooves formed in the strip.

131. The process of claim 43 wherein the thermal resistance layer comprises one or more strips or shims, each of the shims having a first surface and a second surface, and grooves formed in the first surface and/or second surface.

132. The process of claim 43 wherein the thermal resistance layer comprises one or more sub-assemblies, each sub-assembly comprising two or more shims stacked one above another with one or more void spaces positioned between the shims.

133. The process of claim 43 wherein the heat transfer wall and/or thermal resistance layer comprise one or more sub-assemblies, each sub-assembly comprising two or more shims stacked one above another with one or more void spaces positioned between the shims.

* * * * *